US007166426B2

(12) United States Patent
Arcangel et al.

(10) Patent No.: US 7,166,426 B2
(45) Date of Patent: *Jan. 23, 2007

(54) HCV ASSAY

(75) Inventors: Phillip Arcangel, Ricmond, CA (US); David Chien, Alamo, CA (US)

(73) Assignee: Novartis Vaccines And Diagnostics, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/658,782

(22) Filed: Sep. 8, 2003

(65) Prior Publication Data
US 2004/0142321 A1 Jul. 22, 2004

Related U.S. Application Data

(60) Provisional application No. 60/409,515, filed on Sep. 9, 2002.

(51) Int. Cl.
- C12Q 1/70 (2006.01)
- G01N 33/53 (2006.01)
- A61K 39/29 (2006.01)
- C12N 7/00 (2006.01)
- A61K 39/00 (2006.01)

(52) U.S. Cl. ............... 435/5; 435/7.1; 435/235.1; 424/189.1; 424/192.1; 424/228.1

(58) Field of Classification Search ............ 424/228.1, 424/189.1, 192.1; 435/5, 69.7, 6, 69.1; 530/300, 530/350
See application file for complete search history.

(56) References Cited

U.S. PATENT DOCUMENTS

| | | | |
|---|---|---|---|
| 5,350,671 | A | 9/1994 | Houghton et al. |
| 5,712,087 | A | 1/1998 | Houghton et al. |
| 5,843,752 | A | 12/1998 | Dasmahapatra et al. |
| 5,871,904 | A | 2/1999 | Kashiwakuma et al. |
| 5,990,276 | A | 11/1999 | Zhang et al. |
| 6,171,782 | B1 | 1/2001 | Houghton et al. |
| 6,210,675 | B1 | 4/2001 | Highfield et al. |
| 6,306,579 | B1 | 10/2001 | Seidel et al. |
| 6,428,792 | B1 | 8/2002 | Valenzuela et al. |
| 6,632,601 | B2 | 10/2003 | Chien et al. |
| 6,797,809 | B2 | 9/2004 | Chien et al. |

FOREIGN PATENT DOCUMENTS

| | | |
|---|---|---|
| EP | 318216 | 5/1989 |
| EP | 388232 | 9/1990 |
| EP | 0450931 B1 | 10/1991 |
| EP | 0472207 A2 | 2/1992 |
| WO | WO 93/00365 | 1/1993 |
| WO | WO 94/01778 | 1/1994 |
| WO | WO 97/44469 | 11/1997 |
| WO | WO 01/96870 | 12/2001 |

OTHER PUBLICATIONS

Chien et al. (1999) Journal of Clinical Microbiology, vol. 37, No. 5; p. 1393-97.*
Choo, Q.L. et al. Genetic organization and diversity of the hepatitis C virus (1991) Proc. Natl. Acad. Sci., 88:2451-2455.*
Wang et al., "Molecular design and immunogenicity studies of multiple antigenic peptide corresponding to envelope glycoprotein hypervariable region 1 of hepatitis C virus (abstract)." Chinese J. Exp. Clin. Virol., Jun. 2000, vol. 14, No. 2.*
Puntoriero et al., "Towards a solution for hepatitis C virus hypervariability: mimotopes of the hypervariable region 1 can induce antibodies cross-reacting with a large number of viral variants," The EMBO Journal, vol. 17, No. 13 (1998), pp. 321-3533.*
Beld et al., "Evaluation of automated RNA-extraction technology and a qualitative HCV assay for sensitivity and detection of HCV RNA in pool-screening systems," *Transfusion* 40:575-579, 2000.
Chen et al., "Human and murine antibody recognition is focused on the ATPase/helicase domain, but not the protease domain of the hepatitis C virus non-structural 3 protein," *Hepatology* 28:219-224, 1998.
Chien et al., "Diagnosis of Hepatitis C Virus (HCV) Infection Using an Immunodominant Chimeric Polyprotein to Capture Circulating Antibodies: Reevaluation of the Role of HCV in Liver Disease," *Proc. Natl. Acad. Sci. U.S.A.* 89: 10011-10015 (1992).
Chien et al., "Use of Recombinant HCV Antigen in the Serodiagnosis of Hepatitis C Virus Infection: Significant Improvement in HCV Antibody Detection as Compared with the First Generation HCV C100-3 ELISA and the Synthetic Peptide EIA Tests," *Journal of Gastroenterology Hepatology* 8:S33-39 (1993).
Chien et al., "Distinct subtypes of hepatitis C virus defined by antibodies directed to the putative core, NS4, and NS5 region polypeptides," *Virol. Hepatitis and Liver Disease*:320-324, 1994.
Choo et al., "Isolation of a cDNA Clone Derived from a Blood-Borne Non-A, Non-B Viral Hepatits Genome," *Science* 244:359-362 (1989).
Choo et al., "Hepatitis C Virus: The Major Causative Agent of Viral Non-A, Non-B Hepatitis," *British Medical Bulletin* 46(2):423-441 (1990).
Cruse et al., Illustrated Dictionary of Immunology, CRC Press, Boca Raton FL, 1995, p. 76.
Ebeling et al., "Recombinant Immunoblot Assay for Hepatitis C Virus Antibody as Predictor of Infectivity," *Lancet* 335:982-983 (1990).

(Continued)

Primary Examiner—Bruce R. Campell
Assistant Examiner—M. Franco Salvoza
(74) Attorney, Agent, or Firm—Marcella Lillis; Roberta L. Robins; Alisa A. Harbin

(57) ABSTRACT

An HCV antigen/antibody/antigen assay is provided. The assay employs an isolated first antigen from a region of the HCV polyprotein, and an HCV multiple epitope fusion antigen that includes an epitope from the same region of the polyprotein as the first antigen. Both the first antigen and the multiple epitope fusion antigen bind antibodies present in an HCV-infected sample.

26 Claims, 22 Drawing Sheets

OTHER PUBLICATIONS

Houghton et al., "Molecular Biology of the Hepatitis C Viruses: Implications for Diagnos, Development and Control of Viral Disease," *Hepatology* 14:381-388 (1991).

Kotwal et al., "Detection of acute hepatitis C virus infection by ELISA using a synthetic peptide comprising a structural epitope," *Proc. Natl. Acad. Sci. USA* 89:4486-4489, 1992.

Kuo et al.,"An Assay for Circulating Antibodies to a Major Etiologic Virus of Human Non-A, Non-B Hepatitis," *Science* 244:362-364 (1989).

Pereboeva et al., "Hepatitis C Epitopes From Phage-Displayed cDNA Libraries and Improved Diagnosis with a Chimeric Antigen," *J. Medical Virology* 60:144-151, 2000.

Van der Poel et al., "Infectivity of Blood Seropositve for Hepatitis C Virus Antibodies," *Lancet* 335:558-560 (1990).

Van der Poel et al., "Confirmation of hepatitis C virus infection by new four-antigen recombinant immunoblot assay," *Lancet* 337:317-319, 1991.

Yao et al., "Molecular views of viral polyprotein processing revealed by the crystal structure of the hepatitis C virus bifunctional protease-helicase," *Structure* 7(11):1353-1363, 1999.

Chien et al., "Use of a Novel Hepatitis C Virus (HCV) Major-Epitope Chimeric Polypeptide for Diagnosis of HCV Infection," Journal of Clinical Microbiology, 37(5):1393-1397 (1999).

\* cited by examiner

```
                              1                                              10
                              M   A   P   I   T   A   Y   A   Q   Q
                              ATG GCG CCC ATC ACG GCG TAC GCC CAG CAG

20
          T   R   G   L   L   G   C   I   I   T   S   L   T   G   R
          ACA AGG GGC CTC CTA GGG TGC ATA ATC ACC AGC CTA ACT GGC CGG 30                                          40
          D   K   N   Q   V   E   G   E   V   Q   I   V   S   T   A
          GAC AAA AAC CAA GTG GAG GGT GAG GTC CAG ATT GTG TCA ACT GCT

50
          A   Q   T   F   L   A   T   C   I   N   G   V   C   W   T
          GCC CAA ACC TTC CTG GCA ACG TGC ATC AAT GGG GTG TGC TGG ACT 60                                          70
          V   Y   H   G   A   G   T   R   T   I   A   S   P   K   G
          GTC TAC CAC GGG GCC GGA ACG AGG ACC ATC GCG TCA CCC AAG GGT

80
          P   V   I   Q   M   Y   T   N   V   D   Q   D   L   V   G
          CCT GTC ATC CAG ATG TAT ACC AAT GTA GAC CAA GAC CTT GTG GGC 90                                         100
          W   P   A   P   Q   G   S   R   S   L   T   P   C   T   C
          TGG CCC GCT CCG CAA GGT AGC CGA TCA TTG ACA CCC TGC ACT TGC

110
          G   S   S   D   L   Y   L   V   T   R   H   A   D   V   I
          GGC TCC TCG GAC CTT TAC CTG GTC ACG AGG CAC GCC GAT GTC ATT 120                                         130
          P   V   R   R   R   G   D   S   R   G   S   L   L   S   P
          CCC GTG CGC CGG CGG GGT GAT AGC AGG GGC AGC CTG CTG TCG CCC

140
          R   P   I   S   Y   L   K   G   S   S   G   G   P   L   L
          CGG CCC ATT TCC TAC TTG AAA GGC TCC TCG GGG GGT CCG CTG TTG 150                                         160
          C   P   A   G   H   A   V   G   I   F   R   A   A   V   C
          TGC CCC GCG GGG CAC GCC GTG GGC ATA TTT AGG GCC GCG GTG TGC

170
          T   R   G   V   A   K   A   V   D   F   I   P   V   E   N
          ACC CGT GGA GTG GCT AAG GCG GTG GAC TTT ATC CCT GTG GAG AAC 180                                         190
          L   E   T   T   M   R   S   P   V   F   T   D   N   S   S
          CTA GAG ACA ACC ATG AGG TCC CCG GTG TTC ACG GAT AAC TCC TCT
```

*FIG. 3A*

```
                                        200
  P    P    V    V    P    Q    S    F    Q    V    A    H    L    H    A
 CCA  CCA  GTA  GTG  CCC  CAG  AGC  TTC  CAG  GTG  GCT  CAC  CTC  CAT  GCT 210                                              220
  P    T    G    S    G    K    S    T    K    V    P    A    A    Y    A
 CCC  ACA  GGC  AGC  GGC  AAA  AGC  ACC  AAG  GTC  CCG  GCT  GCA  TAT  GCA

230
  A    Q    G    Y    K    V    L    V    L    N    P    S    V    A    A
 GCT  CAG  GGC  TAT  AAG  GTG  CTA  GTA  CTC  AAC  CCC  TCT  GTT  GCT  GCA 240                                              250
  T    L    G    F    G    A    Y    M    S    K    A    H    G    I    D
 ACA  CTG  GGC  TTT  GGT  GCT  TAC  ATG  TCC  AAG  GCT  CAT  GGG  ATC  GAT

260
  P    N    I    R    T    G    V    R    T    I    T    T    G    S    P
 CCT  AAC  ATC  AGG  ACC  GGG  GTG  AGA  ACA  ATT  ACC  ACT  GGC  AGC  CCC 270                                              280
  I    T    Y    S    T    Y    G    K    F    L    A    D    G    G    C
 ATC  ACG  TAC  TCC  ACC  TAC  GGC  AAG  TTC  CTT  GCC  GAC  GGC  GGG  TGC

290
  S    G    G    A    Y    D    I    I    I    C    D    E    C    H    S
 TCG  GGG  GGC  GCT  TAT  GAC  ATA  ATA  ATT  TGT  GAC  GAG  TGC  CAC  TCC 300                                              310
  T    D    A    T    S    I    L    G    I    G    T    V    L    D    Q
 ACG  GAT  GCC  ACA  TCC  ATC  TTG  GGC  ATT  GGC  ACT  GTC  CTT  GAC  CAA

320
  A    E    T    A    G    A    R    L    V    V    L    A    T    A    T
 GCA  GAG  ACT  GCG  GGG  GCG  AGA  CTG  GTT  GTG  CTC  GCC  ACC  GCC  ACC 330                                              340
  P    P    G    S    V    T    V    P    H    P    N    I    E    E    V
 CCT  CCG  GGC  TCC  GTC  ACT  GTG  CCC  CAT  CCC  AAC  ATC  GAG  GAG  GTT

350
  A    L    S    T    T    G    E    I    P    F    Y    G    K    A    I
 GCT  CTG  TCC  ACC  ACC  GGA  GAG  ATC  CCT  TTT  TAC  GGC  AAG  GCT  ATC 360                                              370
  P    L    E    V    I    K    G    G    R    H    L    I    F    C    H
 CCC  CTC  GAA  GTA  ATC  AAG  GGG  GGG  AGA  CAT  CTC  ATC  TTC  TGT  CAT

380
  S    K    K    K    C    D    E    L    A    A    K    L    V    A    L
 TCA  AAG  AAG  AAG  TGC  GAC  GAA  CTC  GCC  GCA  AAG  CTG  GTC  GCA  TTG
```

*FIG. 3B*

```
              390                                               400
  G   I   N   A   V   A   Y   Y   R   G   L   D   V   S   V
  GGC ATC AAT GCC GTG GCC TAC TAC CGC GGT CTT GAC GTG TCC GTC

410
  I   P   P   I   G   D   V   V   V   A   T   D   A   L
  ATC CCG CCC ATC GGC GAT GTT GTC GTC GTG GCA ACC GAT GCC CTC 420                                               430
  M   T   G   Y   T   G   D   F   D   S   V   I   D   C   N
  ATG ACC GGC TAT ACG GGC GAC TTC GAC TCG GTG ATA GAC TGC AAT

440
  T   C   V   T   Q   T   V   D   F   S   L   D   P   T   F
  ACG TGT GTC ACC CAG ACA GTC GAT TTC AGC CTT GAC CCT ACC TTC 450                                               460
  T   I   E   T   I   T   L   P   Q   D   A   V   S   R   T
  ACC ATT GAG ACA ATC ACG CTC CCC CAA GAT GCT GTC TCC CGC ACT

470
  Q   R   R   G   R   T   G   R   G   K   P   G   I   Y   R
  CAA CGT CGG GGC AGG ACT GGC AGG GGG AAG CCA GGC ATC TAC AGA 480                                               490
  F   V   A   P   G   E   R   P   S   G   M   F   D   S   S
  TTT GTG GCA CCG GGG GAG CGC CCC TCC GGC ATG TTC GAC TCG TCC

500
  V   L   C   E   C   Y   D   A   G   C   A   W   Y   E   L
  GTC CTC TGT GAG TGC TAT GAC GCA GGC TGT GCT TGG TAT GAG CTC 510                                               520
  T   P   A   E   T   T   V   R   L   R   A   Y   M   N   T
  ACG CCC GCC GAG ACT ACA GTT AGG CTA CGA GCG TAC ATG AAC ACC

530
  P   G   L   P   V   C   Q   D   H   L   E   F   W   E   G
  CCG GGG CTT CCC GTG TGC CAG GAC CAT CTT GAA TTT TGG GAG GGC 540                                               550
  V   F   T   G   L   T   H   I   D   A   H   F   L   S   Q
  GTC TTT ACA GGC CTC ACT CAT ATA GAT GCC CAC TTT CTA TCC CAG

560
  T   K   Q   S   G   E   N   L   P   Y   L   V   A   Y   Q
  ACA AAG CAG AGT GGG GAG AAC CTT CCT TAC CTG GTA GCG TAC CAA 570                                               580
  A   T   V   C   A   R   A   Q   A   P   P   P   S   W   D
  GCC ACC GTG TGC GCT AGG GCT CAA GCC CCT CCC CCA TCG TGG GAC
```

*FIG. 3C*

```
                                        590
 Q   M   W   K   C   L   I   R   L   K   P   T   L   H   G
CAG ATG TGG AAG TGT TTG ATT CGC CTC AAG CCC ACC CTC CAT GGG 600                                         610
 P   T   P   L   L   Y   R   L   G   A   V   Q   N   E   I
CCA ACA CCC CTG CTA TAC AGA CTG GGC GCT GTT CAG AAT GAA ATC

620
 T   L   T   H   P   V   T   K   Y   I   M   T   C   M   S
ACC CTG ACG CAC CCA GTC ACC AAA TAC ATC ATG ACA TGC ATG TCG 630                                 640
 A   D   L   E   V   V   T   S   T   W   V   L   V   G   G
GCC GAC CTG GAG GTC GTC ACG AGC ACC TGG GTG CTC GTT GGC GGC

650
 V   L   A   A   L   A   A   Y   C   L   S   T   G   C   V
GTC CTG GCT GCT TTG GCC GCG TAT TGC CTG TCA ACA GGC TGC GTG 660                                     670
 V   I   V   G   R   V   V   L   S   G   K   P   A   I   I
GTC ATA GTG GGC AGG GTC GTC TTG TCC GGG AAG CCG GCA ATC ATA

680
 P   D   R   E   V   L   Y   R   E   F   D   E   M   E   E
CCT GAC AGG GAA GTC CTC TAC CGA GAG TTC GAT GAG ATG GAA GAG

686
 C
TGC
```

*FIG. 3D*

```
  1                                         10
  M   A   T   K   A   V   C   V   L   K   G   D   G   P   V
ATG GCT ACA AAG GCT GTT TGT GTT TTG AAG GGT GAC GGC CCA GTT    45

20                                  30
  Q   G   I   I   N   F   E   Q   K   E   S   N   G   P   V
CAA GGT ATT ATT AAC TTC GAG CAG AAG GAA AGT AAT GGA CCA GTG    90

40
  K   V   W   G   S   I   K   G   L   T   E   G   L   H   G
AAG GTG TGG GGA AGC ATT AAA GGA CTG ACT GAA GGC CTG CAT GGA   135

50                                  60
  F   H   V   H   E   F   G   D   N   T   A   G   C   T   S
TTC CAT GTT CAT GAG TTT GGA GAT AAT ACA GCA GGC TGT ACC AGT   180

70
  A   G   P   H   F   N   P   L   S   T   R   G   C   N   C
GCA GGT CCT CAC TTT AAT CCT CTA TCC ACG CGT GGT TGC AAT TGC   225

80                                  90
  S   I   Y   P   G   H   I   T   G   H   R   M   A   W   K
TCT ATC TAT CCC GGC CAT ATA ACG GGT CAC CGC ATG GCA TGG AAG   270

100
  L   G   S   A   A   R   T   T   S   G   F   V   S   L   F
CTT GGT TCC GCC GCC AGA ACT ACC TCG GGC TTT GTC TCC TTG TTC   315

110                                 120
  A   P   G   A   K   Q   N   E   T   H   V   T   G   G   A
GCC CCA GGT GCC AAA CAA AAC GAA ACT CAC GTC ACG GGA GGC GCA   360

130
  A   A   R   T   T   S   G   L   T   S   L   F   S   P   G
GCC GCC CGA ACT ACG TCT GGG TTG ACC TCT TTG TTC TCC CCA GGT   405
```

FIG. 6A

```
              140                                           150
 A   S   Q   N   I   Q   L   I   T   S   T   D   N   S   S
GCC AGC CAA AAC ATT CAA TTG ATT ACT AGT ACG GAT AAC TCC TCT   450

160
 P   P   V   V   P   Q   S   F   Q   V   A   H   L   H   A
CCA CCA GTA GTG CCC CAG AGC TTC CAG GTG GCT CAC CTC CAT GCT   495

170                                           180
 P   T   G   S   G   K   S   T   K   V   P   A   A   Y   A
CCC ACA GGC AGC GGC AAA AGC ACC AAG GTC CCG GCT GCA TAT GCA   540

190
 A   Q   G   Y   K   V   L   V   L   N   P   S   V   A   A
GCT CAG GGC TAT AAG GTG CTA GTA CTC AAC CCC TCT GTT GCT GCA   585

200                                           210
 T   L   G   F   G   A   Y   M   S   K   A   H   G   I   D
ACA CTG GGC TTT GGT GCT TAC ATG TCC AAG GCT CAT GGG ATC GAT   630

220
 P   N   I   R   T   G   V   R   T   I   T   T   G   S   P
CCT AAC ATC AGG ACC GGG GTG AGA ACA ATT ACC ACT GGC AGC CCC   675

230                                           240
 I   T   Y   S   T   Y   G   K   F   L   A   D   G   G   C
ATC ACG TAC TCC ACC TAC GGC AAG TTC CTT GCC GAC GGC GGG TGC   720

250
 S   G   G   A   Y   D   I   I   I   C   D   E   C   H   S
TCG GGG GGC GCT TAT GAC ATA ATA ATT TGT GAC GAG TGC CAC TCC   765

260                                           270
 T   D   A   T   S   I   L   G   I   G   T   V   L   D   Q
ACG GAT GCC ACA TCC ATC TTG GGC ATC GGC ACT GTC CTT GAC CAA   810

280
 A   E   T   A   G   A   R   L   V   V   L   A   T   A   T
GCA GAG ACT GCG GGG GCG AGA CTG GTT GTG CTC GCC ACC GCC ACC   855

290                                           300
 P   P   G   S   V   T   V   P   H   P   N   I   E   E   V
CCT CCG GGC TCC GTC ACT GTG CCC CAT CCC AAC ATC GAG GAG GTT   900
```

FIG. 6B

```
                                        310
    A   L   S   T   T   G   E   I   P   F   Y   G   K   A   I
    GCT CTG TCC ACC ACC GGA GAG ATC CCT TTT TAC GGC AAG GCT ATC    945

320                                 330
    P   L   E   V   I   K   G   G   R   H   L   I   F   C   H
    CCC CTC GAA GTA ATC AAG GGG GGG AGA CAT CTC ATC TTC TGT CAT    990

340
    S   K   K   K   C   D   E   L   A   A   K   L   V   A   L
    TCA AAG AAG AAG TGC GAC GAA CTC GCC GCA AAG CTG GTC GCA TTG    1035

350                                 360
    G   I   N   A   V   A   Y   Y   R   G   L   D   V   S   V
    GGC ATC AAT GCC GTG GCC TAC TAC CGC GGT CTT GAC GTG TCC GTC    1080

370
    I   P   T   S   G   D   V   V   V   V   A   T   D   A   L
    ATC CCG ACC AGC GGC GAT GTT GTC GTC GTG GCA ACC GAT GCC CTC    1125

380                                 390
    M   T   G   Y   T   G   D   F   D   S   V   I   D   C   N
    ATG ACC GGC TAT ACC GGC GAC TTC GAC TCG GTG ATA GAC TGC AAT    1170

400
    T   C   A   C   S   G   K   P   A   I   I   P   D   R   E
    ACG TGT GCA TGC TCC GGG AAG CCG GCA ATC ATA CCT GAC AGG GAA    1215

410                                 420
    V   L   Y   R   E   F   D   E   M   E   E   C   S   Q   H
    GTC CTC TAC CGA GAG TTC GAT GAG ATG GAA GAG TGC TCT CAG CAC    1260

430
    L   P   Y   I   E   Q   G   M   M   L   A   E   Q   F   K
    TTA CCG TAC ATC GAG CAA GGG ATG ATG CTC GCC GAG CAG TTC AAG    1305

440                                 450
    Q   K   A   L   G   L   S   R   G   G   K   P   A   I   V
    CAG AAG GCC CTC GGC CTC TCG CGA GGG GGC AAG CCG GCA ATC GTT    1350

460
    P   D   K   E   V   L   Y   Q   Q   Y   D   E   M   E   E
    CCA GAC AAA GAG GTG TTG TAT CAA CAA TAC GAT GAG ATG GAA GAG    1395
```

FIG. 6C

```
                          470                                    480
      C   S   Q   A   A   P   Y   I   E   Q   A   Q   V   I   A
     TGC TCA CAA GCT GCC CCA TAT ATC GAA CAA GCT CAG GTA ATA GCT   1440

490
      H   Q   F   K   E   K   V   L   G   L   I   D   N   D   Q
     CAC CAG TTC AAG GAA AAA GTC CTT GGA TTG ATC GAT AAT GAT CAA   1485

500                                   510
      V   V   V   T   P   D   K   E   I   L   Y   E   A   F   D
     GTG GTT GTG ACT CCT GAC AAA GAA ATC TTA TAT GAG GCC TTT GAT   1530

520
      E   M   E   E   C   A   S   K   A   A   L   I   E   E   G
     GAG ATG GAA GAA TGC GCC TCC AAA GCC GCC CTC ATT GAG GAA GGG   1575

530                                   540
      Q   R   M   A   E   M   L   K   S   K   I   Q   G   L   L
     CAG CGG ATG GCG GAG ATG CTC AAG TCT AAG ATA CAA GGC CTC CTC   1620

550
      G   I   L   R   R   H   V   G   P   G   E   G   A   V   Q
     GGG ATA CTG CGC CGG CAC GTT GGT CCT GGC GAG GGG GCA GTG CAG   1665

560                                570
      W   M   N   R   L   I   A   F   A   S   R   G   N   H   V
     TGG ATG AAC CGG CTG ATA GCC TTC GCC TCC AGA GGG AAC CAT GTT   1710

580
      S   P   T   H   Y   V   P   S   R   S   R   R   F   A   Q
     TCC CCC ACG CAC TAC GTT CCG TCT AGA TCC CGG AGA TTC GCC CAG   1755

590                                   600
      A   L   P   V   W   A   R   P   D   Y   N   P   P   L   V
     GCC CTG CCC GTT TGG GCG CGG CCG GAC TAT AAC CCC CCG CTA GTG   1800

610
      E   T   W   K   K   P   D   Y   E   P   P   V   V   H   G
     GAG ACG TGG AAA AAG CCC GAC TAC GAA CCA CCT GTG GTC CAC GGC   1845

620                                   630
      R   S   S   R   R   F   A   Q   A   L   P   V   W   A   R
     AGA TCT TCT CGG AGA TTC GCC CAG GCC CTG CCC GTT TGG GCG CGG   1890

FIG. 6D
```

```
                                                640
   P    D    Y    N    P    P    L    V    E    T    W    K    K    P    D
  CCG  GAC  TAT  AAC  CCC  CCG  CTA  GTG  GAG  ACG  TGG  AAA  AAG  CCC  GAC   1935

650                                                     660
   Y    E    P    P    V    V    H    G    R    K    T    K    R    N    T
  TAC  GAA  CCA  CCT  GTG  GTC  CAT  GGC  AGA  AAG  ACC  AAA  CGT  AAC  ACC   1980

670
   N    R    R    P    Q    D    V    K    F    P    G    G    Q    I
  AAC  CGG  CGG  CCG  CAG  GAC  GTC  AAG  TTC  CCG  GGT  GGC  GGT  CAG  ATC   2025

680                                           690
   V    G    G    V    Y    L    L    P    R    R    G    P    R    L    G
  GTT  GGT  GGA  GTT  TAC  TTG  TTG  CCG  CGC  AGG  GGC  CCT  AGA  TTG  GGT   2070

700
   V    L    A    T    R    K    T    S    P    I    P    K    A    R    R
  GTG  CTC  GCG  ACG  AGA  AAG  ACT  TCC  CCT  ATC  CCC  AAG  GCT  CGT  CGG   2115

710                                           720
   P    E    G    R    T    W    A    Q    P    G    Y    P    W    P    L
  CCC  GAG  GGC  AGG  ACC  TGG  GCT  CAG  CCC  GGT  TAC  CCT  TGG  CCC  CTC   2160

730
   Y    G    N    K    D    R    R    S    T    G    K    S    W    G    K
  TAT  GGC  AAT  AAG  GAC  AGA  CGG  TCT  ACA  GGT  AAG  TCC  TGG  GGT  AAG   2205

740                                           750
   P    G    Y    P    W    P    R    K    T    K    R    N    T    N    R
  CCA  GGG  TAC  CCT  TGG  CCA  AGA  AAG  ACC  AAA  CGT  AAC  ACC  AAC  CGG   2250

760
   R    P    Q    D    V    K    F    P    G    G    Q    I    V    G
  CGG  CCG  CAG  GAC  GTC  AAG  TTC  CCG  GGT  GGC  GGT  CAG  ATC  GTT  GGT   2295

770                                           780
   G    V    Y    L    L    P    R    R    G    P    R    L    G    V    L
  GGA  GTT  TAC  TTG  TTG  CCG  CGC  AGG  GGC  CCT  AGA  TTG  GGT  GTG  CTC   2340

790
   A    T    R    K    T    S    P    I    P    K    A    R    R    P    E
  GCG  ACG  AGA  AAG  ACT  TCC  CCT  ATC  CCC  AAG  GCT  CGT  CGG  CCC  GAG   2385
```

FIG. 6E

```
        800                                                810
G   R   T   W   A   Q   P   G   Y   P   W   P   L   Y   G
GGC AGG ACC TGG GCT CAG CCC GGT TAC CCT TGG CCC CTC TAT GGC    2430

820
N   K   D   R   R   S   T   G   K   S   W   G   K   P   G
AAT AAG GAC AGA CGG TCT ACA GGT AAG TCC TGG GGT AAG CCA GGG    2475

829
Y   P   W   P   OC
TAC CCT TGG CCC TAA TGAGTCGAC
```

FIG. 6F

```
  1                                              10
  M   A   T   K   A   V   C   V   L   K   G   D   G   P   V
ATG GCT ACA AAG GCT GTT TGT GTT TTG AAG GGT GAC GGC CCA GTT 20                                  30
  Q   G   I   I   N   F   E   Q   K   E   S   N   G   P   V
CAA GGT ATT ATT AAC TTC GAG CAG AAG GAA AGT AAT GGA CCA GTG

40
  K   V   W   G   S   I   K   G   L   T   E   G   L   H   G
AAG GTG TGG GGA AGC ATT AAA GGA CTG ACT GAA GGC CTG CAT GGA 50                                  60
  F   H   V   H   E   F   G   D   N   T   A   G   C   T   S
TTC CAT GTT CAT GAG TTT GGA GAT AAT ACA GCA GGC TGT ACC AGT

70
  A   G   P   H   F   N   P   L   S   R   K   H   G   G   P
GCA GGT CCT CAC TTT AAT CCT CTA TCC AGA AAA CAC GGT GGG CCA 80                                  90
  K   D   E   E   R   H   V   G   D   L   G   N   V   T   A
AAG GAT GAA GAG AGG CAT GTT GGA GAC TTG GGC AAT GTG ACT GCT

100
  D   K   D   G   V   A   D   V   S   I   E   D   S   V   I
GAC AAA GAT GGT GTG GCC GAT GTG TCT ATT GAA GAT TCT GTG ATC 110                                 120
  S   L   S   G   D   H   C   I   I   G   R   T   L   V   V
TCA CTC TCA GGA GAC CAT TGC ATC ATT GGC CGC ACA CTG GTG GTC

130
  H   E   K   A   D   D   L   G   K   G   G   N   E   E   S
CAT GAA AAA GCA GAT GAC TTG GGC AAA GGT GGA AAT GAA GAA AGT 140                                 150
  T   K   T   G   N   A   G   S   R   L   A   C   G   V   I
ACA AAG ACA GGA AAC GCT GGA AGT CGT TTG GCT TGT GGT GTA ATT

160
  G   I   A   Q   N   L   N   S   G   C   N   C   S   I   Y
GGG ATC GCC CAG AAT TTG AAT TCT GGT TGC AAT TGC TCT ATC TAT 170                                 180
  P   G   H   I   T   G   H   R   M   A   W   K   L   G   S
CCC GGC CAT ATA ACG GGT CAC CGC ATG GCA TGG AAG CTT GGT TCC

190
  A   A   R   T   T   S   G   F   V   S   L   F   A   P   G
GCC GCC AGA ACT ACC TCG GGC TTT GTC TCC TTG TTC GCC CCA GGT
```

*FIG. 8A*

```
            200                                              210
  A   K   Q   N   E   T   H   V   T   G   G   A   A   A   R
 GCC AAA CAA AAC GAA ACT CAC GTC ACG GGA GGC GCA GCC GCC CGA

220
  T   T   S   G   L   T   S   L   F   S   P   G   A   S   Q
 ACT ACG TCT GGG TTG ACC TCT TTG TTC TCC CCA GGT GCC AGC CAA 230                                          240
  N   I   Q   L   I   V   D   F   I   P   V   E   N   L   E
 AAC ATT CAA TTG ATT GTC GAC TTT ATC CCT GTG GAG AAC CTA GAG

250
  T   T   M   R   S   P   V   F   T   D   N   S   P   P
 ACA ACC ATG CGA TCT CCG GTG TTC ACG GAT AAC TCC TCT CCA CCA 260                                              270
  V   V   P   Q   S   F   Q   V   A   H   L   H   A   P   T
 GTA GTG CCC CAG AGC TTC CAG GTG GCT CAC CTC CAT GCT CCC ACA

280
  G   S   G   K   S   T   K   V   P   A   A   Y   A   A   Q
 GGC AGC GGC AAA AGC ACC AAG GTC CCG GCT GCA TAT GCA GCT CAG 290                                          300
  G   Y   K   V   L   V   L   N   P   S   V   A   A   T   L
 GGC TAT AAG GTG CTA GTA CTC AAC CCC TCT GTT GCT GCA ACA CTG

310
  G   F   G   A   Y   M   S   K   A   H   G   I   D   P   N
 GGC TTT GGT GCT TAC ATG TCC AAG GCT CAT GGG ATC GAT CCT AAC 320                                              330
  I   R   T   G   V   R   T   I   T   T   G   S   P   I   T
 ATC AGG ACC GGG GTG AGA ACA ATT ACC ACT GGC AGC CCC ATC ACG

340
  Y   S   T   Y   G   K   F   L   A   D   G   G   C   S   G
 TAC TCC ACC TAC GGC AAG TTC CTT GCC GAC GGC GGG TGC TCG GGG 350                                          360
  G   A   Y   D   I   I   I   C   D   E   C   H   S   T   D
 GGC GCT TAT GAC ATA ATA ATT TGT GAC GAG TGC CAC TCC ACG GAT

370
  A   T   S   I   L   G   I   G   T   V   L   D   Q   A   E
 GCC ACA TCC ATC TTG GGC ATT GGC ACT GTC CTT GAC CAA GCA GAG 380                                          390
  T   A   G   A   R   L   V   V   L   A   T   A   T   P   P
 ACT GCG GGG GCG AGA CTG GTT GTG CTC GCC ACC GCC ACC CCT CCG

400
  G   S   V   T   V   P   H   P   N   I   E   E   V   A   L
 GGC TCC GTC ACT GTG CCC CAT CCC AAC ATC GAG GAG GTT GCT CTG 410                                              420
```

FIG. 8B

```
  S   T   T   G   E   I   P   F   Y   G   K   A   I   P   L
TCC ACC ACC GGA GAG ATC CCT TTT TAC GGC AAG GCT ATC CCC CTC
                                430
  E   V   I   K   G   G   R   H   L   I   F   C   H   S   K
GAA GTA ATC AAG GGG GGA AGA CAT CTC ATC TTC TGT CAT TCA AAG
              440                                   450
  K   K   C   D   E   L   A   A   K   L   V   A   L   G   I
AAG AAG TGC GAC GAA CTC GCC GCA AAG CTG GTC GCA TTG GGC ATC
                              460
  N   A   V   A   Y   Y   R   G   L   D   V   S   V   I   P
AAT GCC GTG GCC TAC TAC CGC GGT CTT GAC GTG TCC GTC ATC CCG
                  470                                   480
  T   S   G   D   V   V   V   V   A   T   D   A   L   M   T
ACC AGC GGC GAT GTT GTC GTC GTG GCA ACC GAT GCC CTC ATG ACC
                                490
  G   Y   T   G   D   F   D   S   V   I   D   C   N   T   C
GGC TAT ACC GGC GAC TTC GAC TCG GTG ATA GAC TGC AAT ACG TGT
              500                                   510
  V   T   Q   T   V   D   F   S   L   D   P   T   F   T   I
GTC ACC CAG ACA GTC GAT TTC AGC CTT GAC CCT ACC TTC ACC ATT
                          520
  E   T   I   T   L   P   Q   D   A   V   S   R   T   Q   R
GAG ACA ATC ACG CTC CCC CAA GAT GCT GTC TCC CGC ACT CAA CGT
              530                                   540
  R   G   R   T   G   R   G   K   P   G   I   Y   R   F   V
CGG GGC AGG ACT GGC AGG GGG AAG CCA GGC ATC TAC AGA TTT GTG
                              550
  A   P   G   E   R   P   S   G   M   F   D   S   S   V   L
GCA CCG GGG GAG CGC CCC TCC GGC ATG TTC GAC TCG TCC GTC CTC
              560                                   570
  C   E   C   Y   D   A   G   C   A   W   Y   E   L   T   P
TGT GAG TGC TAT GAC GCA GGC TGT GCT TGG TAT GAG CTC ACG CCC
                              580
  A   E   T   T   V   R   L   R   A   Y   M   N   T   P   G
GCC GAG ACT ACA GTT AGG CTA CGA GCG TAC ATG AAC ACC CCG GGG
                  590                                   600
  L   P   V   C   Q   D   H   L   E   F   W   E   G   V   F
CTT CCC GTG TGC CAG GAC CAT CTT GAA TTT TGG GAG GGC GTC TTT
                              610
  T   G   L   T   H   I   D   A   H   F   L   S   Q   T   K
ACA GGC CTC ACT CAT ATA GAT GCC CAC TTT CTA TCC CAG ACA AAG
                  620                                   630
  Q   S   G   E   N   L   P   Y   L   V   A   Y   Q   A   T
```

*FIG. 8C*

```
                CAG AGT GGG GAG AAC CTT CCT TAC CTG GTA GCG TAC CAA GCC ACC

640
     V   C   A   R   A   Q   A   P   P   P   S   W   D   Q   M
    GTG TGC GCT AGG GCT CAA GCC CCT CCC CCA TCG TGG GAC CAG ATG 650                                   660
     W   K   C   L   I   R   L   K   P   T   L   H   G   P   T
    TGG AAG TGT TTG ATT CGC CTC AAG CCC ACC CTC CAT GGG CCA ACA

670
     P   L   L   Y   R   L   G   A   V   Q   N   E   I   T   L
    CCC CTG CTA TAC AGA CTG GGC GCT GTT CAG AAT GAA ATC ACC CTG 680                                   690
     T   H   P   V   T   K   Y   I   M   T   C   M   S   A   D
    ACG CAC CCA GTC ACC AAA TAC ATC ATG ACA TGC ATG TCG GCC GAC

700
     L   E   V   V   T   S   A   C   S   G   K   P   A   I   I
    CTG GAG GTC GTC ACG AGC GCA TGC TCC GGG AAG CCG GCA ATC ATA 710                                   720
     P   D   R   E   V   L   Y   R   E   F   D   E   M   E   E
    CCT GAC AGG GAA GTC CTC TAC CGA GAG TTC GAT GAG ATG GAA GAG

730
     C   S   Q   H   L   P   Y   I   E   Q   G   M   M   L   A
    TGC TCT CAG CAC TTA CCG TAC ATC GAG CAA GGG ATG ATG CTC GCC 740                                   750
     E   Q   F   K   Q   K   A   L   G   L   S   R   G   G   K
    GAG CAG TTC AAG CAG AAG GCC CTC GGC CTC TCG CGA GGG GGC AAG

760
     P   A   I   V   P   D   K   E   V   L   Y   Q   Q   Y   D
    CCG GCA ATC GTT CCA GAC AAA GAG GTG TTG TAT CAA CAA TAC GAT 770                                   780
     E   M   E   E   C   S   Q   A   A   P   Y   I   E   Q   A
    GAG ATG GAA GAG TGC TCA CAA GCT GCC CCA TAT ATC GAA CAA GCT

790
     Q   V   I   A   H   Q   F   K   E   K   V   L   G   L   I
    CAG GTA ATA GCT CAC CAG TTC AAG GAA AAA GTC CTT GGA TTG ATC 800                                   810
     D   N   D   Q   V   V   V   T   P   D   K   E   I   L   Y
    GAT AAT GAT CAA GTG GTT GTG ACT CCT GAC AAA GAA ATC TTA TAT

820
     E   A   F   D   E   M   E   E   C   A   S   K   A   A   L
    GAG GCC TTT GAT GAG ATG GAA GAA TGC GCC TCC AAA GCC GCC CTC 830                                   840
     I   E   E   G   Q   R   M   A   E   m   L   K   S   K   I
    ATT GAG GAA GGG CAG CGG ATG GCG GAG ATG CTC AAG TCT AAG ATA
```

*FIG. 8D*

```
                                              850
         Q   G   L   L   G   I   L   R   R   H   V   G   P   G   E
        CAA GGC CTC CTC GGG ATA CTG CGC CGG CAC GTT GGT CCT GGC GAG 860                                 870
         G   A   V   Q   W   M   N   R   L   I   A   F   A   S   R
        GGG GCA GTG CAG TGG ATG AAC CGG CTG ATA GCC TTC GCC TCC AGA

880
         G   N   H   V   S   P   T   H   Y   V   P   S   R   S   R
        GGG AAC CAT GTT TCC CCC ACG CAC TAC GTT CCG TCT AGA TCC CGG 890                                 900
         R   F   A   Q   A   L   P   V   W   A   R   P   D   Y   N
        AGA TTC GCC CAG GCC CTG CCC GTT TGG GCG CGG CCG GAC TAT AAC

910
         P   P   L   V   E   T   W   K   K   P   D   Y   E   P   P
        CCC CCG CTA GTG GAG ACG TGG AAA AAG CCC GAC TAC GAA CCA CCT 920                                 930
         V   V   H   G   R   S   S   R   R   F   A   Q   A   L   P
        GTG GTC CAC GGC AGA TCT TCT CGG AGA TTC GCC CAG GCC CTG CCC

940
         V   W   A   R   P   D   Y   N   P   P   L   V   E   T   W
        GTT TGG GCG CGG CCG GAC TAT AAC CCC CCG CTA GTG GAG ACG TGG 950                                 960
         K   K   P   D   Y   E   P   P   V   V   H   G   R   K   T
        AAA AAG CCC GAC TAC GAA CCA CCT GTG GTC CAT GGC AGA AAG ACC

970
         K   R   N   T   N   R   R   P   Q   D   V   K   F   P   G
        AAA CGT AAC ACC AAC CGG CGG CCG CAG GAC GTC AAG TTC CCG GGT 980                                 990
         G   G   Q   I   V   G   R   R   G   P   P   I   P   K   A
        GGC GGT CAG ATC GTT GGT CGC AGG GGC CCT CCT ATC CCC AAG GCT

1000
         R   R   P   E   G   R   T   W   A   Q   P   G   Y   P   W
        CGT CGG CCC GAG GGC AGG ACC TGG GCT CAG CCC GGT TAC CCT TGG 1010                                1020
         P   L   Y   G   N   K   D   R   R   S   T   G   K   S   W
        CCC CTC TAT GGC AAT AAG GAC AGA CGG TCT ACA GGT AAG TCC TGG

1030
         G   K   P   G   Y   P   W   P   R   K   T   K   R   N   T
        GGT AAG CCA GGG TAC CCT TGG CCA AGA AAG ACC AAA CGT AAC ACC 1040                                1050
         N   R   R   P   Q   D   V   K   F   P   G   G   G   Q   I
        AAC CGA CGG CCG CAG GAC GTC AAG TTC CCG GGT GGC GGT CAG ATC
```

*FIG. 8E*

```
                                       1060
V    G    R    R    G    P    P    I    P    K    A    R    R    P    E
GTT  GGT  CGC  AGG  GGC  CCT  CCT  ATC  CCC  AAG  GCT  CGT  CGG  CCC  GAG 1070                                       1080
G    R    T    W    A    Q    P    G    Y    P    W    P    L    Y    G
GGC  AGG  ACC  TGG  GCT  CAG  CCC  GGT  TAC  CCT  TGG  CCC  CTC  TAT  GGC

1090
N    K    D    R    R    S    T    G    K    S    W    G    K    P    G
AAT  AAG  GAC  AGA  CGG  TCT  ACC  GGT  AAG  TCC  TGG  GGT  AAG  CCA  GGG

1099
Y    P    W    P
TAT  CCT  TGG  CCC
```

A — MEFA-3 ANTIGEN

| hSOD-(1-154) | CORE | c33c | 5-1-1 type 1 | 5-1-1 type 3 | 5-1-1 type 2 | C-100 | NS5 |
|---|---|---|---|---|---|---|---|
| 10–53 | 10–53 | 1192–1457 | 1694–1735 | 1694–1735 | 1694–1735 | 1901–1940 | 2278–2310 |

AMINO ACIDS

B — MEFA-5 ANTIGEN

| hSOD-(1-154) | CORE | E1 | E2 | c33c | 5-1-1 type 1 | 5-1-1 type 3 | 5-1-1 type 2 | C-100 | NS5 |
|---|---|---|---|---|---|---|---|---|---|
| 10–53 | 10–53 | 303–320 | 405–444 | 1192–1457 | 1689–1735 | 1689–1735 | 1689–1735 | 1901–1940 | 2278–2313 |

AMINO ACIDS

C — MEFA-6 ANTIGEN

| hSOD-(1-154) | E1 | E2 | c33c | 5-1-1 type 1 | 5-1-1 type 3 | 5-1-1 type 2 | C-100 | NS5 | NS5 | CORE | CORE |
|---|---|---|---|---|---|---|---|---|---|---|---|
| 303–320 | 405–444 | 1192–1457 | 1689–1735 | 1689–1735 | 1689–1735 | 1901–1940 | 2278–2313 | 2278–2313 | 10–53 | 10–53 |

AMINO ACIDS

HCV ASSAY

CROSS-REFERENCE TO RELATED APPLICATION

This application is related to provisional application No. 60/409,515, filed Sep. 9, 2002, from which priority is claimed under 35 USC §119(e)(1) and which application is incorporated herein by reference in its entirety.

TECHNICAL FIELD

The present invention pertains generally to viral diagnostics. In particular, the invention relates to antigen/antibody/antigen sandwich assays utilizing a first isolated antigen derived from a region of the hepatitis C virus polyprotein and a multiple epitope fusion antigen including multiple epitopes from the HCV polyprotein, which multiple epitopes include one or more epitopes from the same region of the polyprotein as the first antigen, for accurately diagnosing hepatitis C virus infection.

BACKGROUND OF THE INVENTION

Hepatitis C Virus (HCV) is the principal cause of parenteral non-A, non-B hepatitis (NANBH) which is transmitted largely through blood transfusion and sexual contact. The virus is present in 0.4 to 2.0% of blood donors. Chronic hepatitis develops in about 50% of infections and of these, approximately 20% of infected individuals develop liver cirrhosis which sometimes leads to hepatocellular carcinoma. Accordingly, the study and control of the disease is of medical importance.

HCV was first identified and characterized as a cause of NANBH by Houghten et al. The viral genomic sequence of HCV is known, as are methods for obtaining the sequence. See, e.g., International Publication Nos. WO 89/04669; WO 90/11089; and WO 90/14436. HCV has a 9.5 kb positive-sense, single-stranded RNA genome and is a member of the Flaviridae family of viruses. At least six distinct, but related genotypes of HCV, based on phylogenetic analyses, have been identified (Simmonds et al., *J. Gen. Virol.* (1993) 74:2391–2399). The virus encodes a single polyprotein having more than 3000 amino acid residues (Choo et al., *Science* (1989) 244:359–362; Choo et al., *Proc. Natl. Acad. Sci. USA* (1991) 88:2451–2455; Han et al., *Proc. Natl. Acad. Sci. USA* (1991) 88:1711–1715). The polyprotein is processed co- and post-translationally into both structural and non-structural (NS) proteins.

In particular, as shown in FIG. 1, several proteins are encoded by the HCV genome. The order and nomenclature of the cleavage products of the HCV polyprotein is as follows: $NH_2$—C-E1-E2-p7-NS2-NS3-NS4a-NS4b-NS5a-NS5b-COOH. Initial cleavage of the polyprotein is catalyzed by host proteases which liberate three structural proteins, the N-terminal nucleocapsid protein (termed "core") and two envelope glycoproteins, AE1" (also known as E) and AE2" (also known as E2/NS1), as well as nonstructural (NS) proteins that contain the viral enzymes. The NS regions are termed NS2, NS3, NS4 and NS5. NS2 is an integral membrane protein with proteolytic activity and, in combination with NS3, cleaves the NS2–NS3 sissle bond which in turn generates the NS3 N-terminus and releases a large polyprotein that includes both serine protease and RNA helicase activities. The NS3 protease serves to process the remaining polyprotein. In these reactions, NS3 liberates an NS3 cofactor (NS4a), two proteins (NS4b and NS5a), and an RNA-dependent RNA polymerase (NS5b). Completion of polyprotein maturation is initiated by autocatalytic cleavage at the NS3–NS4a junction, catalyzed by the NS3 serine protease.

A number of general and specific polypeptides useful as immunological and diagnostic reagents for HCV, derived from the HCV polyprotein, have been described. See, e.g., Houghton et al., European Publication Nos. 318,216 and 388,232; Choo et al., *Science* (1989) 244:359–362; Kuo et al., *Science* (1989) 244:362–364; Houghton et al., *Hepatology* (1991) 14:381–388; Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778. These publications provide an extensive background on HCV generally, as well as on the manufacture and uses of HCV polypeptide immunological reagents. For brevity, therefore, the disclosure of these publications is incorporated herein by reference.

Sensitive, specific methods for screening and identifying carriers of HCV and HCV-contaminated blood or blood products would provide an important advance in medicine. Post-transfusion hepatitis (PTH) occurs in approximately 10% of transfused patients, and HCV has accounted for up to 90% of these cases. Patient care as well as the prevention and transmission of HCV by blood and blood products or by close personal contact require reliable diagnostic and prognostic tools. Accordingly, several assays have been developed for the serodiagnosis of HCV infection. See, e.g., Choo et al., *Science* (1989) 244:359–362; Kuo et al., *Science* (1989) 244:362–364; Choo et al., *Br. Med. Bull.* (1990) 46:423–441; Ebeling et al., *Lancet* (1990) 335:982–983; van der Poel et al., *Lancet* (1990) 335:558–560; van der Poel et al., *Lancet* (1991) 337:317–319; Chien, D. Y., International Publication No. WO 94/01778; Valenzuela et al., International Publication No. WO 97/44469; and Kashiwakuma et al., U.S. Pat. No. 5,871,904.

A significant problem encountered with some serum-based assays is that there is a significant gap between infection and detection of the virus, often exceeding 80 days. This assay gap may create great risk for blood transfusion recipients. To overcome this problem, nucleic acid-based tests (NAT) that detect viral RNA directly, and HCV core antigen tests that assay viral antigen instead of antibody response, have been developed. See, e.g., Kashiwakuma et al., U.S. Pat. No. 5,871,904; Beld et al., *Transfusion* (2000) 40:575–579.

However, there remains a need for sensitive, accurate diagnostic and prognostic tools in order to provide adequate patient care as well as to prevent transmission of HCV by blood and blood products or by close personal contact.

SUMMARY OF THE INVENTION

The present invention is based in part, on the finding that the use of a first antigen derived from the HCV polyprotein, in combination with a multiple epitope fusion antigen that includes an epitope from the same region of the HCV polyprotein as the first antigen, provides a sensitive and reliable method for detecting HCV. The assays described herein can detect HCV infection caused by any of the six known genotypes of HCV. In one representative embodiment of the invention, the first antigen includes an NS3/4a conformational epitope and the second antigen is a multiple epitope fusion antigen that includes one or more epitopes from the NS3/4a region. The use of multiple epitope fusion proteins decreases masking problems, improves sensitivity and detects antibodies by providing a greater number of epitopes on a unit area of substrate and improving selectivity. Moreover, the assays described herein can be performed quickly and greater sample volumes can be used without background effects.

Accordingly, in one embodiment, the subject invention is directed to a method of detecting hepatitis C virus (HCV) infection in a biological sample. The method comprises:

(a) providing an immunoassay solid support comprising HCV antigens bound thereto, wherein the HCV antigens consist of one or more isolated antigens from a first region of the HCV polyprotein;

(b) combining a biological sample with the solid support under conditions which allow HCV antibodies, when present in the biological sample, to bind to the one or more HCV antigens;

(c) adding to the solid support from step (b) under complex-forming conditions a detectably labeled HCV multiple epitope fusion antigen (MEFA), wherein the labeled MEFA comprises at least one epitope from the same region of the HCV polyprotein as the one or more isolated antigens, wherein the MEFA binds the bound HCV antibody;

(d) detecting complexes formed between the HCV antibody and the one or more antigens from the first region of the HCV polyprotein and said MEFA, if any, as an indication of HCV infection in the biological sample.

In another embodiment, the invention pertains to a method of detecting HCV infection in a biological sample. The method comprises:

(a) providing an immunoassay solid support comprising HCV antigens bound thereto, wherein the HCV antigens consist of one or more multiple epitope fusion antigens (MEFAs);

(b) combining a biological sample with the solid support under conditions which allow HCV antibodies, when present in the biological sample, to bind to the one or more MEFAs;

(c) adding to the solid support from step (b) under complex-forming conditions a detectably labeled isolated HCV antigen from a region of the HCV polyprotein present in the one or more MEFAs, wherein the isolated antigen binds the bound HCV antibody;

(d) detecting complexes formed between the HCV antibody and the isolated HCV antigen and said MEFA, if any, as an indication of HCV infection in the biological sample.

In still a further embodiment, the invention pertains to a method of detecting HCV infection in a biological sample. The method comprises:

(a) providing an immunoassay solid support comprising HCV antigens bound thereto, wherein the HCV antigens consist of one or more isolated HCV NS3/4a conformational epitopes;

(b) combining a biological sample with the solid support under conditions which allow HCV antibodies, when present in the biological sample, to bind to the one or more NS3/4a epitopes;

(c) adding to the solid support from step (b) under complex-forming conditions a detectably labeled HCV multiple epitope fusion antigen (MEFA), wherein the labeled MEFA comprises at least one epitope from the HCV NS3/4a region, wherein the MEFA binds the bound HCV antibody;

(d) detecting complexes formed between the HCV antibody and the NS3/4a conformational epitope and the MEFA, if any, as an indication of HCV infection in the biological sample.

In another embodiment, the invention pertains to a method of detecting HCV infection in a biological sample. The method comprises:

(a) providing an immunoassay solid support comprising HCV antigens bound thereto, wherein the HCV antigens consist of one or more multiple epitope fusion antigens (MEFAs) wherein the one or more MEFAs comprise at least one epitope from the HCV NS3/4a region;

(b) combining a biological sample with the solid support under conditions which allow HCV antibodies, when present in the biological sample, to bind to the one or more MEFAs;

(c) adding to the solid support from step (b) under complex-forming conditions a detectably labeled HCV NS3/4a conformational epitope, wherein the NS3/4a conformational epitope binds the bound HCV antibody;

(d) detecting complexes formed between the HCV antibody and the NS3/4a conformational epitope and the MEFA, if any, as an indication of HCV infection in the biological sample.

In the above methods, the NS3/4a conformational epitope and/or the MEFA comprises an epitope from the NS3/4a protease region of the HCV polyprotein and/or an epitope from the NS3/4a helicase region of the HCV polyprotein. In particular embodiments, the NS3/4a conformational epitope comprises the amino acid sequence depicted in FIGS. 3A–3D (SEQ ID NOS:1 and 2).

In additional embodiments, the MEFA comprises amino acids 1193–1657, numbered relative to the HCV-1 sequence. In yet further embodiments, the MEFA comprises an epitope from the c33c region of the HCV polyprotein, such as amino acids 1211–1457 and/or amino acids 1192–1457, numbered relative to HCV-1.

In further embodiments, the MEFA comprises an epitope from the 5-1-1 region of the HCV polyprotein, such as amino acids 1689–1735, numbered relative to HCV-1.

In particular embodiments, the MEFA comprises the amino acid sequence depicted in FIGS. 6A–6F (SEQ ID NOS:3 and 4) or the amino acid sequence depicted in FIGS. 8A–8F (SEQ ID NOS:5 and 6).

These and other aspects of the present invention will become evident upon reference to the following detailed description and attached drawings. In addition, various references are set forth herein which describe in more detail certain procedures or compositions, and are therefore incorporated by reference in their entirety.

BRIEF DESCRIPTION OF THE DRAWINGS

FIGS. 3A through 3D (SEQ ID NOS:1 and 2) depict the DNA and corresponding amino acid sequence of a representative NS3/4a conformational antigen for use in the present assays. The amino acids at positions 403 and 404 of FIGS. 3A through 3D represent substitutions of Pro for Thr, and Ile for Ser, of the native amino acid sequence of HCV-1.

FIGS. 6A–6F (SEQ ID NOS:3 and 4) depict the DNA and corresponding amino acid sequence of MEFA 12.

FIGS. 8A–8F (SEQ ID NOS:5 and 6) depict the DNA and corresponding amino acid sequence of MEFA 7.1.

FIGS. 9A–9C show representative MEFAs for use with the subject immunoassays. FIG. 9A is a diagrammatic representation of MEFA 3. FIG. 9B is a diagrammatic representation of MEFA 5. FIG. 9C is a diagrammatic representation of MEFA 6.

DETAILED DESCRIPTION OF THE INVENTION

Figure 1:
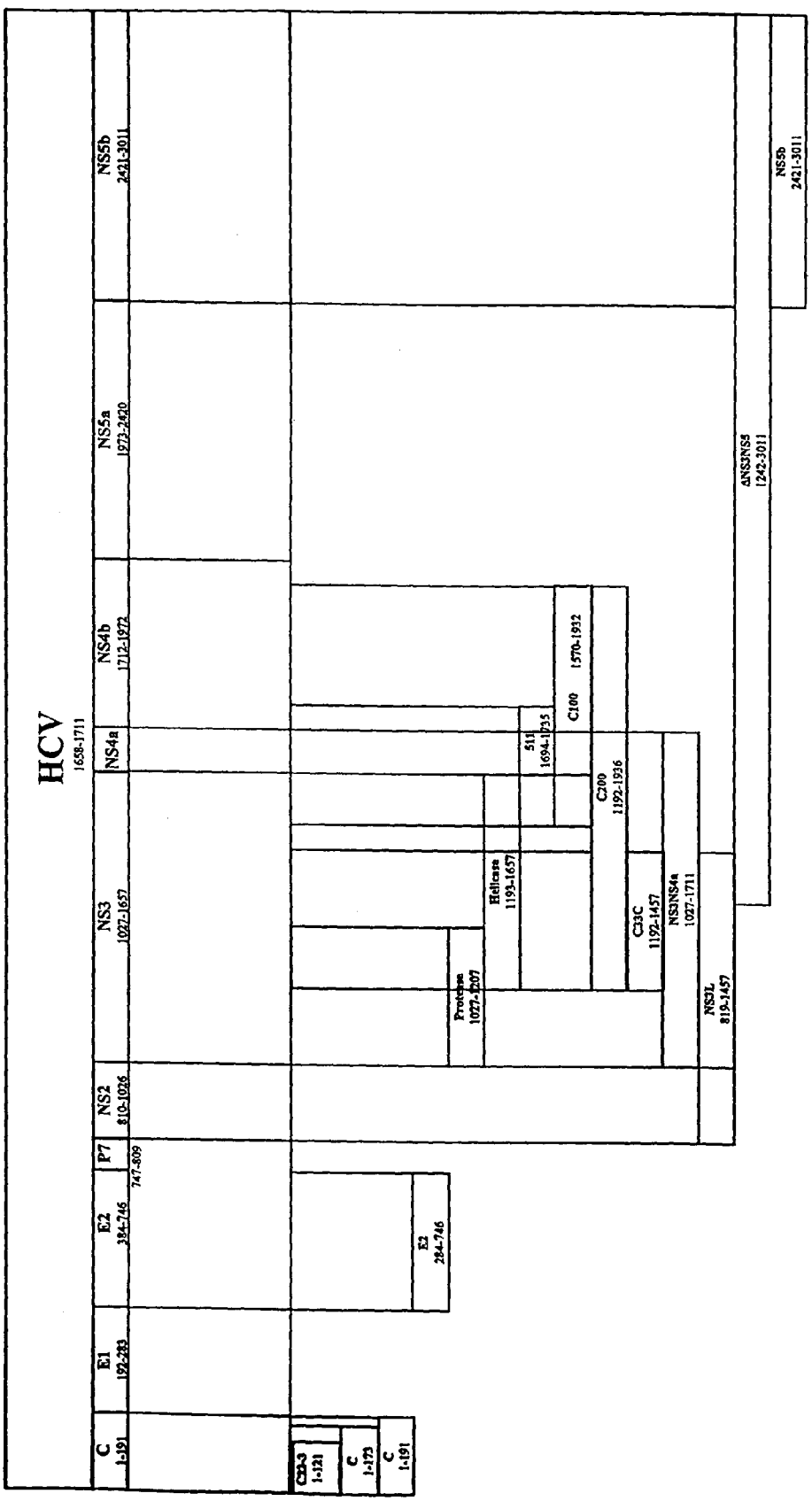
FIG. 1 is a diagrammatic representation of the HCV genome, depicting the various regions of the polyprotein from which the present assay reagents (proteins and antibodies) are derived.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology*, 2nd Edition, vol. I & II (B. N. Fields and D. M. Knipe, eds.); *Handbook of Experimental Immunology*, Vols. I–IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. DEFINITIONS

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. The polypeptide need not be physically derived from HCV, but may be synthetically or recombinantly produced. Moreover, the polypeptide may be derived from any of the various HCV strains and isolates, such as, but not limited to, any of the isolates from strains 1, 2, 3, 4, 5 or 6 of HCV. A number of conserved and variable regions are known between these strains and, in general, the amino acid sequences of epitopes derived from these regions will have a high degree of sequence homology, e.g., amino acid sequence homology of more than 30%, preferably more than 40%, when the two sequences are aligned. Thus, for example, the term "NS3/4a" polypeptide refers to native NS3/4a from any of the various HCV strains, as well as NS3/4a analogs, muteins and immunogenic fragments, as defined further below. The complete genotypes of many of these strains are known. See, e.g., U.S. Pat. No. 6,150,087 and GenBank Accession Nos. AJ238800 and AJ238799.

The terms "analog" and "mutein" refer to biologically active derivatives of the reference molecule, or fragments of such derivatives, that retain desired activity, such as immunoreactivity in the assays described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publication No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5–10 conservative or non-conservative amino acid substitutions, or even up to about 15–25 conservative or non-conservative amino acid substitutions, or any integer between 5–25, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" of a particular HCV protein will generally include at least about 5–10 contiguous amino acid residues of the full-length molecule, preferably at least about 15–25 contiguous amino acid residues of the full-length molecule, and most preferably at least about 20–50 or more contiguous amino acid residues of the full-length molecule, that define an epitope, or any integer between 5 amino acids and the fill-length sequence, provided that the fragment in question retains immunoreactivity in the assays described herein. For example, preferred immunogenic fragments for use in the MEFAs, include but are not limited to fragments of HCV core that comprise, e.g., amino acids 10–45, 10–53, 67–88, and 120–130 of the polyprotein, epitope 5-1-1 (in the NS3 region of the viral genome) as well as defined epitopes derived from the E1, E2, c33c (NS3), c100 (NS4), NS3/4a and NS5 regions of the HCV polyprotein, as well as any of the other various epitopes identified from the HCV polyprotein. See, e.g., Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; U.S. Pat. Nos. 6,150,087 and 6,121,020, all of which are incorporated by reference herein.

The term "epitope" as used herein refers to a sequence of at least about 3 to 5, preferably about 5 to 10 or 15, and not more than about 1,000 amino acids (or any integer therebetween), which define a sequence that by itself or as part of a larger sequence, binds to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1985) *Proc. Natl. Acad. Sci. USA* 82:178–182; Geysen et al. (1986) *Molec. Immunol.* 23:709–715, all incorporated herein by reference in their entireties. Using such techniques, a number of epitopes of HCV have been identified. See, e.g., Chien et al., *Viral Hepatitis and Liver Disease* (1994) pp. 320–324, and further below. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824–3828 for determining antigenicity profiles, and the Kyte-Doolittle technique, Kyte et al., *J. Mol. Biol.* (1982) 157:105–132 for hydropathy plots.

For a description of various HCV epitopes, see, e.g., Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; and U.S. Pat. Nos. 6,280,927 and 6,150,087, incorporated herein by reference in their entireties.

As used herein, the term "conformational epitope" refers to a portion of a full-length protein, or an analog or mutein thereof, having structural features native to the amino acid sequence encoding the epitope within the full-length natural protein. Native structural features include, but are not limited to, glycosylation and three dimensional structure. The length of the epitope-defining sequence can be subject to wide variations as these epitopes are believed to be formed by the three-dimensional shape of the antigen (e.g., folding). Thus, amino acids defining the epitope can be relatively few in number, but widely dispersed along the length of the molecule (or even on different molecules in the case of dimers, etc.), being brought into correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g., cysteines involved in disulfide bonding, glycosylation sites, etc.).

Conformational epitopes present in, e.g., the NS3/4a region are readily identified using methods discussed above. Moreover, the presence or absence of a conformational epitope in a given polypeptide can be readily determined through screening the antigen of interest with an antibody (polyclonal serum or monoclonal to the conformational epitope) and comparing its reactivity to that of a denatured version of the antigen which retains only linear epitopes (if any). In such screening using polyclonal antibodies, it may be advantageous to absorb the polyclonal serum first with the denatured antigen and see if it retains antibodies to the antigen of interest. Additionally, in the case of NS3/4a, a molecule which preserves the native conformation will also have protease and, optionally, helicase enzymatic activities. Such activities can be detected using enzymatic assays, as described further below.

Preferably, a conformational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publication Nos. WO 96/04301, WO 94/01778, WO 95/33053, WO 92/08734, which applications are incorporated by reference herein in their entireties. Alternatively, it is possible to express the antigens and further renature the protein after recovery. It is also understood that chemical synthesis may also provide conformational antigen mimitopes that cross-react with the "native" antigen's conformational epitope.

The term "multiple epitope fusion antigen" or "MEFA" as used herein intends a polypeptide in which multiple HCV antigens are part of a single, continuous chain of amino acids, which chain does not occur in nature. The HCV antigens may be connected directly to each other by peptide bonds or may be separated by intervening amino acid sequences. The fusion antigens may also contain sequences exogenous to the HCV polyprotein. Moreover, the HCV sequences present may be from multiple genotypes and/or isolates of HCV. Examples of particular MEFAs for use in the present immunoassays are detailed in, e.g., International Publication Nos. WO 01/96875, WO 01/09609, WO 97/44469 and U.S. Pat. Nos. 6,514,731 and 6,428,792, incorporated herein by reference in their entireties.

An "antibody" intends a molecule that, through chemical or physical means, specifically binds to a polypeptide of interest. Thus, an HCV NS3/4a antibody is a molecule that specifically binds to an epitope of an HCV NS3/4a protein. The term "antibody" as used herein includes antibodies obtained from both polyclonal and monoclonal preparations, as well as, the following: hybrid (chimeric) antibody molecules (see, for example, Winter et al. (1991) Nature 349: 293–299; and U.S. Pat. No. 4,816,567); F(ab')2 and F(ab) fragments; Fv molecules (non-covalent heterodimers, see, for example, Inbar et al. (1972) *Proc Natl Acad Sci USA* 69:2659–2662; and Ehrlich et al. (1980) *Biochem* 19:4091–4096); single-chain Fv molecules (sFv) (see, for example, Huston et al. (1988) *Proc Natl Acad Sci USA* 85:5879–5883); dimeric and trimeric antibody fragment constructs; minibodies (see, e.g., Pack et al. (1992) *Biochem* 31:1579–1584; Cumber et al. (1992) *J Immunology* 149B: 120–126); humanized antibody molecules (see, for example, Riechmann et al. (1988) *Nature* 332:323–327; Verhoeyan et al. (1988) *Science* 239:1534–1536; and U.K. Patent Publication No. GB 2,276,169, published 21 Sep. 1994); and, any functional fragments obtained from such molecules, wherein such fragments retain immunological binding properties of the parent antibody molecule.

A "recombinant" protein is a protein which retains the desired activity and which has been prepared by recombinant DNA techniques as described herein. In general, the gene of interest is cloned and then expressed in transformed organisms, as described further below. The host organism expresses the foreign gene to produce the protein under expression conditions.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

By "equivalent antigenic determinant" is meant an antigenic determinant from different sub-species or strains of HCV, such as from strains 1, 2, 3, etc. of HCV. More specifically, epitopes are known, such as 5-1-1, and such epitopes vary between the strains 1, 2, and 3. Thus, the epitope 5-1-1 from the three different strains are equivalent antigenic determinants and thus are "copies" even though their sequences are not identical. In general the amino acid sequences of equivalent antigenic determinants will have a high degree of sequence homology, e.g., amino acid sequence homology of more than 30%, preferably more than 40%, when the two sequences are aligned.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%–85%, preferably at least about 90%, and most preferably at least about 95%–98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis of similarity and identity, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence similarity and identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent similarity of a particular nucleotide sequence to a reference sequence can be determined using the homology algorithm of Smith and Waterman with a default scoring table and a gap penalty of six nucleotide positions.

Another method of establishing percent similarity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence similarity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.nih.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

"Common solid support" intends a single solid matrix to which the HCV polypeptides used in the subject immunoassays are bound covalently or by noncovalent means such as hydrophobic adsorption.

"Immunologically reactive" means that the antigen in question will react specifically with anti-HCV antibodies present in a biological sample from an HCV-infected individual.

"Immune complex" intends the combination formed when an antibody binds to an epitope on an antigen.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, strepavidin or haptens) and the like. The term "fluorescer" refers to a substance or a portion thereof which is capable of exhibiting fluorescence in the detectable range. Particular examples of labels which may be used under the invention include, but are not limited to, horse radish peroxidase (HRP), fluorescein, FITC, rhodamine, dansyl, umbelliferone, dimethyl acridinium ester (DMAE), Texas red, luminol, NADPH and α-β-galactosidase.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention is based on the discovery of novel antigen/antibody/antigen sandwich diagnostic methods for accurately detecting HCV infection. The methods can be practiced quickly and efficiently and eliminate background effects that can occur from the use of large sample volumes. The methods preferably utilize highly immunogenic HCV antigens which are present during the early stages of HCV seroconversion, thereby increasing detection accuracy and reducing the incidence of false results.

In particular, the immunoassays described herein utilize two basic HCV antigens, one present in the solid phase and one present in the solution phase. Both antigens are capable of binding HCV antibodies present in biological samples from infected individuals. One antigen used in the subject assays is an isolated antigen from a region of the HCV polyprotein. The second antigen used is a multiple epitope fusion antigen ("MEFA") comprising various HCV polypeptides, either from the same or different HCV genotypes and isolates. The MEFA includes at least one or more epitopes derived from the same region of the HCV polyprotein as the isolated HCV antigen.

In particularly preferred embodiments, one of the antigens used in the subject assays is a highly immunogenic conformational epitope derived from the NS3/4a region of the HCV polyprotein. In these embodiments, the second antigen used is a MEFA which includes one or more epitopes from the NS3/4a region (either linear or conformational), as described further below. The MEFA may therefore include multiple immunodominant epitopes derived from the NS3/4a region from one or more HCV isolates. If multiple NS3/4a epitopes are used in the multiple epitope fusion, they may be the same or different epitopes. Alternatively, the fusion antigen may include one or more epitopes derived from the NS3/4a region, as well as major linear epitopes from other HCV regions such as, without limitation, HCV core, E1, E2, P7, NS4b, NS5a and NS5b sequences.

The methods can be conveniently practiced in a single assay, using any of the several assay formats described below, such as but not limited to, assay formats which utilize a solid support to which either the isolated HCV antigen, such as the NS3/4a conformational epitope, or the MEFA, is bound. Thus, the MEFA can be provided in either the solution or the solid phase. If provided in solution, the isolated HCV antigen is present on the solid phase.

For example, in one representative method of the invention, the assay is conducted on a solid support to which has been bound one or more polypeptides including one or more conformational epitopes derived from the NS3/4a region of the HCV polyprotein. In this embodiment, the MEFA is provided in the solution phase. In an alternative embodiment, the assay is conducted on a solid support to which one or more MEFAs has been bound. In this embodiment, the polypeptide including the conformational NS3/4a epitope is provided in the solution phase. Thus, if the conformational NS3/4a epitope is present on the solid support, the MEFA is present in the solution phase, and vice versa.

In order to further an understanding of the invention, a more detailed discussion is provided below regarding the various HCV polypeptide antigens and MEFAs for use in the subject methods, as well as production of the proteins and methods of using the proteins.

HCV Antigens and MEFAs

The genomes of HCV strains contain a single open reading frame of approximately 9,000 to 12,000 nucleotides, which is transcribed into a polyprotein. As shown in FIG. 1 and Table 1, an HCV polyprotein, upon cleavage, produces at least ten distinct products, in the order of $NH_2$-Core-E1-E2-p7-NS2-NS3-NS4a-NS4b-NS5a-NS5b-COOH. The core polypeptide occurs at positions 1–191, numbered relative to HCV-1 (see, Choo et al. (1991) *Proc. Natl. Acad. Sci. USA* 88:2451–2455, for the HCV-1 genome). This polypeptide is further processed to produce an HCV polypeptide with approximately amino acids 1–173. The envelope polypeptides, E1 and E2, occur at about positions 192–383 and 384–746, respectively. The P7 domain is found at about positions 747–809. NS2 is an integral membrane protein with proteolytic activity and is found at about positions 810–1026 of the polyprotein. NS2, in combination with NS3, (found at about positions 1027–1657), cleaves the NS2–NS3 sissle bond which in turn generates the NS3 N-terminus and releases a large polyprotein that includes both serine protease and RNA helicase activities. The NS3 protease, found at about positions 1027–1207, serves to process the remaining polyprotein. The helicase activity is found at about positions 1193–1657. NS3 liberates an NS3 cofactor (NS4a, found about positions 1658–1711), two proteins (NS4b found at about positions 1712–1972, and NS5a found at about positions 1973–2420), and an RNA-dependent RNA polymerase (NS5b found at about positions 2421–3011). Completion of polyprotein maturation is initiated by autocatalytic cleavage at the NS3–NS4a junction, catalyzed by the NS3 serine protease.

TABLE 1

| Domain | Approximate Boundaries* |
|---|---|
| C (core) | 1–191 |
| E1 | 192–383 |
| E2 | 384–746 |
| P7 | 747–809 |
| NS2 | 810–1026 |
| NS3 | 1027–1657 |
| NS4a | 1658–1711 |
| NS4b | 1712–1972 |
| NS5a | 1973–2420 |
| NS5b | 2421–3011 |

*Numbered relative to HCV-1. See, Choo et al. (1991) Proc. Natl. Acad. Sci. USA 88: 2451–2455.

One component of the subject methods is an isolated antigen from any of the various regions of the HCV polyprotein as described above. Nucleic acid and amino acid sequences of a number of HCV strains and isolates, including nucleic acid and amino acid sequences of the various regions described above have been determined. For example, isolate HCV J1.1 is described in Kubo et al. (1989) *Japan. Nucl. Acids Res.* 17:10367–10372; Takeuchi et al. (1990) *Gene* 91:287–291; Takeuchi et al. (1990) *J. Gen. Virol.* 71:3027–3033; and Takeuchi et al. (1990) *Nucl. Acids Res.* 18:4626. The complete coding sequences of two independent isolates, HCV-J and BK, are described by Kato et al., (1990) *Proc. Natl. Acad. Sci. USA* 87:9524–9528 and Takamizawa et al., (1991) *J. Virol.* 65:1105–1113 respectively.

Publications that describe HCV-1 isolates include Choo et al. (1990) *Brit. Med. Bull.* 46:423–441; Choo et al. (1991) *Proc. Natl. Acad. Sci. USA* 88:2451–2455 and Han et al. (1991) *Proc. Natl. Acad. Sci. USA* 88:1711–1715. HCV isolates HC-J1 and HC-J4 are described in Okamoto et al. (1991) *Japan J. Exp. Med.* 60:167–177. HCV isolates HCT 18, HCT 23, Th, HCT 27, ECI and ECl0 are described in Weiner et al. (1991) *Virol.* 180:842–848. HCV isolates Pt-1, HCV-K1 and HCV-K2 are described in Enomoto et al. (1990) *Biochem. Biophys. Res. Commun.* 170:1021–1025. HCV isolates A, C, D & E are described in Tsukiyama-Kohara et al. (1991) *Virus Genes* 5:243–254.

Thus, for example, the isolated HCV antigen can be derived from the core region of any of these HCV isolates. This region occurs at amino acid positions 1–191 of the HCV polyprotein, numbered relative to HCV-1. Either the full-length protein, fragments thereof, such as amino acids 1–150, e.g., amino acids 1–130, 1–120, for example, amino acids 1–121, 1–122, 1–123, etc., or smaller fragments containing epitopes of the full-length protein may be used in the subject methods, such as those epitopes found between amino acids 10–53, amino acids 10–45, amino acids 67–88, amino acids 120–130, or any of the core epitopes identified in, e.g., Houghton et al., U.S. Pat. No. 5,350,671; Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; and U.S. Pat. Nos. 6,280,927 and 6,150,087, the disclosures of which are incorporated herein by reference in their entireties. Moreover, a protein resulting from a frameshift in the core region of the polyprotein, such as described in International Publication No. WO 99/63941, may be used.

Similarly, polypeptides from the HCV E1 and/or E2 regions can be used in the methods of the present invention as the isolated HCV antigen. E2 exists as multiple species (Spaete et al., *Virol.* (1992)188:819–830; Selby et al., *J. Virol.* (1996) 70:5177–5182; Grakoui et al., *J. Virol.* (1993) 67:1385–1395; Tomei et al., *J. Virol.* (1993) 67:4017–4026) and clipping and proteolysis may occur at the NB and C-termini of the E2 polypeptide. Thus, an E2 polypeptide for use herein may comprise amino acids 405–661, e.g., 400, 401, 402 . . . to 661, such as 383 or 384–661, 383 or 384–715,383 or 384–746, 383 or 384–749 or 383 or 384–809, or 383 or 384 to any C-terminus between 661–809, of an HCV polyprotein, numbered relative to the full-length HCV-1 polyprotein. Similarly, E1 polypeptides for use herein can comprise amino acids 192–326, 192–330, 192–333, 192–360, 192–363, 192–383, or 192 to any C-terminus between 326–383, of an HCV polyprotein.

Immunogenic fragments of E1 and/or E2 which comprise epitopes may be used in the subject methods. For example, fragments of E1 polypeptides can comprise from about 5 to nearly the full-length of the molecule, such as 6, 10, 25, 50, 75, 100, 125, 150, 175, 185 or more amino acids of an E1 polypeptide, or any integer between the stated numbers. Similarly, fragments of E2 polypeptides can comprise 6, 10, 25, 50, 75, 100, 150, 200, 250, 300, or 350 amino acids of an E2 polypeptide, or any integer between the stated numbers.

For example, epitopes derived from, e.g., the hypervariable region of E2, such as a region spanning amino acids 384–410 or 390–410, can be included in the fusions. A particularly effective E2 epitope to incorporate into an E2 polypeptide sequence is one which includes a consensus sequence derived from this region, such as the consensus sequence Gly-Ser-Ala-Ala-Arg-Thr-Thr-Ser-Gly-Phe-Val-Ser-Leu-Phe-Ala-Pro-Gly-Ala-Lys-Gln-Asn (SEQ ID NO:7), which represents a consensus sequence for amino acids 390–410 of the HCV type 1 genome. Additional epitopes of E1 and E2 are known and described in, e.g., Chien et al., International Publication No. WO 93/00365.

Moreover, the E1 and/or E2 polypeptides may lack all or a portion of the membrane spanning domain. With E1, generally polypeptides terminating with about amino acid position 370 and higher (based on the numbering of HCV-1 E1) will be retained by the ER and hence not secreted into growth media. With E2, polypeptides terminating with about amino acid position 731 and higher (also based on the numbering of the HCV-1 E2 sequence) will be retained by the ER and not secreted. (See, e.g., International Publication No. WO 96/04301, published Feb. 15, 1996). It should be noted that these amino acid positions are not absolute and may vary to some degree. Thus, the present invention contemplates the use of E1 and/or E2 polypeptides which retain the transmembrane binding domain, as well as polypeptides which lack all or a portion of the transmembrane binding domain, including E1 polypeptides terminating at about amino acids 369 and lower, and E2 polypeptides, terminating at about amino acid 730 and lower. Furthermore, the C-terminal truncation can extend beyond the transmembrane spanning domain towards the N-terminus. Thus, for example, E1 truncations occurring at positions lower than, e.g., 360 and E2 truncations occurring at positions lower than, e.g., 715, are also encompassed by the present invention. All that is necessary is that the truncated E1 and E2 polypeptides remain functional for their intended purpose. However, particularly preferred truncated E1 constructs are those that do not extend beyond about amino acid 300. Most preferred are those terminating at position 360. Preferred truncated E2 constructs are those with C-terminal truncations that do not extend beyond about amino acid position 715. Particularly preferred E2 truncations are those molecules truncated after any of amino acids 715–730, such as 725.

Additionally, epitopes from the NS3, NS4, NS5a, or NS5b regions can be used as the isolated HCV antigen. Particularly preferred, is the use of an epitope from the NS3/4a region. The NS3/4a region of the HCV polyprotein has been described and the amino acid sequence and overall structure of the protein are disclosed in, e.g., Yao et al., *Structure* (November 1999) 7:1353–1363; Sali et al., *Biochem.* (1998) 37:3392–3401; and Bartenschlager, R., *J. Viral Hepat.* (1999) 6:165–181. See, also, Dasmahapatra et al., U.S. Pat. No. 5,843,752, incorporated herein by reference in its entirety. The subject immunoassays can utilize at least one conformational epitope derived from the NS3/4a region that exists in the conformation as found in the naturally occurring HCV particle or its infective product, as evidenced by the preservation of protease and, optionally, helicase enzymatic activities normally displayed by the NS3/4a gene product and/or immunoreactivity of the antigen with antibodies in a biological sample from an HCV-infected subject, and a loss of the epitope's immunoreactivity upon denaturation of the antigen. For example, the conformational epitope can be disrupted by heating, changing the pH to extremely acid or basic, or by adding known organic denaturants, such as dithiothreitol (DTT) or an appropriate detergent. See, e.g., *Protein Purification Methods, a practical approach* (E. L. V. Harris and S. Angal eds., IRL Press) and the denatured product compared to the product which is not treated as above.

Protease and helicase activity may be determined using standard enzyme assays well known in the art. For example, protease activity may be determined using assays well known in the art. See, e.g., Takeshita et al., *Anal. Biochem.* (1997) 247:242–246; Kakiuchi et al., *J. Biochem.* (1997) 122:749–755; Sali et al., *Biochemistry* (1998) 37:3392–3401; Cho et al., *J. Virol. Meth.* (1998) 72:109–115; Cerretani et al., *Anal. Biochem.* (1999) 266:192–197; Zhang et al., *Anal. Biochem.* (1999) 270:268–275; Kakiuchi et al., *J. Virol. Meth.* (1999) 80:77–84; Fowler et al., *J. Biomol. Screen.* (2000) 5:153–158; and Kim et al., *Anal. Biochem.* (2000) 284:42–48. A particularly convenient assay for testing protease activity is set forth in the examples below.

Similarly, helicase activity assays are well known in the art and helicase activity of an NS3/4a epitope may be determined using, for example, an ELISA assay, as described in, e.g., Hsu et al., *Biochem. Biophys. Res. Commun.* (1998) 253:594–599; a scintillation proximity assay system, as described in Kyono et al., *Anal. Biochem.* (1998) 257:120–126; high throughput screening assays as described in, e.g., Hicham et al., *Antiviral Res.* (2000) 46:181–193 and Kwong et al., *Methods Mol. Med.* (2000) 24:97–116; as well as by other assay methods known in the art. See, e.g., Khu et al., *J. Virol.* (2001) 75:205–214; Utama et al., *Virology* (2000) 273:316–324; Paolini et al., *J. Gen. Virol.* (2000) 81:1335–1345; Preugschat et al., *Biochemistry* (2000) 39:5174–5183; Preugschat et al., *Methods Mol. Med.* (1998) 19:353–364; and Hesson et al., *Biochemistry* (2000) 39:2619–2625.

If a conformational NS3/4a epitope is used, the length of the antigen is sufficient to maintain an immunoreactive conformational epitope. Often, the polypeptide containing the antigen used will be almost full-length, however, the polypeptide may also be truncated to, for example, increase solubility or to improve secretion. Generally, the conformational epitope found in NS3/4a is expressed as a recombinant polypeptide in a cell and this polypeptide provides the epitope in a desired form, as described in detail below.

A representative amino acid sequence for an NS3/4a polypeptide is shown in FIGS. 3A through 3D (SEQ ID NOS:1 and 2). The amino acid sequence shown at positions 2–686 of FIGS. 3A through 3D corresponds to amino acid positions 1027–1711 of HCV-1. An initiator codon (ATG) coding for Met, is shown as position 1. Additionally, the Thr normally occurring at position 1428 of HCV-1 (amino acid position 403 of FIG. 3) is mutated to Pro, and the Ser normally occurring at position 1429 of HCV-1 (amino acid position 404 of FIG. 3) is mutated to Ile. However, either the native sequence, with or without an N-terminal Met, the depicted analog, with or without the N-terminal Met, or other analogs and fragments can be used in the subject assays, so long as the epitope is produced using a method that retains or reinstates its native conformation such that protease activity, and optionally, helicase activity is retained. Dasmahapatra et al., U.S. Pat. No. 5,843,752 and Zhang et al., U.S. Pat. No. 5,990,276, both describe analogs of NS3/4a.

The NS3 protease of NS3/4a is found at about positions 1027–1207, numbered relative to HCV-1, positions 2–182 of FIG. 3. The structure of the NS3 protease and active site are known. See, e.g., De Francesco et al., *Antivir. Ther.* (1998) 3:99–109; Koch et al., *Biochemistry* (2001) 40:631–640. Changes to the native sequence that will normally be tolerated will be those outside of the active site of the molecule. Particularly, it is desirable to maintain amino acids 1- or 2–155 of FIG. 3, with little or only conservative substitutions. Amino acids occurring beyond position 155 will tolerate greater changes. Additionally, if fragments of the NS3/4a sequence are used, these fragments will generally include at least amino acids 1- or 2–155, preferably amino acids 1- or 2–175, and most preferably amino acids 1- or 2–182, with or without the N-terminal Met. The helicase domain is found at about positions 1193–1657 of HCV-1 (positions 207–632 of FIG. 3). Thus, if helicase activity is desired, this portion of the molecule will be maintained with little or only conservative changes. One of skill in the art can readily determine other regions that will tolerate change based on the known structure of NS3/4a.

A number of antigens including epitopes derived from NS3/4a are known, including, but not limited to antigens derived from the c33c, c200, c100 and 5-1-1 regions, as well as fusion proteins comprising an NS3 epitope, such as c25.

For a description of these and various other HCV epitopes from other HCV regions, see, e.g., Houghton et al, U.S. Pat. No. 5,350,671; Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; and U.S. Pat. Nos. 6,280,927 and 6,150,087, incorporated herein by reference in their entireties.

The immunoassays described herein also utilize multiple epitope fusion antigens (termed "MEFAs"), as described in International Publication Nos. WO 01/96875, WO 01/09609, WO 97/44469 and U.S. Pat. Nos. 6,514,731 and 6,428,792, incorporated herein by reference in their entireties. The MEFAs for use in the subject assays include multiple epitopes derived from any of the various viral regions shown in FIG. 1 and Table 1, and as described above.

The multiple HCV antigens are part of a single, continuous chain of amino acids, which chain does not occur in nature. Thus, the linear order of the epitopes is different than their linear order in the genome in which they occur. The linear order of the sequences of the MEFAs for use herein is preferably arranged for optimum antigenicity. Preferably, the epitopes are from more than one HCV strain, thus providing the added ability to detect multiple strains of HCV in a single assay. Thus, the MEFAs for use herein may comprise various immunogenic regions derived from the polyprotein described above.

As explained above, in a particularly preferred embodiment, an NS3/4a epitope is used as the isolated HCV antigen. In this embodiment, the MEFA includes at least one or more epitopes derived from the NS3/4a region (either linear or conformational). The MEFA may therefore include multiple immunodominant epitopes derived from the NS3/4a region from one or more HCV isolates. If multiple NS3/4a epitopes are used in the multiple epitope fusion, they may be the same or different epitopes. Alternatively, the fusion antigen may include one or more epitopes derived from the NS3/4a region, as well as major linear epitopes from other HCV regions such as, without limitation, HCV core, E1, E2, P7, NS4b, NS5a and NS5b sequences.

Polypeptides comprising epitopes derived from the NS3/4a region include, without limitation, polypeptides comprising all or a portion of the NS3, NS4a and NS3/4a regions. A number of epitopes from these regions are known, including, but not limited to antigens derived from the c33c, c200 and c100 regions, as well as fusion proteins comprising an NS3 epitope, such as c25. These and other NS3 epitopes are useful in the present assays and are known in the art and described in, e.g., Houghton et al, U.S. Pat. No. 5,350,671; Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; and U.S. Pat. Nos. 6,346,375 and 6,150,087, the disclosures of which are incorporated herein by reference in their entireties.

Moreover, the antigenic determinant known as 5-1-1 is partially within the NS4a region (see, FIG. 1) and is particularly useful in the MEFAs for use in the subject assays. This antigenic determinant appears in three different forms on three different viral strains of HCV. Accordingly, in a preferred embodiment of the invention all three forms of 5-1-1 appear on the multiple epitope fusion antigen used in the subject immunoassays.

Additional HCV epitopes for use in the MEFAs include any of the various epitopes described above, such as epitopes derived from the hypervariable region of E2, such as a region spanning amino acids 384–410 or 390–410, or the consensus sequence from this region as described above (Gly-Ser-Ala-Ala-Arg-Thr-Thr-Ser-Gly-Phe-Val-Ser-Leu-Phe-Ala-Pro-Gly-Ala-Lys-Gln-Asn) (SEQ ID NO: 7), which represents a consensus sequence for amino acids 390–410 of the HCV type 1 genome. A representative E2 epitope present in a MEFA of the invention can comprise a hybrid epitope spanning amino acids 390–444. Such a hybrid E2 epitope can include a consensus sequence representing amino acids 390–410 fused to the native amino acid sequence for amino acids 411–444 of HCV E2.

As explained above, the antigens may be derived from various HCV strains. Multiple viral strains of HCV are known, and epitopes derived from any of these strains can be used in a fusion protein. It is well known that any given species of organism varies from one individual organism to another and further that a given organism such as a virus can have a number of different strains. For example, as explained above, HCV includes at least 6 genotypes. Each of these genotypes includes equivalent antigenic determinants. More specifically, each strain includes a number of antigenic determinants that are present on all strains of the virus but are slightly different from one viral strain to another. Similarly, equivalent antigenic determinants from the core region of different HCV strains may also be present. In general, equivalent antigenic determinants have a high degree of homology in terms of amino acid sequence which degree of homology is generally 30% or more, preferably 40% or more, when aligned. The multiple copy epitope of the present invention can also include multiple copies which are exact copies of the same epitope.

Representative MEFAs for use with the present assays are shown in FIGS. 5, 7 and 9A–9C, and are described in International publication nos. WO 01/96875, WO 01/09609, WO 97/44469 and U.S. Pat. Nos. 6,514,731 and 6,428,792, incorporated herein by reference in their entireties. Representative MEFAs for use herein include those termed MEFA 3, MEFA 5, MEFA 6, MEFA 7.1, MEFA 12, MEFA 13 and MEFA 13.1. It is to be understood that these MEFAs are merely representative and other epitopes derived from the HCV genome will also find use with the present assays and may be incorporated into these or other MEFAs.

Figure 5:
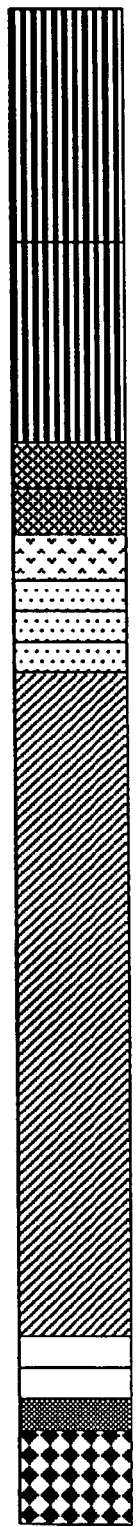
FIG. 5 is a diagrammatic representation of MEFA 12.

The DNA sequence and corresponding amino acid sequence of MEFA 12 is shown in FIGS. 6A through 6F (SEQ ID NOS:3 and 4). The general structural formula for MEFA 12 is shown in FIG. 5 and is as follows: hSOD-E1 (type 1)-E2 HVR consensus(type 1a)-E2 HVR consensus (types 1 and 2)-c33c short(type 1)-5-1-1(type 1)-5-1-1(type 3)-5-1-1(type 2)-c100(type 1)-NS5(type 1)-NS5(type 1)-core(types 1+2)-core(types 1+2). This multiple copy epitope includes the following amino acid sequence, numbered relative to HCV-1 (the numbering of the amino acids set forth below follows the numbering designation provided in Choo, et al. (1991) *Proc. Natl. Acad. Sci. USA* 88:2451–2455, in which amino acid #1 is the first methionine encoded by the coding sequence of the core region): amino acids 1–69 of superoxide dismutase (truncated SOD, used to enhance recombinant expression of the protein); amino acids 303 to 320 of the polyprotein from the E1 region; amino acids 390 to 410 of the polyprotein, representing a consensus sequence for the hypervariable region of HCV-1a E2; amino acids 384 to 414 of the polyprotein from region E2, representing a consensus sequence for the E2 hypervariable regions of HCV-1 and HCV-2; amino acids 1211–1457 of the HCV-1 polyprotein which define the helicase; three copies of an epitope from 5-1-1, amino acids 1689–1735, one from HCV-1, one from HCV-3 and one from HCV-2, which copies are equivalent antigenic determinants from the three different viral strains of HCV; HCV polypeptide c100 of HCV-1, amino acids 1901–1936 of the polyprotein; two exact copies of an epitope from the NS5 region of HCV-1, each with amino acids 2278 to 2313 of the HCV polyprotein; and two copies of three epitopes from the core region, two from HCV-1 and one from HCV-2, which copies are equivalent antigenic determinants represented by amino acids 9 to 53 and 64–88 of HCV-1 and 67–84 of HCV-2.

Table 2 shows the amino acid positions of the various epitopes in MEFA 12 with reference to FIGS. 6A through 6F herein (SEQ ID NOS:3 and 4). The numbering in the tables is relative to HCV-1. See, Choo et al. (1991) Proc. Natl. Acad. Sci. USA 88:2451–2455. MEFAs 13 and 13.1 also share the general formula specified above for MEFA 12, with modifications as indicated in Tables 3 and 4, respectively.

TABLE 2

MEFA 12

| mefa aa# | 5' end site | epitope | hcv aa# | strain |
|---|---|---|---|---|
| 1–69 | Nco1 | truncated hSOD | | |
| 72–89 | MluI | E1 | 303–320 | 1 |
| 92–112 | Hind111 | E2 HVR1a consensus | 390–410 | 1 |
| 113–143 | | E2 HVR1+2 consensus | 384–414 | 1, 2 |
| 146–392 | SpeI | C33C short | 1211–1457 | 1 |
| 395–441 | SphI | 5-1-1 | 1689–1735 | 1 |
| 444–490 | NruI | 5-1-1 | 1689–1735 | 3 |
| 493–539 | ClaI | 5-1-1 | 1689–1735 | 2 |
| 542–577 | AvaI | C100 | 1901–1936 | 1 |
| 580–615 | XbaI | NS5 | 2278–2313 | 1 |
| 618–653 | BglII | NS5 | 2278–2313 | 1 |
| 654–741 | NcoI | core epitopes | 9–53, R47L 64–88 67–84 | 1 1 2 |
| 742–829 | BalI | core epitopes | 9–53, R47L 64–88 67–84 | 1 1 2 |

TABLE 3

MEFA 13

| mefa aa# | 5' end site | epitope | hcv aa# | strain |
|---|---|---|---|---|
| 1–156 | Nco1 | mutated hSOD (aa 70–72, ALA) | | |
| 161–178 | MluI | E1 | 303–320 | 1 |
| 181–201 | Hind111 | E2 HVR1a consensus | 390–410 | 1 |
| 202–232 | | E2 HVR1+2 consensus | 384–414 | 1, 2 |
| 235–451 | | C33C short | 1211–1457 | 1 |
| 454–500 | HindIII | 5-1-1 PImut* | 1689–1735 | 1 |
| 503–549 | NruI | 5-1-1 PImut* | 1689–1735 | 3 |
| 552–598 | ClaI | 5-1-1 PImut* | 1689–1735 | 2 |
| 601–636 | AvaI | C100 | 1901–1936 | 1 |
| 639–674 | XbaI | NS5 | 2278–2313 | 1 |
| 677–712 | BglII | NS5 | 2278–2313 | 1 |
| 713–800 | | core epitopes | 9–53, R47L 64–88 67–84 | 1 1 2 |
| 801–888 | | core epitopes | 9–53, R47L 64–88 67–84 | 1 1 2 |

*The 5-1-1 epitopes are modified by eliminating possible cleavage sites (CS or CA) targeted by the NS3/4a recombinant protein. Instead of CS or CA, the sequence has been changed to PI.

TABLE 4

MEFA 13.1

| mefa aa# | 5' end site | epitope | hcv aa# | strain |
|---|---|---|---|---|
| 1–86 | NcoI | mutated hSOD (aa 70–72, ALA) | | |
| 89–106 | MluI | E1 | 303–320 | 1 |
| 109–129 | HindIII | E2 HVR1a consensus | 390–410 | 1 |
| 130–160 | | E2 HVR1+2 consensus | 384–414 | 1, 2 |
| 163–379 | | C33C short | 1211–1457 | 1 |
| 382–428 | HindIII | 5-1-1 PImut* | 1689–1735 | 1 |
| 431–477 | NruI | 5-1-1 PImut* | 1689–1735 | 3 |
| 480–526 | ClaI | 5-1-1 PImut* | 1689–1735 | 2 |
| 529–564 | AvaI | C100 | 1901–1936 | 1 |
| 567–602 | XbaI | NS5 | 2278–2313 | 1 |
| 605–640 | BglII | NS5 | 2278–2313 | 1 |
| 641–728 | | core epitopes | 9–53, R47L 64–88 67–84 | 1 1 2 |
| 729–816 | | core epitopes | 9–53, R47L 64–88 67–84 | 1 1 2 |

*The 5-1-1 epitopes are modified by eliminating possible cleavage sites (CS or CA) targeted by the NS3/4a recombinant protein. Instead of CS or CA, the sequence has been changed to PI.

Figure 7:
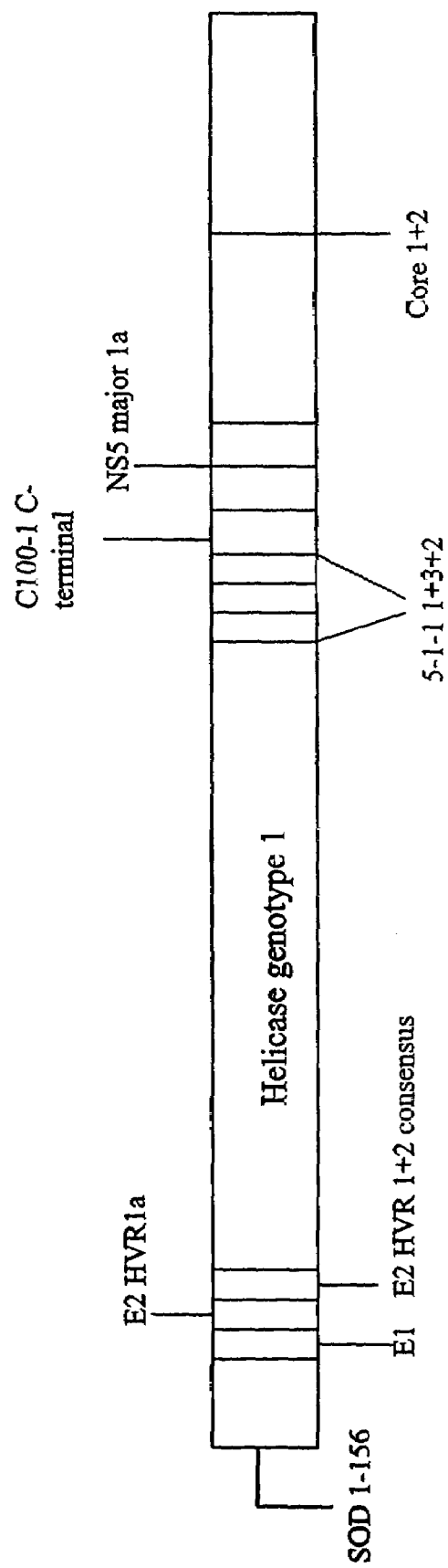
FIG. 7 is a diagrammatic representation of MEFA 7.1.

The DNA sequence and corresponding amino acid sequence of another representative multiple epitope fusion antigen, MEFA 7.1, is shown in FIGS. 8A through 8F (SEQ ID NOS:5 and 6). The general structural formula for MEFA 7.1 is shown in FIG. 7 and is as follows: hSOD-E1(type 1)-E2 HVR consensus(type 1a)-E2 HVR consensus(types 1 and 2)-helicase(type 1)-5-1-1(type 1)-5-1-1(type 3)-5-1-1 (type 2)-c100(type 1)-NS5(type 1)-NS5(type 1)-core(types 1+2)-core(types 1+2). This multiple copy epitope includes the following amino acid sequence, numbered relative to HCV-1 (the numbering of the amino acids set forth below follows the numbering designation provided in Choo, et al. (1991) *Proc. Natl. Acad. Sci. USA* 88:2451–2455, in which amino acid #1 is the first methionine encoded by the coding sequence of the core region): amino acids 1–156 of superoxide dismutase (SOD, used to enhance recombinant expression of the protein); amino acids 303 to 320 of the polyprotein from the E1 region; amino acids 390 to 410 of the polyprotein, representing a consensus sequence for the hypervariable region of HCV-1a E2; amino acids 384 to 414 of the polyprotein from region E2, representing a consensus sequence for the E2 hypervariable regions of HCV-1 and HCV-2; amino acids 1193–1658 of the HCV-1 polyprotein which define the helicase; three copies of an epitope from 5-1-1, amino acids 1689–1735, one from HCV-1, one from HCV-3 and one from HCV-2, which copies are equivalent antigenic determinants from the three different viral strains of HCV; HCV polypeptide C 100 of HCV-1, amino acids 1901–1936 of the polyprotein; two exact copies of an epitope from the NS5 region of HCV-1, each with amino acids 2278 to 2313 of the HCV polyprotein; and two copies of an epitope from the core region, one from HCV-1 and one from HCV-2, which copies are equivalent antigenic determinants represented by amino acids 9 to 32, 39–42 and 64–88 of HCV-1 and 67–84 of HCV-2.

Table 5 shows the amino acid positions of the various epitopes with reference to FIGS. 8A through 8F herein (SEQ ID NOS:5 and 6).

TABLE 5

MEFA 7.1

| mefa aa# | 5' end site | epitope | hcv aa# | strain |
|---|---|---|---|---|
| 1–156 | Nco1 | hSOD | | |
| 159–176 | EcoR1 | E1 | 303–320 | 1 |
| 179–199 | Hind111 | E2 HVR1a consensus | 390–410 | 1 |
| 200–230 | | E2 HVR1+2 consensus | 384–414 | 1 + 2 |
| 231–696 | Sal1 | Helicase | 1193–1658 | 1 |
| 699–745 | Sph1 | 5-1-1 | 1689–1735 | 1 |
| 748–794 | Nru1 | 5-1-1 | 1689–1735 | 3 |
| 797–843 | Cla1 | 5-1-1 | 1689–1735 | 2 |
| 846–881 | Ava1 | C100 | 1901–1936 | 1 |
| 884–919 | Xba1 | NS5 | 2278–2313 | 1 |
| 922–957 | Bgl11 | NS5 | 2278–2313 | 1 |
| 958–1028 | Nco1 | core epitopes | 9–32, 39–42 64–88 67–84 | 1 1 2 |
| 1029–1099 | Bal1 | core epitopes | 9–32, 39–42, 64–88 67–84 | 1 1 2 |

In one assay format, the sample is combined with the solid support, as described further below. The solid support includes either the isolated HCV antigen, such as one or more NS3/4a conformational epitopes, or a MEFA as described above, the MEFA including one or more epitopes derived from the same region of the polyprotein as the HCV antigen, such as from the NS3/4a region. As explained above, a number of antigens including such epitopes are known, including, but not limited to antigens derived from the c33c and c100 regions, as well as fusion proteins comprising an NS3 epitope, such as c25, and the antigenic determinant known as 5-1-1 which is partially within the NS4a region (see, FIG. 1). These and other NS3/4a epitopes are useful in the present assays and are known in the art and described in, e.g., Houghton et al, U.S. Pat. No. 5,350,671; Chien et al., *Proc. Natl. Acad. Sci. USA* (1992) 89:10011–10015; Chien et al., *J. Gastroent. Hepatol.* (1993) 8:S33–39; Chien et al., International Publication No. WO 93/00365; Chien, D. Y., International Publication No. WO 94/01778; and U.S. Pat. Nos. 6,346,375 and 6,150,087, the disclosures of which are incorporated herein by reference in their entireties.

If the sample is infected with HCV, HCV antibodies to an epitope present on the solid support, will bind to the solid support components. A detectably labeled antigen that also reacts with the captured HCV antibody from the biological sample, is also added in the solution phase. For example, if the antigen bound to the solid support is an NS3/4a conformational epitope, the detectably labeled antigen used in the solution phase is a MEFA that includes an NS3/4a epitope. If the antigen bound to the solid support is a MEFA that includes an NS3/4a epitope, the detectably labeled antigen used in the solution phase includes a conformational NS3/4a epitope.

Figure 2:
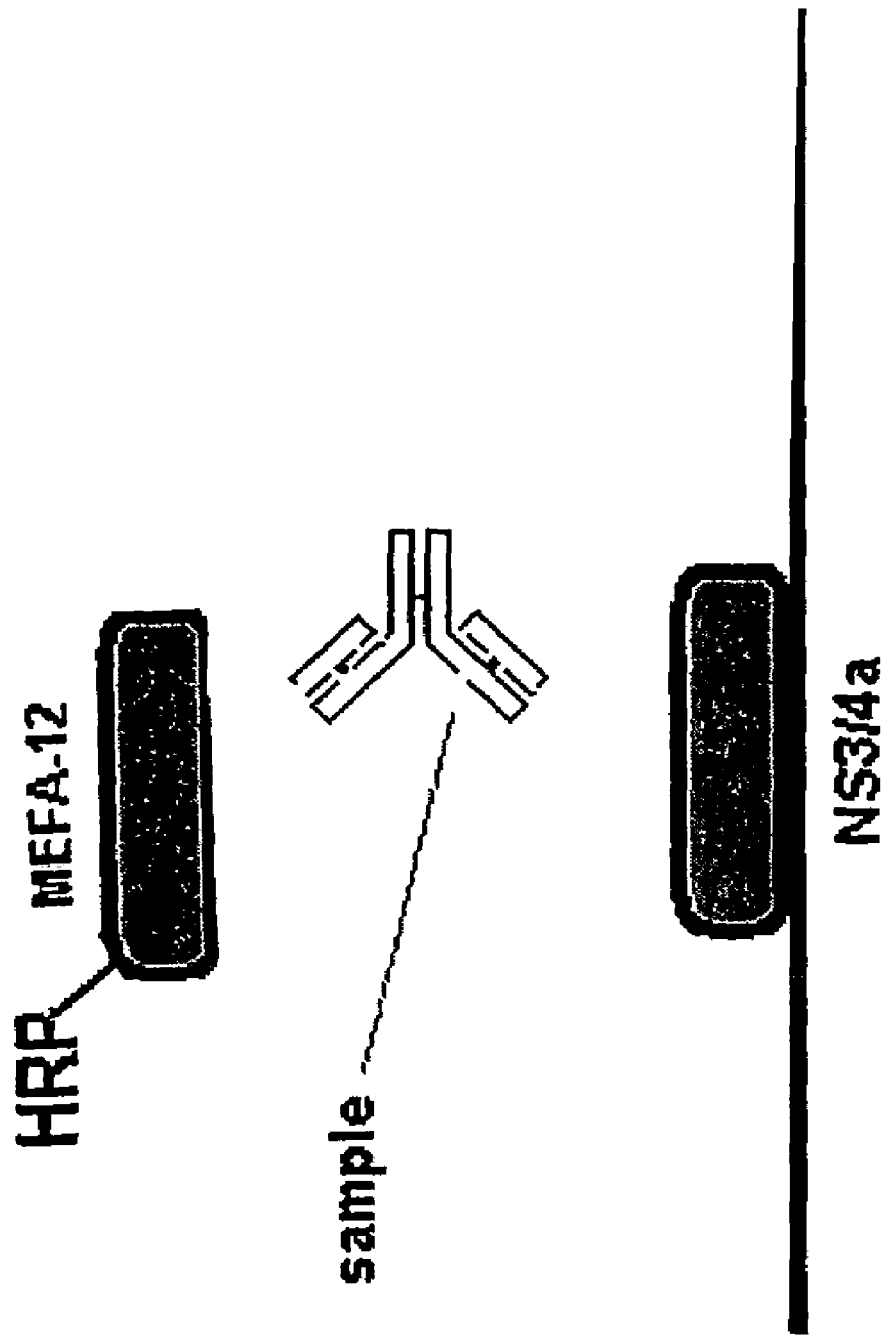
FIG. 2 is a schematic drawing of a representative antigen/antibody/antigen sandwich assay under the invention, using MEFA 12.

A representative assay under the invention is depicted in FIG. 2. As shown in the figure, the solid support includes a conformational NS3/4a epitope. The biological sample is added to the solid support. HCV antibodies directed against the NS3/4a epitope present in the sample, will bind the NS3/4a epitope on the solid support. Horse radish peroxidase (HRP)-labeled MEFA 12, including an epitope to which sample antibodies bind, is then added. MEFA 12 binds the antibody that is also bound by the NS3/4a conformational epitope. Unbound components are washed away and detection of the label indicates the presence of HCV infection.

The above-described antigen/antibody/antigen sandwich assays are particularly advantageous as the use of two antigens which bind sample antibody allows for the use of larger volumes of sample. Additionally, the assay can be completed quickly.

Production of Antigens for Use in the HCV Immunoassays

As explained above, the molecules of the present invention are generally produced recombinantly. Thus, polynucleotides encoding HCV antigens for use with the present invention can be made using standard techniques of molecular biology. For example, polynucleotide sequences coding for the above-described molecules can be obtained using recombinant methods, such as by screening cDNA and genomic libraries from cells expressing the gene, or by deriving the gene from a vector known to include the same. Furthermore, the desired gene can be isolated directly from viral nucleic acid molecules, using techniques described in the art, such as in Houghton et al., U.S. Pat. No. 5,350,671. The gene of interest can also be produced synthetically, rather than cloned. The molecules can be designed with appropriate codons for the particular sequence. The complete sequence is then assembled from overlapping oligonucleotides prepared by standard methods and assembled into a complete coding sequence. See, e.g., Edge (1981) *Nature* 292:756; Nambair et al. (1984) *Science* 223:1299; and Jay et al. (1984) *J. Biol. Chem.* 259:6311.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PVR. See, e.g., Jayaraman et al. (1991) *Proc. Natl. Acad. Sci. USA* 88:4084–4088. Additionally, oligonucleotide directed synthesis (Jones et al. (1986) *Nature* 54:75–82), oligonucleotide directed mutagenesis of pre-existing nucleotide regions (Riechmann et al. (1988) *Nature* 332:323–327 and Verhoeyen et al. (1988) *Science* 239:1534–1536), and enzymatic filling-in of gapped oligonucleotides using $T_4$ DNA polymerase (Queen et al. (1989) *Proc. Natl. Acad. Sci. USA* 86:10029–10033) can be used under the invention to provide molecules having altered or enhanced antigen-binding capabilities, and/or reduced immunogenicity.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

As explained above, it may also be desirable to produce mutants or analogs of the antigen of interest. This is particularly true with NS3/4a. Methods for doing so are described in, e.g., Dasmahapatra et al., U.S. Pat. No. 5,843,752 and Zhang et al., U.S. Pat. No. 5,990,276. Mutants or analogs of this and other HCV proteins for use in the subject assays may be prepared by the deletion of a portion of the sequence encoding the polypeptide of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci USA* 79:6409.

The molecules can be expressed in a wide variety of systems, including insect, mammalian, bacterial, viral and yeast expression systems, all well known in the art.

For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and Streptococcus spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

The recombinant production of various HCV antigens has been described. See, e.g., Houghton et al., U.S. Pat. No. 5,350,671; Chien et al., *J. Gastroent. Hepatol.* (1993) 8:S33–39; Chien et al., International Publication No. WO 93/00365; Chien, D. Y., International Publication No. WO 94/01778.

Immunodiagnostic Assays

Once produced, the above HCV antigens are placed on an appropriate solid support for use in the subject immunoassays. A solid support, for the purposes of this invention, can be any material that is an insoluble matrix and can have a rigid or semi-rigid surface. Exemplary solid supports include, but are not limited to, substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. Particular supports include plates, pellets, disks, capillaries, hollow fibers, needles, pins, solid fibers, cellulose beads, pore-glass beads, silica gels, polystyrene beads optionally cross-linked with divinylbenzene, grafted co-poly beads, polyacrylamide beads, latex beads, dimethylacrylamide beads optionally crosslinked with N-N'-bis-acryloylethylenediamine, and glass particles coated with a hydrophobic polymer.

If desired, the molecules to be added to the solid support can readily be functionalized to create styrene or acrylate moieties, thus enabling the incorporation of the molecules into polystyrene, polyacrylate or other polymers such as polyimide, polyacrylamide, polyethylene, polyvinyl, polydiacetylene, polyphenylene-vinylene, polypeptide, polysaccharide, polysulfone, polypyrrole, polyimidazole, polythiophene, polyether, epoxies, silica glass, silica gel, siloxane, polyphosphate, hydrogel, agarose, cellulose, and the like.

In one context, a solid support is first reacted with either the isolated HCV antigen or the MEFA (called "the solid-phase component" herein), under suitable binding conditions such that the molecules are sufficiently immobilized to the support. Sometimes, immobilization to the support can be enhanced by first coupling the antigen to a protein with better solid phase-binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other reagents that can be used to bind molecules to the support include polysaccharides, polylactic acids, polyglycolic acids, polymeric amino acids, amino acid copolymers, and the like. Such molecules and methods of coupling these molecules to antigens, are well known to those of ordinary skill in the art. See, e.g., Brinkley, M. A. (1992) *Bioconjugate Chem.* 3:2–13; Hashida et al. (1984) *J. Appl. Biochem.* 6:56–63; and Anjaneyulu and Staros (1987) *International J. of Peptide and Protein Res.* 30:117–124.

After reacting the solid support with the solid-phase components, any nonimmobilized solid-phase components are removed from the support by washing, and the support-bound components are then contacted with a biological sample suspected of containing HCV antibodies (called "ligand molecules" herein) under suitable binding conditions. After washing to remove any nonbound ligand molecules, a second HCV antigen (either an isolated HCV antigen or the MEFA, depending on which antigen is bound to the solid support), is added under suitable binding conditions. This second antigen is termed the "solution-phase component" herein. The added antigen includes a detectable label, as described above, and binds ligand molecules that have reacted with the support-bound antigen. Thus, the ligand molecules bind both the solid-phase component, as well as the solution-phase component. Unbound ligand molecules and solution-phase components are removed by washing. The presence of a label therefore indicates the presence of HCV antibodies in the biological sample.

More particularly, an ELISA method can be used, wherein the wells of a microtiter plate are coated with the solid-phase components. A biological sample containing or suspected of containing ligand molecules is then added to the coated wells. After a period of incubation sufficient to allow ligand-molecule binding to the immobilized solid-phase component, the plate(s) can be washed to remove unbound moieties and a detectably labeled solution-phase component is added. These molecules are allowed to react with any captured sample antibody, the plate washed and the presence of the label detected using methods well known in the art.

The above-described assay reagents, including the immunoassay solid support with bound antigens, as well as antigens to be reacted with the captured sample, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Production of an NS3/4a Conformational Epitope with Thr to Pro and Ser to Ile Substitutions A conformational epitope of NS3/4a was obtained as follows. This epitope has the sequence specified in FIGS. 3A through 3D (SEQ ID NOS:1 and 2) and differs from the native sequence at positions 403 (amino acid 1428 of the HCV-1 full-length sequence) and 404 (amino acid 1429 of the HCV-1 full-length sequence). Specifically, the Thr normally occurring at position 1428 of the native sequence has been mutated to Pro and Ser which occurs at position 1429 of the native sequence has been mutated to Ile.

In particular, the yeast expression vector used was pBS24.1. This yeast expression vector contains 2µ sequences and inverted repeats (IR) for autonomous replication in yeast, the α-factor terminator to ensure transcription termination, and the yeast leu2-d and URA3 for selection. The ColE1 origin of replication and the β-lactamase gene are also present for propagation and selection in *E. coli* (Pichuantes et al. (1996) "Expression of Heterologous Gene Products in Yeast." In: *Protein Engineering: A Guide to Design and Production*, Chapter 5. J. L. Cleland and C. Craik, eds., Wiley-Liss, Inc., New York, N.Y. pp. 129–161.

Plasmid pd.hcv1a.ns3ns4aPI, which encoded a representative NS3/4a epitope used in the subject immunoassays, was produced as follows. A two step procedure was used. First, the following DNA pieces were ligated together: (a) synthetic oligonucleotides which would provide a 5' HindIII cloning site, followed by the sequence ACAAAACAAA (SEQ ID NO: 8), the initiator ATG, and codons for HCV1a, beginning with amino acid 1027 and continuing to a BglI site at amino acid 1046; (b) a 683 bp BglI-ClaI restriction fragment (encoding amino acids 1046–1274) from pAcHLTns3ns4aPI; and (c) a pSP72 vector (Promega, Madison, Wis., GenBank/EMBL Accession Number X65332) which had been digested with HindIII and ClaI, dephosphorylated, and gel-purified. Plasmid pAcHLTns3ns4aPI was derived from pAcHLT, a baculovirus expression vector commercially available from BD Pharmingen (San Diego, Calif.). In particular, a pAcHLT EcoRI-PstI vector was prepared, as well as the following fragments: EcoRI-AlwnI, 935 bp, corresponding to amino acids 1027–1336 of the HCV-1 genome; AlwnI-SacII, 247 bp, corresponding to amino acids 1336–1419 of the HCV-1 genome; HinfI-BglI, 175 bp, corresponding to amino acids 1449–1509 of the HCV-1 genome; BglI-PstI, 619 bp, corresponding to amino acids 1510–1711 of the HCV-1 genome, plus the transcription termination codon. A SacII-HinfI synthetically generated fragment of 91 bp, corresponding to amino acids 1420–1448 of the HCV-1 genome and containing the PI mutations (Thr-1428 mutated to Pro, Ser-1429 mutated to Ile), was ligated with the 175 bp HinfI-BglI fragment and the 619 bp BglI-PstI fragment described above and subcloned into a pGEM-5Zf(+) vector digested with SacII and PstI. pGEM-5Zf(+) is a commercially available E. coli vector (Promega, Madison, Wis., GenBank/EMBL Accession Number X65308). After transformation of competent HB101 cells, miniscreen analysis of individual clones and sequence verification, an 885 bp SacII-PstI fragment from pGEM5.PI clone2 was gel-purified. This fragment was ligated with the EcoRI-AlwnI 935 bp fragment, the AlwnI-SacII 247 bp fragment and the pAcHLT EcoRI-PstI vector, described above. The resultant construct was named pAcHLTns3ns4aPI.

The ligation mixture above was transformed into HB101-competent cells and plated on Luria agar plates containing 100 µg/ml ampicillin. Miniprep analyses of individual clones led to the identification of putative positives, two of which were amplified. The plasmid DNA for pSP72 1aHC, clones #1 and #2 were prepared with a Qiagen Maxiprep kit and were sequenced.

Figure 4:
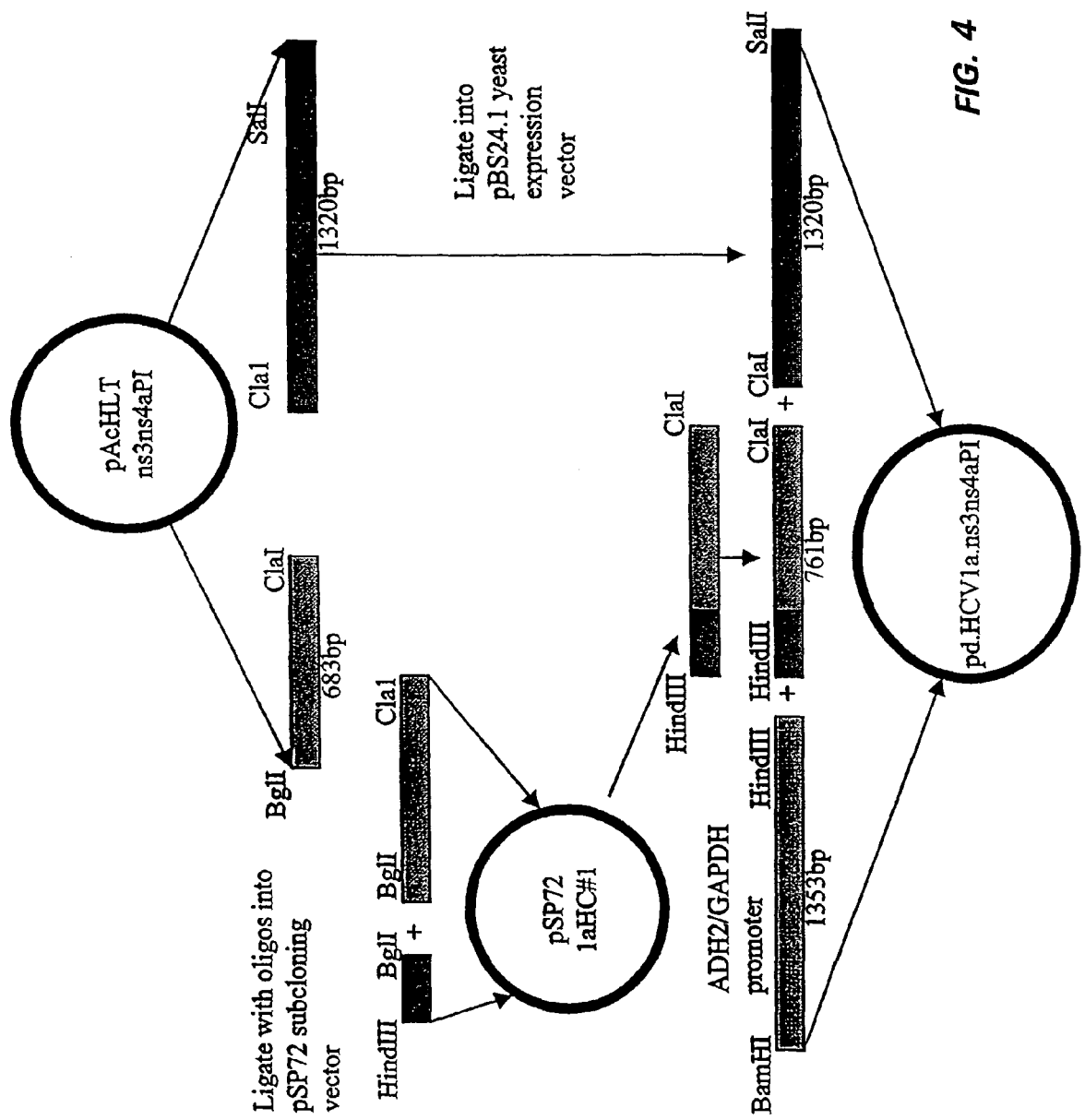
FIG. 4 is a diagram of the construction of pd.HCV1a.ns3ns4aPI.

Next, the following fragments were ligated together: (a) a 761 bp HindIII-ClaI fragment from pSP721aHC #1 (pSP72.1aHC was generated by ligating together the following: pSP72 which had been digested with HindIII and ClaI, synthetic oligonucleotides which would provide a 5' HindIII cloning site, followed by the sequence ACAAAA-CAAA (SEQ ID NO: 8), the initiation codon ATG, and codons for HCV1a, beginning with amino acid 1027 and continuing to a BglII site at amino acid 1046, and a 683 bp BglII-ClaI restriction fragment (encoding amino acids 1046–1274) from pAcHLTns3ns4aPI); (b) a 1353 bp BamHI-HindIII fragment for the yeast hybrid promoter ADH2/GAPDH; (c) a 1320 bp ClaI-SalI fragment (encoding HCV1a amino acids 1046–1711 with Thr 1428 mutated to Pro and Ser 1429 mutated to Ile) from pAcHLTns3ns4aPI; and (d) the pBS24.1 yeast expression vector which had been digested with BamHI and SalI, dephosphorylated and gel-purified. The ligation mixture was transformed into competent HB101 and plated on Luria agar plates containing 100 µg/ml ampicillin. Miniprep analyses of individual colonies led to the identification of clones with the expected 3446 bp BamHI-SalI insert which was comprised of the ADH2/GAPDH promoter, the initiator codon ATG and HCV1a NS3/4a from amino acids 1027–1711 (shown as amino acids 1–686 of FIGS. 3A–3D), with Thr 1428 (amino acid position 403 of FIGS. 3A–3D) mutated to Pro and Ser 1429 (amino acid position 404 of FIGS. 3A–3D) mutated to Ile. The construct was named pd.HCV1a.ns3ns4aPI (see, FIG. 4).

S. cerevisiae strain AD3 was transformed with pd.HCV1a.ns3ns4aPI and single transformants were checked for expression after depletion of glucose in the medium. The recombinant protein was expressed at high levels in yeast, as detected by Coomassie blue staining and confirmed by immunoblot analysis using a polyclonal antibody to the helicase domain of NS3.

EXAMPLE 2

Purification of NS3/4a Conformational Epitope

The NS3/4a conformational epitope was purified as follows. S. cerevisiae cells from above, expressing the NS3/4a epitope were harvested as described above. The cells were suspended in lysis buffer (50 mM Tris pH 8.0, 150 mM NaCl, 1 mM EDTA, 1 mM PMSF, 0.1 µM pepstatin, 1 µM leupeptin) and lysed in a Dyno-Mill (Wab Willy A. Bachofon, Basel, Switzerland) or equivalent apparatus using glass beads, at a ratio of 1:1:1 cells:buffer:0.5 mm glass beads. The lysate was centrifuged at 30100×g for 30 min at 4° C. and the pellet containing the insoluble protein fraction was added to wash buffer (6 ml/g start cell pellet weight) and rocked at room temperature for 15 min. The wash buffer consisted of 50 mM NaPO$_4$ pH 8.0, 0.3 M NaCl, 5 mM β-mercaptoethanol, 10% glycerol, 0.05% octyl glucoside, 1 mM EDTA, 1 mM PMSF, 0.1 µM pepstatin, 1 µM leupeptin. Cell debris was removed by centrifugation at 30100×g for 30 min at 4° C. The supernatant was discarded and the pellet retained.

Protein was extracted from the pellet as follows. 6 ml/g extraction buffer was added and rocked at room temperature for 15 min. The extraction buffer consisted of 50 mM Tris pH 8.0, 1 M NaCl, 5 mM β-mercaptoethanol, 10% glycerol, 1 mM EDTA, 1 mM PMSF, 0.1 µM pepstatin, 1 µM leupeptin. This was centrifuged at 30100×g for 30 min at 4° C. The supernatant was retained and ammonium sulfate added to 17.5% using the following formula: volume of supernatant (ml) multiplied by x % ammonium sulfate/(1-x % ammonium sulfate)=ml of 4.1 M saturated ammonium sulfate to add to the supernatant. The ammonium sulfate was added dropwise while stirring on ice and the solution stirred on ice for 10 min. The solution was centrifuged at 17700×g for 30 min at 4° C. and the pellet retained and stored at 2° C. to 8° C. for up to 48 hrs.

The pellet was resuspended and run on a Poly U column (Poly U Sepharose 4B, Amersham Pharmacia) at 4° C. as follows. Pellet was resuspended in 6 ml Poly U equilibration buffer per gram of pellet weight. The equilibration buffer consisted of 25 mM HEPES pH 8.0, 200 mM NaCl, 5 mM DTT (added fresh), 10% glycerol, 1.2 octyl glucoside. The solution was rocked at 4°C for 15 min and centrifuged at 31000×g for 30 min at 4° C.

A Poly U column (1 ml resin per gram start pellet weight) was prepared. Linear flow rate was 60 cm/hr and packing flow rate was 133% of 60 cm/hr. The column was equilibrated with equilibration buffer and the supernatant of the resuspended ammonium sulfate pellet was loaded onto the equilibrated column. The column was washed to baseline with the equilibration buffer and protein eluted with a step elution in the following Poly U elution buffer: 25 mM HEPES pH 8.0, 1 M NaCl, 5 mM DTT (added fresh), 10% glycerol, 1.2 octyl glucoside. Column eluate was run on SDS-PAGE (Coomassie stained) and aliquots frozen and stored at −80° C. The presence of the NS3/4a epitope was confirmed by Western blot, using a polyclonal antibody directed against the NS3 protease domain and a monoclonal antibody against the 5-1-1 epitope (HCV 4a).

Additionally, protease enzyme activity was monitored during purification as follows. An NS4A peptide (KKGSV-VIVGRIVLSGKPAIIPKK) (SEQ ID NO: 9), and the sample containing the NS3/4a conformational epitope, were diluted in 90 µl of reaction buffer (25 mM Tris, pH 7.5, 0.15M NaCl, 0.5 mM EDTA, 10% glycerol, 0.05 n-Dodecyl B-D-Maltoside, 5 mM DTT) and allowed to mix for 30 minutes at room temperature. 90 µl of the mixture were added to a microtiter plate (Costar, Inc., Corning, N.Y.) and 10 µl of HCV substrate (AnaSpec, Inc., San Jose Calif.) was added. The plate was mixed and read on a Fluostar plate reader. Results were expressed as relative fluorescence units (RFU) per minute.

Using these methods, the product of the 1 M NaCl extraction contained 3.7 RFU/min activity, the ammonium sulfate precipitate had an activity of 7.5 RFU/min and the product of the Poly U purification had an activity of 18.5 RFU/min.

EXAMPLE 3

Immunoreactivity of NS3/4a Conformational Epitope Verus Denatured NS3/4a

The immunoreactivity of the NS3/4a conformational epitope, produced as described above, was compared to NS3/4a which had been denatured by adding SDS to the NS3/4a conformational epitope preparation to a final concentration of 2%. The denatured NS3/4a and conformational NS3/4a were coated onto microtiter plates as described above. The c200 antigen (Hepatology (1992) 15:19–25, available in the ORTHO HCV Version 3.0 ELISA Test System, Ortho-Clinical Diagnostics, Raritan, N.J.) was also coated onto microtiter plates. The c200 antigen was used as a comparison it is presumed to be non-conformational due to the presence of reducing agent (DTT) and detergent (SDS) in its formulation.

The immunoreactivity was tested against two early HCV seroconversion panels, PHV 904 and PHV 914 (commercially available human blood samples from Boston Biomedica, Inc., West Bridgewater, Mass.). The results are shown in Table 6. The data suggest that the denatured or linearized form of NS3/4a (as well as c200) does not detect early seroconversion panels as early as the NS3/4a conformational epitope.

NS3/4a in a similar manner to the seroconversion panels shown in Table 7. This result also provides further evidence that the NS3/4a is conformational in nature as monoclonal antibodies can be made which are similar in reactivity to the early c33c seroconversion panels.

TABLE 7

| Monoclonal | | NS3/4a OD | dNS3/4a OD | c200 OD |
|---|---|---|---|---|
| 4B9/E3 | 1:100 | 1.820 | 0.616 | 0.369 |
| | 1:1000 | 1.397 | 0.380 | 0.246 |
| | 1:10000 | 0.864 | 0.173 | 0.070 |
| | 1:20000 | 0.607 | 0.116 | 0.085 |
| 5B7/D7 | 1:100 | 2.885 | 0.898 | 0.436 |
| | 1:1000 | 2.866 | 0.541 | 0.267 |
| | 1:10000 | 1.672 | 0.215 | 0.086 |
| | 1:20000 | 1.053 | 0.124 | 0.059 |
| 1A8/H2 | 1:100 | 1.020 | 0.169 | 0.080 |
| | 1:1000 | 0.921 | 0.101 | 0.043 |
| | 1:10000 | 0.653 | 0.037 | 0.013 |
| | 1:20000 | 0.337 | 0.027 | 0.011 |

EXAMPLE 4

Coating Solid Support with the HCV Antigens

The HCV NS3/4a conformational epitope or MEFA antigen is coated onto plates as follows. HCV coating buffer (50 mM NaPO4 pH 7.0, 2 mM EDTA and 0.1% Chloroacetamide) is filtered through a 0.22μ filter unit. The following

TABLE 6

NS3/4a vs. denatured NS3/4a

| | | NS3/4a OD | dNS3/4a* OD | c200 OD | NS3/4a s/co | dNS3/4a* s/co | c200 s/co |
|---|---|---|---|---|---|---|---|
| HCV Seroconversions | PHV 904-1 | 0.012 | 0.012 | 0.009 | 0.02 | 0.02 | 0.01 |
| | PHV 904-2 | 0.011 | 0.009 | 0.008 | 0.02 | 0.01 | 0.01 |
| | PHV 904-3 | 1.124 | 0.071 | 0.045 | 1.80 | 0.11 | 0.07 |
| | PHV 904-4 | 2.401 | 0.273 | 0.129 | 3.85 | 0.44 | 0.21 |
| | PHV 904-5 | 3.022 | 0.793 | 0.347 | 4.85 | 1.28 | 0.57 |
| | PHV 904-6 | 2.711 | 1.472 | 0.774 | 4.35 | 2.37 | 1.28 |
| | PHV 904-7 | 3.294 | 1.860 | 0.943 | 5.28 | 2.99 | 1.55 |
| | PHV 914-1 | 0.006 | 0.004 | 0.001 | 0.01 | 0.01 | 0.00 |
| | PHV 914-2 | 0.005 | 0.004 | 0.002 | 0.01 | 0.01 | 0.00 |
| | PHV 914-3 | 0.098 | 0.003 | 0.001 | 0.16 | 0.00 | 0.00 |
| | PHV 914-4 | 1.118 | 0.006 | 0.004 | 1.79 | 0.01 | 0.01 |
| | PHV 914-5 | 2.035 | 0.044 | 0.022 | 3.26 | 0.07 | 0.04 |
| | PHV 914-6 | 2.092 | 0.074 | 0.025 | 3.35 | 0.12 | 0.04 |
| | PHV 914-7 | 2.519 | 0.281 | 0.132 | 4.04 | 0.45 | 0.22 |
| | PHV 914-8 | 2.746 | 0.907 | 0.500 | 4.40 | 1.46 | 0.82 |
| | PHV 914-9 | 3.084 | 1.730 | 0.931 | 4.94 | 2.78 | 1.53 |
| HCV 3.0 Controls | Neg. Cont. | 0.023 | 0.024 | 0.008 | | | |
| | Neg. Cont. | 0.027 | 0.024 | 0.007 | | | |
| | Neg. Cont. | 0.021 | 0.017 | 0.005 | | | |
| | average | 0.024 | 0.022 | 0.007 | | | |
| | cutoff | 0.624 | 0.622 | 0.607 | | | |
| | Pos. Cont. | 1.239 | 0.903 | 0.575 | 1.99 | 1.45 | 0.95 |
| | Pos. Cont. | 1.445 | 0.916 | 0.614 | 2.32 | 1.47 | 1.01 |

*Spiked 2% SDS to stock NS3/4a

Immunoreactivity of the conformational epitope was also tested using monoclonal antibodies to NS3/4a, made using standard procedures. These monoclonal antibodies were then tested in the ELISA format against NS3/4a and denatured NS3/4a and c200 antigen. The data show that anti-NS3/4a monoclonals react to the NS3/4a and denatured reagents are then added sequentially to the HCV coating buffer and stirred after each addition: 2 μg/ml BSA-Sulfhydryl Modified, from a 10 mg/ml solution (Bayer Corp. Pentex, Kankakee, Ill.); 5 mM DTT from a 1 M solution (Sigma, St. Louis, Mo.); 0.45 μg/ml NS3/4a (protein concentration of 0.3 mg/ml); or 0.375 μg/ml MEFA 7.1 (protein concentration of 1 mg/ml). The final solution is stirred for 15 minutes at room temperature.

200 µl of the above solution is added to each well of a Costar high binding, flat bottom plate (Corning Inc., Corning, N.Y.) and the plates are incubated overnight in a moisture chamber. The plates are then washed with wash buffer (1×PBS, 0.1% TWEEN-20), Tapped dry and 285 µl Ortho Post-Coat Buffer (1×PBS, pH 7.4, 1% BSA, 3% sucrose) added. The plates are incubated for at least 1 hour, tapped and dried overnight at 2–8° C. The plates are pouched with desiccants for future use.

EXAMPLE 5

Immunoassays

In order to test the ability of the subject immunoassays to detect HCV infection, panels of commercially available human blood samples are used which are HCV-infected. Such panels are commercially available from Boston Biomedica, Inc., West Bridgewater, Mass. (BBI); Bioclinical Partners, Franklin, Mass. (BCP); and North American Biologics, Inc., BocoRatan, Fla. (NABI).

The assay is conducted as follows. 200 µl of specimen diluent buffer (1 g/l casein, 100 mg/l recombinant human SOD, 1 g/l chloracetamide, 10 g/l BSA, 500 mg/l yeast extract, 0.366 g/l EDTA, 1.162 g/l $KPO_4$, 5 ml/l Tween-20, 29.22 g/l NaCl, 1.627 g/l $NaPO_4$, 1% SDS) is added to the coated plates. 20 µl of sample is then added. This is incubated at 37° C. for 30–60 minutes. The plates are washed with wash buffer (1×PBS, pH 7.4, 0.1% Tween-20). 200 µl of the labeled solution-phase component (either HRP-labeled MEFA or HRP-labeled NS3/4a conformational epitope, depending on the antigen bound to the solid support), diluted 1:22,000 in ORTHO HCV 3.0 ELISA Test System with Enhanced SAVe bulk conjugate diluent (Ortho-Clinical Diagnostics, Raritan, N.J.) is added and incubated for 30–60 minutes at 37□C. This is washed as above, and 200 µl substrate solution (1 OPD tablet/10 ml) is added. The OPD tablet contains o-phenylenediamine dihydrochloride and hydrogen peroxide for horse radish peroxidase reaction color development. This is incubated for 30 minutes at room temperature in the dark. The reaction is stopped by addition of 50 µl 4N $H_2SO_4$ and the plates are read at 492 nm, relative to absorbance at 690 nm as control.

Accordingly, novel HCV detection assays have been disclosed. From the foregoing, it will be appreciated that, although specific embodiments of the invention have been described herein for purposes of illustration, various modifications may be made without deviating from the spirit and scope of the disclosure herein.

The invention claimed is:

1. A method of detecting hepatitis C virus (HCV) infection in a biological sample, said method comprising:
   (a) providing an immunoassay solid support comprising HCV antigens bound thereto, wherein the HCV antigens consist of one or more HCV NS3/4a antigens wherein at least one of the NS3/4a antigens comprises a conformational epitope and comprises amino acids 2–686 of SEQ IDNO:2;
   (b) combining a biological sample with said solid support under conditions which allow HCV antibodies, when present in the biological sample, to bind to said one or more NS3/4a antigens;
   (c) adding to the solid support from step (b) under complex-forming conditions a detectably labeled HCV multiple epitope fusion antigen (MEFA), wherein said labeled MEFA comprises at least one epitope from the HCV NS3/4a region and a consensus sequence from the E2 hypervariable region spanning amino acids 390–410 having the sequence of SEQ ID NO:7, wherein said MEFA binds said bound HCV antibody;
   (d) detecting complexes formed between said HCV antibody and said NS3/4a antigen and said MEFA, if any, as an indication of HCV infection in the biological sample.

2. The method of claim 1, wherein at least one of said NS3/4a antigens consists of the amino acid sequence of SEQ ID NO:2.

3. The method of claim 1, wherein said MEFA comprises an epitope from the NS3/4a protease region of the HCV polyprotein.

4. The method of claim 1, wherein said MEFA comprises an epitope from the NS3/4a helicase region of the HCV polyprotein.

5. The method of claim 4, wherein said MEFA comprises amino acids 1193–1657, numbered relative to the HCV-1 sequence.

6. The method of claim 1, wherein said MEFA comprises an epitope from the c33c region of the HCV polyprotein.

7. The method of claim 6, wherein said MEFA comprises amino acids 1211–1457, numbered relative to HCV-1.

8. The method of claim 6, wherein said MEFA comprises amino acids 1192–1457, numbered relative to HCV-1.

9. The method of claim 1, wherein said MEFA comprises an epitope from the 5-1-1 region of the HCV polyprotein.

10. The method of claim 9, wherein said MEFA comprises amino acids 1689–1735, numbered relative to HCV-1.

11. The method of claim 1, wherein said MEFA comprises the amino acid sequence of SEQ ID NO:4.

12. The method of claim 1, wherein said MEFA comprises the amino acid sequence of SEQ ID NO:6.

13. A method of detecting hepatitis C virus (HCV) infection in a biological sample, said method comprising:
   (a) providing an immunoassay solid support comprising HCV antigens bound thereto, wherein the HCV antigens consist of one or more multiple epitope fusion antigens (MEFAs) wherein said one or more MEFAS comprise at least one epitope from the HCV NS3/4a region and a consensus sequence from the E2 hypervariable region spanning amino acids 390–410 having the sequence of SEQ ID NO:7;
   (b) combining a biological sample with said solid support under conditions which allow HCV antibodies, when present in the biological sample, to bind to said one or more MEFAs;
   (c) adding to the solid support from step (b) under complex-forming conditions a detectably labeled HCV NS3/4a antigen comprising a conformational epitope, wherein said detectably labeled NS3/4a antigen binds said bound HCV antibody, and further wherein said NS3/4a antigen comprises amino acids 2–686 of SEQ ID NO:2;
   (d) detecting complexes formed between said HCV antibody and said detectably labeled NS3/4a antigen and said MEFA, if any, as an indication of HCV infection in the biological sample.

14. The method of claim 13, wherein said detectably labeled NS3/4a antigen consists of a detectable label and the amino acid sequence of SEQ ID NO:2.

15. The method of claim 13, wherein said MEFA comprises an epitope from the NS3/4a protease region of the HCV polyprotein.

16. The method of claim 13, wherein said MEFA comprises an epitope from the NS3/4a helicase region of the HCV polyprotein.

17. The method of claim 16, wherein said MEFA comprises amino acids 1193–1657, numbered relative to the HCV-1 sequence.

18. The method of claim 13, wherein said MEFA comprises an epitope from the c33c region of the HCV polyprotein.

19. The method of claim 18, wherein said MEFA comprises amino acids 1211–1457, numbered relative to HCV-1.

20. The method of claim 18, wherein said MEFA comprises amino acids 1192–1457, numbered relative to HCV-1.

21. The method of claim 13, wherein said MEFA comprises an epitope from the 5-1-1 region of the HCV polyprotein.

22. The method of claim 21, wherein said MEFA comprises amino acids 1689–1735, numbered relative to HCV-1.

23. The method of claim 13, wherein said MEFA comprises the amino acid sequence of SEQ ID NO:4.

24. The method of claim 13, wherein said MEFA comprises the amino acid sequence of SEQ ID NO:6.

25. The method of claim 1, wherein said MEFA is MEFA 13 or MEFA 13.1.

26. The method of claim 13, wherein said MEFA is MEFA 13 or MEFA 13.1.

* * * * *

SEQUENCE LISTING

<160> NUMBER OF SEQ ID NOS: 9

<210> SEQ ID NO 1
<211> LENGTH: 2058
<212> TYPE: DNA
<213> ORGANISM: Artificial
<220> FEATURE:
<223> OTHER INFORMATION: NS3/41 conformational epitope DNA sequence

<400> SEQUENCE: 1

```
atg gcg ccc atc acg gcg tac gcc cag cag aca agg ggc ctc cta ggg        48
Met Ala Pro Ile Thr Ala Tyr Ala Gln Gln Thr Arg Gly Leu Leu Gly
 1               5                  10                  15 tgc ata atc acc agc cta act ggc cgg gac aaa aac caa gtg gag ggt        96
Cys Ile Ile Thr Ser Leu Thr Gly Arg Asp Lys Asn Gln Val Glu Gly
            20                  25                  30 gag gtc cag att gtg tca act gct gcc caa acc ttc ctg gca acg tgc       144
Glu Val Gln Ile Val Ser Thr Ala Ala Gln Thr Phe Leu Ala Thr Cys
        35                  40                  45 atc aat ggg gtg tgc tgg act gtc tac cac ggg gcc gga acg agg acc       192
Ile Asn Gly Val Cys Trp Thr Val Tyr His Gly Ala Gly Thr Arg Thr
    50                  55                  60 atc gcg tca ccc aag ggt cct gtc atc cag atg tat acc aat gta gac       240
Ile Ala Ser Pro Lys Gly Pro Val Ile Gln Met Tyr Thr Asn Val Asp
65                  70                  75                  80 caa gac ctt gtg ggc tgg ccc gct ccg caa ggt agc cga tca ttg aca       288
Gln Asp Leu Val Gly Trp Pro Ala Pro Gln Gly Ser Arg Ser Leu Thr
                85                  90                  95 ccc tgc act tgc ggc tcc tcg gac ctt tac ctg gtc acg agg cac gcc       336
Pro Cys Thr Cys Gly Ser Ser Asp Leu Tyr Leu Val Thr Arg His Ala
            100                 105                 110 gat gtc att ccc gtg cgc cgg cgg ggt gat agc agg ggc agc ctg ctg       384
Asp Val Ile Pro Val Arg Arg Arg Gly Asp Ser Arg Gly Ser Leu Leu
        115                 120                 125
```

```
tcg ccc cgg ccc att tcc tac ttg aaa ggc tcc tcg ggg ggt ccg ctg       432
Ser Pro Arg Pro Ile Ser Tyr Leu Lys Gly Ser Ser Gly Gly Pro Leu
    130                 135                 140 ttg tgc ccc gcg ggg cac gcc gtg ggc ata ttt agg gcc gcg gtg tgc       480
Leu Cys Pro Ala Gly His Ala Val Gly Ile Phe Arg Ala Ala Val Cys
145                 150                 155                 160 acc cgt gga gtg gct aag gcg gtg gac ttt atc cct gtg gag aac cta       528
Thr Arg Gly Val Ala Lys Ala Val Asp Phe Ile Pro Val Glu Asn Leu
                165                 170                 175 gag aca acc atg agg tcc ccg gtg ttc acg gat aac tcc tct cca cca       576
Glu Thr Thr Met Arg Ser Pro Val Phe Thr Asp Asn Ser Ser Pro Pro
            180                 185                 190 gta gtg ccc cag agc ttc cag gtg gct cac ctc cat gct ccc aca ggc       624
Val Val Pro Gln Ser Phe Gln Val Ala His Leu His Ala Pro Thr Gly
        195                 200                 205 agc ggc aaa agc acc aag gtc ccg gct gca tat gca gct cag ggc tat       672
Ser Gly Lys Ser Thr Lys Val Pro Ala Ala Tyr Ala Ala Gln Gly Tyr
    210                 215                 220 aag gtg cta gta ctc aac ccc tct gtt gct gca aca ctg ggc ttt ggt       720
Lys Val Leu Val Leu Asn Pro Ser Val Ala Ala Thr Leu Gly Phe Gly
225                 230                 235                 240 gct tac atg tcc aag gct cat ggg atc gat cct aac atc agg acc ggg       768
Ala Tyr Met Ser Lys Ala His Gly Ile Asp Pro Asn Ile Arg Thr Gly
                245                 250                 255 gtg aga aca att acc act ggc agc ccc atc acg tac tcc acc tac ggc       816
Val Arg Thr Ile Thr Thr Gly Ser Pro Ile Thr Tyr Ser Thr Tyr Gly
            260                 265                 270 aag ttc ctt gcc gac ggc ggg tgc tcg ggg ggc gct tat gac ata ata       864
Lys Phe Leu Ala Asp Gly Gly Cys Ser Gly Gly Ala Tyr Asp Ile Ile
        275                 280                 285 att tgt gac gag tgc cac tcc acg gat gcc aca tcc atc ttg ggc att       912
Ile Cys Asp Glu Cys His Ser Thr Asp Ala Thr Ser Ile Leu Gly Ile
    290                 295                 300 ggc act gtc ctt gac caa gca gag act gcg ggg gcg aga ctg gtt gtg       960
Gly Thr Val Leu Asp Gln Ala Glu Thr Ala Gly Ala Arg Leu Val Val
305                 310                 315                 320 ctc gcc acc gcc acc cct ccg ggc tcc gtc act gtg ccc cat ccc aac      1008
Leu Ala Thr Ala Thr Pro Pro Gly Ser Val Thr Val Pro His Pro Asn
                325                 330                 335 atc gag gag gtt gct ctg tcc acc acc gga gag atc cct ttt tac ggc      1056
Ile Glu Glu Val Ala Leu Ser Thr Thr Gly Glu Ile Pro Phe Tyr Gly
            340                 345                 350 aag gct atc ccc ctc gaa gta atc aag ggg ggg aga cat ctc atc ttc      1104
Lys Ala Ile Pro Leu Glu Val Ile Lys Gly Gly Arg His Leu Ile Phe
        355                 360                 365 tgt cat tca aag aag aag tgc gac gaa ctc gcc gca aag ctg gtc gca      1152
Cys His Ser Lys Lys Lys Cys Asp Glu Leu Ala Ala Lys Leu Val Ala
    370                 375                 380 ttg ggc atc aat gcc gtg gcc tac tac cgc ggt ctt gac gtg tcc gtc      1200
Leu Gly Ile Asn Ala Val Ala Tyr Tyr Arg Gly Leu Asp Val Ser Val
385                 390                 395                 400 atc ccg ccc atc ggc gat gtt gtc gtc gtg gca acc gat gcc ctc atg      1248
Ile Pro Pro Ile Gly Asp Val Val Val Val Ala Thr Asp Ala Leu Met
                405                 410                 415 acc ggc tat acc ggc gac ttc gac tcg gtg ata gac tgc aat acg tgt      1296
Thr Gly Tyr Thr Gly Asp Phe Asp Ser Val Ile Asp Cys Asn Thr Cys
            420                 425                 430 gtc acc cag aca gtc gat ttc agc ctt gac cct acc ttc acc att gag      1344
Val Thr Gln Thr Val Asp Phe Ser Leu Asp Pro Thr Phe Thr Ile Glu
        435                 440                 445
```

```
aca atc acg ctc ccc caa gat gct gtc tcc cgc act caa cgt cgg ggc      1392
Thr Ile Thr Leu Pro Gln Asp Ala Val Ser Arg Thr Gln Arg Arg Gly
    450                 455                 460 agg act ggc agg ggg aag cca ggc atc tac aga ttt gtg gca ccg ggg      1440
Arg Thr Gly Arg Gly Lys Pro Gly Ile Tyr Arg Phe Val Ala Pro Gly
465                 470                 475                 480 gag cgc ccc tcc ggc atg ttc gac tcg tcc gtc ctc tgt gag tgc tat      1488
Glu Arg Pro Ser Gly Met Phe Asp Ser Ser Val Leu Cys Glu Cys Tyr
                485                 490                 495 gac gca ggc tgt gct tgg tat gag ctc acg ccc gcc gag act aca gtt      1536
Asp Ala Gly Cys Ala Trp Tyr Glu Leu Thr Pro Ala Glu Thr Thr Val
            500                 505                 510 agg cta cga gcg tac atg aac acc ccg ggg ctt ccc gtg tgc cag gac      1584
Arg Leu Arg Ala Tyr Met Asn Thr Pro Gly Leu Pro Val Cys Gln Asp
        515                 520                 525 cat ctt gaa ttt tgg gag ggc gtc ttt aca ggc ctc act cat ata gat      1632
His Leu Glu Phe Trp Glu Gly Val Phe Thr Gly Leu Thr His Ile Asp
    530                 535                 540 gcc cac ttt cta tcc cag aca aag cag agt ggg gag aac ctt cct tac      1680
Ala His Phe Leu Ser Gln Thr Lys Gln Ser Gly Glu Asn Leu Pro Tyr
545                 550                 555                 560 ctg gta gcg tac caa gcc acc gtg tgc gct agg gct caa gcc cct ccc      1728
Leu Val Ala Tyr Gln Ala Thr Val Cys Ala Arg Ala Gln Ala Pro Pro
                565                 570                 575 cca tcg tgg gac cag atg tgg aag tgt ttg att cgc ctc aag ccc acc      1776
Pro Ser Trp Asp Gln Met Trp Lys Cys Leu Ile Arg Leu Lys Pro Thr
            580                 585                 590 ctc cat ggg cca aca ccc ctg cta tac aga ctg ggc gct gtt cag aat      1824
Leu His Gly Pro Thr Pro Leu Leu Tyr Arg Leu Gly Ala Val Gln Asn
        595                 600                 605 gaa atc acc ctg acg cac cca gtc acc aaa tac atc atg aca tgc atg      1872
Glu Ile Thr Leu Thr His Pro Val Thr Lys Tyr Ile Met Thr Cys Met
    610                 615                 620 tcg gcc gac ctg gag gtc gtc acg agc acc tgg gtg ctc gtt ggc ggc      1920
Ser Ala Asp Leu Glu Val Val Thr Ser Thr Trp Val Leu Val Gly Gly
625                 630                 635                 640 gtc ctg gct gct ttg gcc gcg tat tgc ctg tca aca ggc tgc gtg gtc      1968
Val Leu Ala Ala Leu Ala Ala Tyr Cys Leu Ser Thr Gly Cys Val Val
                645                 650                 655 ata gtg ggc agg gtc gtc ttg tcc ggg aag ccg gca atc ata cct gac      2016
Ile Val Gly Arg Val Val Leu Ser Gly Lys Pro Ala Ile Ile Pro Asp
            660                 665                 670 agg gaa gtc ctc tac cga gag ttc gat gag atg gaa gag tgc                2058
Arg Glu Val Leu Tyr Arg Glu Phe Asp Glu Met Glu Glu Cys
        675                 680                 685

<210> SEQ ID NO 2
<211> LENGTH: 686
<212> TYPE: PRT
<213> ORGANISM: Artificial
<220> FEATURE:
<223> OTHER INFORMATION: NS3/41 conformational epitope amino acid
                        sequence

<400> SEQUENCE: 2

Met Ala Pro Ile Thr Ala Tyr Ala Gln Gln Thr Arg Gly Leu Leu Gly
  1               5                  10                  15

Cys Ile Ile Thr Ser Leu Thr Gly Arg Asp Lys Asn Gln Val Glu Gly
                 20                  25                  30

Glu Val Gln Ile Val Ser Thr Ala Ala Gln Thr Phe Leu Ala Thr Cys
```

```
                35                  40                  45
Ile Asn Gly Val Cys Trp Thr Val Tyr His Gly Ala Gly Thr Arg Thr
 50                  55                  60

Ile Ala Ser Pro Lys Gly Pro Val Ile Gln Met Tyr Thr Asn Val Asp
 65                  70                  75                  80

Gln Asp Leu Val Gly Trp Pro Ala Pro Gln Gly Ser Arg Ser Leu Thr
                 85                  90                  95

Pro Cys Thr Cys Gly Ser Ser Asp Leu Tyr Leu Val Thr Arg His Ala
                100                 105                 110

Asp Val Ile Pro Val Arg Arg Gly Asp Ser Arg Gly Ser Leu Leu
            115                 120                 125

Ser Pro Arg Pro Ile Ser Tyr Leu Lys Gly Ser Ser Gly Gly Pro Leu
130                 135                 140

Leu Cys Pro Ala Gly His Ala Val Gly Ile Phe Arg Ala Ala Val Cys
145                 150                 155                 160

Thr Arg Gly Val Ala Lys Ala Val Asp Phe Ile Pro Val Glu Asn Leu
                165                 170                 175

Glu Thr Thr Met Arg Ser Pro Val Phe Thr Asp Asn Ser Ser Pro Pro
                180                 185                 190

Val Val Pro Gln Ser Phe Gln Val Ala His Leu His Ala Pro Thr Gly
                195                 200                 205

Ser Gly Lys Ser Thr Lys Val Pro Ala Ala Tyr Ala Ala Gln Gly Tyr
        210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ser Pro Ile Thr Tyr Ser Thr Tyr Gly
                260                 265                 270

Lys Phe Leu Ala Asp Gly Gly Cys Ser Gly Gly Ala Tyr Asp Ile Ile
                275                 280                 285

Ile Cys Asp Glu Cys His Ser Thr Asp Ala Thr Ser Ile Leu Gly Ile
290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Thr Thr Gly Glu Ile Pro Phe Tyr Gly
                340                 345                 350

Lys Ala Ile Pro Leu Glu Val Ile Lys Gly Gly Arg His Leu Ile Phe
                355                 360                 365

Cys His Ser Lys Lys Cys Asp Glu Leu Ala Ala Lys Leu Val Ala
        370                 375                 380

Leu Gly Ile Asn Ala Val Ala Tyr Tyr Arg Gly Leu Asp Val Ser Val
385                 390                 395                 400

Ile Pro Pro Ile Gly Asp Val Val Val Ala Thr Asp Ala Leu Met
                405                 410                 415

Thr Gly Tyr Thr Gly Asp Phe Asp Ser Val Ile Asp Cys Asn Thr Cys
                420                 425                 430

Val Thr Gln Thr Val Asp Phe Ser Leu Asp Pro Thr Phe Thr Ile Glu
            435                 440                 445

Thr Ile Thr Leu Pro Gln Asp Ala Val Ser Arg Thr Gln Arg Arg Gly
450                 455                 460
```

```
Arg Thr Gly Arg Gly Lys Pro Gly Ile Tyr Arg Phe Val Ala Pro Gly
465                 470                 475                 480

Glu Arg Pro Ser Gly Met Phe Asp Ser Ser Val Leu Cys Glu Cys Tyr
            485                 490                 495

Asp Ala Gly Cys Ala Trp Tyr Glu Leu Thr Pro Ala Glu Thr Thr Val
        500                 505                 510

Arg Leu Arg Ala Tyr Met Asn Thr Pro Gly Leu Pro Val Cys Gln Asp
    515                 520                 525

His Leu Glu Phe Trp Glu Gly Val Phe Thr Gly Leu Thr His Ile Asp
530                 535                 540

Ala His Phe Leu Ser Gln Thr Lys Gln Ser Gly Glu Asn Leu Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Ile Thr Leu Thr His Pro Val Thr Lys Tyr Ile Met Thr Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Ser Thr Gly Cys Val Val
                645                 650                 655

Ile Val Gly Arg Val Val Leu Ser Gly Lys Pro Ala Ile Ile Pro Asp
            660                 665                 670

Arg Glu Val Leu Tyr Arg Glu Phe Asp Glu Met Glu Glu Cys
        675                 680                 685

<210> SEQ ID NO 3
<211> LENGTH: 2499
<212> TYPE: DNA
<213> ORGANISM: Artificial
<220> FEATURE:
<223> OTHER INFORMATION: MEFA 12 DNA sequence

<400> SEQUENCE: 3 atg gct aca aag gct gtt tgt gtt ttg aag ggt gac ggc cca gtt caa    48
Met Ala Thr Lys Ala Val Cys Val Leu Lys Gly Asp Gly Pro Val Gln
  1               5                  10                  15 ggt att att aac ttc gag cag aag gaa agt aat gga cca gtg aag gtg    96
Gly Ile Ile Asn Phe Glu Gln Lys Glu Ser Asn Gly Pro Val Lys Val
             20                  25                  30 tgg gga agc att aaa gga ctg act gaa ggc ctg cat gga ttc cat gtt   144
Trp Gly Ser Ile Lys Gly Leu Thr Glu Gly Leu His Gly Phe His Val
         35                  40                  45 cat gag ttt gga gat aat aca gca ggc tgt acc agt gca ggt cct cac   192
His Glu Phe Gly Asp Asn Thr Ala Gly Cys Thr Ser Ala Gly Pro His
     50                  55                  60 ttt aat cct cta tcc acg cgt ggt tgc aat tgc tct atc tat ccc ggc   240
Phe Asn Pro Leu Ser Thr Arg Gly Cys Asn Cys Ser Ile Tyr Pro Gly
 65                  70                  75                  80 cat ata acg ggt cac cgc atg gca tgg aag ctt ggt tcc gcc gcc aga   288
His Ile Thr Gly His Arg Met Ala Trp Lys Leu Gly Ser Ala Ala Arg
                 85                  90                  95 act acc tcg ggc ttt gtc tcc ttg ttc gcc cca ggt gcc aaa caa aac   336
Thr Thr Ser Gly Phe Val Ser Leu Phe Ala Pro Gly Ala Lys Gln Asn
            100                 105                 110
```

```
                100                 105                 110
gaa act cac gtc acg gga ggc gca gcc gcc cga act acg tct ggg ttg      384
Glu Thr His Val Thr Gly Gly Ala Ala Ala Arg Thr Thr Ser Gly Leu
            115                 120                 125 acc tct ttg ttc tcc cca ggt gcc agc caa aac att caa ttg att act      432
Thr Ser Leu Phe Ser Pro Gly Ala Ser Gln Asn Ile Gln Leu Ile Thr
        130                 135                 140 agt acg gat aac tcc tct cca cca gta gtg ccc cag agc ttc cag gtg      480
Ser Thr Asp Asn Ser Ser Pro Pro Val Val Pro Gln Ser Phe Gln Val
145                 150                 155                 160 gct cac ctc cat gct ccc aca ggc agc ggc aaa agc acc aag gtc ccg      528
Ala His Leu His Ala Pro Thr Gly Ser Gly Lys Ser Thr Lys Val Pro
                165                 170                 175 gct gca tat gca gct cag ggc tat aag gtg cta gta ctc aac ccc tct      576
Ala Ala Tyr Ala Ala Gln Gly Tyr Lys Val Leu Val Leu Asn Pro Ser
            180                 185                 190 gtt gct gca aca ctg ggc ttt ggt gct tac atg tcc aag gct cat ggg      624
Val Ala Ala Thr Leu Gly Phe Gly Ala Tyr Met Ser Lys Ala His Gly
        195                 200                 205 atc gat cct aac atc agg acc ggg gtg aga aca att acc act ggc agc      672
Ile Asp Pro Asn Ile Arg Thr Gly Val Arg Thr Ile Thr Thr Gly Ser
210                 215                 220 ccc atc acg tac tcc acc tac ggc aag ttc ctt gcc gac ggg ggg tgc      720
Pro Ile Thr Tyr Ser Thr Tyr Gly Lys Phe Leu Ala Asp Gly Gly Cys
225                 230                 235                 240 tcg ggg ggc gct tat gac ata ata att tgt gac gag tgc cac tcc acg      768
Ser Gly Gly Ala Tyr Asp Ile Ile Ile Cys Asp Glu Cys His Ser Thr
                245                 250                 255 gat gcc aca tcc atc ttg ggc atc ggc act gtc ctt gac caa gca gag      816
Asp Ala Thr Ser Ile Leu Gly Ile Gly Thr Val Leu Asp Gln Ala Glu
            260                 265                 270 act gcg ggg gcg aga ctg gtt gtg ctc gcc acc gcc acc cct ccg ggc      864
Thr Ala Gly Ala Arg Leu Val Val Leu Ala Thr Ala Thr Pro Pro Gly
        275                 280                 285 tcc gtc act gtg ccc cat ccc aac atc gag gag gtt gct ctg tcc acc      912
Ser Val Thr Val Pro His Pro Asn Ile Glu Glu Val Ala Leu Ser Thr
290                 295                 300 acc gga gag atc cct ttt tac ggc aag gct atc ccc ctc gaa gta atc      960
Thr Gly Glu Ile Pro Phe Tyr Gly Lys Ala Ile Pro Leu Glu Val Ile
305                 310                 315                 320 aag ggg ggg aga cat ctc atc ttc tgt cat tca aag aag aag tgc gac     1008
Lys Gly Gly Arg His Leu Ile Phe Cys His Ser Lys Lys Lys Cys Asp
                325                 330                 335 gaa ctc gcc gca aag ctg gtc gca ttg ggc atc aat gcc gtg gcc tac     1056
Glu Leu Ala Ala Lys Leu Val Ala Leu Gly Ile Asn Ala Val Ala Tyr
            340                 345                 350 tac cgc ggt ctt gac gtg tcc gtc atc ccg acc agc ggc gat gtt gtc     1104
Tyr Arg Gly Leu Asp Val Ser Val Ile Pro Thr Ser Gly Asp Val Val
        355                 360                 365 gtc gtg gca acc gat gcc ctc atg acc ggc tat acc ggc gac ttc gac     1152
Val Val Ala Thr Asp Ala Leu Met Thr Gly Tyr Thr Gly Asp Phe Asp
    370                 375                 380 tcg gtg ata gac tgc aat acg tgt gca tgc tcc ggg aag ccg gca atc     1200
Ser Val Ile Asp Cys Asn Thr Cys Ala Cys Ser Gly Lys Pro Ala Ile
385                 390                 395                 400 ata cct gac agg gaa gtc ctc tac cga gag ttc gat gag atg gaa gag     1248
Ile Pro Asp Arg Glu Val Leu Tyr Arg Glu Phe Asp Glu Met Glu Glu
                405                 410                 415 tgc tct cag cac tta ccg tac atc gag caa ggg atg atg ctc gcc gag     1296
```

|     |     |     |     |     |     |     |     |     |     |     |     |      |
| --- | --- | --- | --- | --- | --- | --- | --- | --- | --- | --- | --- | ---- |
| Cys | Ser | Gln | His | Leu | Pro | Tyr | Ile | Glu | Gln | Gly | Met | Met  Leu  Ala  Glu |
|     |     |     | 420 |     |     |     | 425 |     |     |     | 430 |      |

```
cag ttc aag cag aag gcc ctc ggc ctc tcg cga ggg ggc aag ccg gca      1344
Gln Phe Lys Gln Lys Ala Leu Gly Leu Ser Arg Gly Gly Lys Pro Ala
        435                 440                 445 atc gtt cca gac aaa gag gtg ttg tat caa caa tac gat gag atg gaa      1392
Ile Val Pro Asp Lys Glu Val Leu Tyr Gln Gln Tyr Asp Glu Met Glu
    450                 455                 460 gag tgc tca caa gct gcc cca tat atc gaa caa gct cag gta ata gct      1440
Glu Cys Ser Gln Ala Ala Pro Tyr Ile Glu Gln Ala Gln Val Ile Ala
465                 470                 475                 480 cac cag ttc aag gaa aaa gtc ctt gga ttg atc gat aat gat caa gtg      1488
His Gln Phe Lys Glu Lys Val Leu Gly Leu Ile Asp Asn Asp Gln Val
                485                 490                 495 gtt gtg act cct gac aaa gaa atc tta tat gag gcc ttt gat gag atg      1536
Val Val Thr Pro Asp Lys Glu Ile Leu Tyr Glu Ala Phe Asp Glu Met
            500                 505                 510 gaa gaa tgc gcc tcc aaa gcc gcc ctc att gag gaa ggg cag cgg atg      1584
Glu Glu Cys Ala Ser Lys Ala Ala Leu Ile Glu Glu Gly Gln Arg Met
        515                 520                 525 gcg gag atg ctc aag tct aag ata caa ggc ctc ctc ggg ata ctg cgc      1632
Ala Glu Met Leu Lys Ser Lys Ile Gln Gly Leu Leu Gly Ile Leu Arg
    530                 535                 540 cgg cac gtt ggt cct ggc gag ggg gca gtg cag tgg atg aac cgg ctg      1680
Arg His Val Gly Pro Gly Glu Gly Ala Val Gln Trp Met Asn Arg Leu
545                 550                 555                 560 ata gcc ttc gcc tcc aga ggg aac cat gtt tcc ccc acg cac tac gtt      1728
Ile Ala Phe Ala Ser Arg Gly Asn His Val Ser Pro Thr His Tyr Val
                565                 570                 575 ccg tct aga tcc cgg aga ttc gcc cag gcc ctg ccc gtt tgg gcg cgg      1776
Pro Ser Arg Ser Arg Arg Phe Ala Gln Ala Leu Pro Val Trp Ala Arg
            580                 585                 590 ccg gac tat aac ccc ccg cta gtg gag acg tgg aaa aag ccc gac tac      1824
Pro Asp Tyr Asn Pro Pro Leu Val Glu Thr Trp Lys Lys Pro Asp Tyr
        595                 600                 605 gaa cca cct gtg gtc cac ggc aga tct tct cgg aga ttc gcc cag gcc      1872
Glu Pro Pro Val Val His Gly Arg Ser Ser Arg Arg Phe Ala Gln Ala
    610                 615                 620 ctg ccc gtt tgg gcg cgg ccg gac tat aac ccc ccg cta gtg gag acg      1920
Leu Pro Val Trp Ala Arg Pro Asp Tyr Asn Pro Pro Leu Val Glu Thr
625                 630                 635                 640 tgg aaa aag ccc gac tac gaa cca cct gtg gtc cat ggc aga aag acc      1968
Trp Lys Lys Pro Asp Tyr Glu Pro Pro Val Val His Gly Arg Lys Thr
                645                 650                 655 aaa cgt aac acc aac cgg cgg ccg cag gac gtc aag ttc ccg ggt ggc      2016
Lys Arg Asn Thr Asn Arg Arg Pro Gln Asp Val Lys Phe Pro Gly Gly
            660                 665                 670 ggt cag atc gtt ggt gga gtt tac ttg ttg ccg cgc agg ggc cct aga      2064
Gly Gln Ile Val Gly Gly Val Tyr Leu Leu Pro Arg Arg Gly Pro Arg
        675                 680                 685 ttg ggt gtg ctc gcg acg aga aag act tcc cct atc ccc aag gct cgt      2112
Leu Gly Val Leu Ala Thr Arg Lys Thr Ser Pro Ile Pro Lys Ala Arg
    690                 695                 700 cgg ccc gag ggc agg acc tgg gct cag ccc ggt tac cct tgg ccc ctc      2160
Arg Pro Glu Gly Arg Thr Trp Ala Gln Pro Gly Tyr Pro Trp Pro Leu
705                 710                 715                 720 tat ggc aat aag gac aga cgg tct aca ggt aag tcc tgg ggt aag cca      2208
Tyr Gly Asn Lys Asp Arg Arg Ser Thr Gly Lys Ser Trp Gly Lys Pro
                725                 730                 735
```

-continued

```
ggg tac cct tgg cca aga aag acc aaa cgt aac acc aac cgg cgg ccg      2256
Gly Tyr Pro Trp Pro Arg Lys Thr Lys Arg Asn Thr Asn Arg Arg Pro
            740                 745                 750 cag gac gtc aag ttc ccg ggt ggc ggt cag atc gtt ggt gga gtt tac      2304
Gln Asp Val Lys Phe Pro Gly Gly Gly Gln Ile Val Gly Gly Val Tyr
        755                 760                 765 ttg ttg ccg cgc agg ggc cct aga ttg ggt gtg ctc gcg acg aga aag      2352
Leu Leu Pro Arg Arg Gly Pro Arg Leu Gly Val Leu Ala Thr Arg Lys
    770                 775                 780 act tcc cct atc ccc aag gct cgt cgg ccc gag ggc agg acc tgg gct      2400
Thr Ser Pro Ile Pro Lys Ala Arg Arg Pro Glu Gly Arg Thr Trp Ala
785                 790                 795                 800 cag ccc ggt tac cct tgg ccc ctc tat ggc aat aag gac aga cgg tct      2448
Gln Pro Gly Tyr Pro Trp Pro Leu Tyr Gly Asn Lys Asp Arg Arg Ser
                805                 810                 815 aca ggt aag tcc tgg ggt aag cca ggg tac cct tgg ccc taatgagtcg ac    2499
Thr Gly Lys Ser Trp Gly Lys Pro Gly Tyr Pro Trp Pro
            820                 825
```

<210> SEQ ID NO 4
<211> LENGTH: 829
<212> TYPE: PRT
<213> ORGANISM: Artificial
<220> FEATURE:
<223> OTHER INFORMATION: MEFA 12 amino acid sequence

<400> SEQUENCE: 4

```
Met Ala Thr Lys Ala Val Cys Val Leu Lys Gly Asp Gly Pro Val Gln
 1               5                  10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
        50                  55                  60

Phe Asn Pro Leu Ser Thr Arg Gly Cys Asn Cys Ser Ile Tyr Pro Gly
 65                  70                  75                  80

His Ile Thr Gly His Arg Met Ala Trp Lys Leu Gly Ser Ala Ala Arg
                85                  90                  95

Thr Thr Ser Gly Phe Val Ser Leu Phe Ala Pro Gly Ala Lys Gln Asn
            100                 105                 110

Glu Thr His Val Thr Gly Gly Ala Ala Ala Arg Thr Thr Ser Gly Leu
        115                 120                 125

Thr Ser Leu Phe Ser Pro Gly Ala Ser Gln Asn Ile Gln Leu Ile Thr
    130                 135                 140

Ser Thr Asp Asn Ser Ser Pro Pro Val Val Pro Gln Ser Phe Gln Val
145                 150                 155                 160

Ala His Leu His Ala Pro Thr Gly Ser Gly Lys Ser Thr Lys Val Pro
                165                 170                 175

Ala Ala Tyr Ala Ala Gln Gly Tyr Lys Val Leu Val Leu Asn Pro Ser
            180                 185                 190

Val Ala Ala Thr Leu Gly Phe Gly Ala Tyr Met Ser Lys Ala His Gly
        195                 200                 205

Ile Asp Pro Asn Ile Arg Thr Gly Val Arg Thr Ile Thr Thr Gly Ser
    210                 215                 220

Pro Ile Thr Tyr Ser Thr Tyr Gly Lys Phe Leu Ala Asp Gly Gly Cys
225                 230                 235                 240
```

-continued

```
Ser Gly Gly Ala Tyr Asp Ile Ile Ile Cys Asp Glu Cys His Ser Thr
            245                 250                 255

Asp Ala Thr Ser Ile Leu Gly Ile Gly Thr Val Leu Asp Gln Ala Glu
            260                 265                 270

Thr Ala Gly Ala Arg Leu Val Val Leu Ala Thr Ala Thr Pro Pro Gly
            275                 280                 285

Ser Val Thr Val Pro His Pro Asn Ile Glu Glu Val Ala Leu Ser Thr
            290                 295                 300

Thr Gly Glu Ile Pro Phe Tyr Gly Lys Ala Ile Pro Leu Glu Val Ile
305                 310                 315                 320

Lys Gly Gly Arg His Leu Ile Phe Cys His Ser Lys Lys Lys Cys Asp
                325                 330                 335

Glu Leu Ala Ala Lys Leu Val Ala Leu Gly Ile Asn Ala Val Ala Tyr
            340                 345                 350

Tyr Arg Gly Leu Asp Val Ser Val Ile Pro Thr Ser Gly Asp Val Val
            355                 360                 365

Val Val Ala Thr Asp Ala Leu Met Thr Gly Tyr Thr Gly Asp Phe Asp
370                 375                 380

Ser Val Ile Asp Cys Asn Thr Cys Ala Cys Ser Gly Lys Pro Ala Ile
385                 390                 395                 400

Ile Pro Asp Arg Glu Val Leu Tyr Arg Glu Phe Asp Glu Met Glu Glu
                405                 410                 415

Cys Ser Gln His Leu Pro Tyr Ile Glu Gln Gly Met Met Leu Ala Glu
            420                 425                 430

Gln Phe Lys Gln Lys Ala Leu Gly Leu Ser Arg Gly Gly Lys Pro Ala
            435                 440                 445

Ile Val Pro Asp Lys Glu Val Leu Tyr Gln Gln Tyr Asp Glu Met Glu
            450                 455                 460

Glu Cys Ser Gln Ala Ala Pro Tyr Ile Glu Gln Ala Gln Val Ile Ala
465                 470                 475                 480

His Gln Phe Lys Glu Lys Val Leu Gly Leu Ile Asp Asn Asp Gln Val
                485                 490                 495

Val Val Thr Pro Asp Lys Glu Ile Leu Tyr Glu Ala Phe Asp Glu Met
            500                 505                 510

Glu Glu Cys Ala Ser Lys Ala Ala Leu Ile Glu Glu Gly Gln Arg Met
            515                 520                 525

Ala Glu Met Leu Lys Ser Lys Ile Gln Gly Leu Leu Gly Ile Leu Arg
            530                 535                 540

Arg His Val Gly Pro Gly Glu Gly Ala Val Gln Trp Met Asn Arg Leu
545                 550                 555                 560

Ile Ala Phe Ala Ser Arg Gly Asn His Val Ser Pro Thr His Tyr Val
                565                 570                 575

Pro Ser Arg Ser Arg Arg Phe Ala Gln Ala Leu Pro Val Trp Ala Arg
            580                 585                 590

Pro Asp Tyr Asn Pro Pro Leu Val Glu Thr Trp Lys Lys Pro Asp Tyr
            595                 600                 605

Glu Pro Pro Val Val His Gly Arg Ser Ser Arg Phe Ala Gln Ala
            610                 615                 620

Leu Pro Val Trp Ala Arg Pro Asp Tyr Asn Pro Pro Leu Val Glu Thr
625                 630                 635                 640

Trp Lys Lys Pro Asp Tyr Glu Pro Pro Val Val His Gly Arg Lys Thr
                645                 650                 655

Lys Arg Asn Thr Asn Arg Arg Pro Gln Asp Val Lys Phe Pro Gly Gly
```

```
                        660                 665                 670
        Gly Gln Ile Val Gly Val Tyr Leu Leu Pro Arg Arg Gly Pro Arg
                    675                 680                 685

Leu Gly Val Leu Ala Thr Arg Lys Thr Ser Pro Ile Pro Lys Ala Arg
                    690                 695                 700

Arg Pro Glu Gly Arg Thr Trp Ala Gln Pro Gly Tyr Pro Trp Pro Leu
        705                 710                 715                 720

Tyr Gly Asn Lys Asp Arg Arg Ser Thr Gly Lys Ser Trp Gly Lys Pro
                        725                 730                 735

Gly Tyr Pro Trp Pro Arg Lys Thr Lys Arg Asn Thr Asn Arg Arg Pro
                    740                 745                 750

Gln Asp Val Lys Phe Pro Gly Gly Gln Ile Val Gly Gly Val Tyr
                    755                 760                 765

Leu Leu Pro Arg Arg Gly Pro Arg Leu Gly Val Leu Ala Thr Arg Lys
                    770                 775                 780

Thr Ser Pro Ile Pro Lys Ala Arg Arg Pro Glu Gly Arg Thr Trp Ala
        785                 790                 795                 800

Gln Pro Gly Tyr Pro Trp Pro Leu Tyr Gly Asn Lys Asp Arg Arg Ser
                        805                 810                 815

Thr Gly Lys Ser Trp Gly Lys Pro Gly Tyr Pro Trp Pro
                    820                 825

<210> SEQ ID NO 5
<211> LENGTH: 3297
<212> TYPE: DNA
<213> ORGANISM: Artificial
<220> FEATURE:
<223> OTHER INFORMATION: MEFA 7.1 DNA sequence

<400> SEQUENCE: 5 atg gct aca aag gct gtt tgt gtt ttg aag ggt gac ggc cca gtt caa       48
Met Ala Thr Lys Ala Val Cys Val Leu Lys Gly Asp Gly Pro Val Gln
1               5                   10                  15 ggt att att aac ttc gag cag aag gaa agt aat gga cca gtg aag gtg       96
Gly Ile Ile Asn Phe Glu Gln Lys Glu Ser Asn Gly Pro Val Lys Val
                20                  25                  30 tgg gga agc att aaa gga ctg act gaa ggc ctg cat gga ttc cat gtt      144
Trp Gly Ser Ile Lys Gly Leu Thr Glu Gly Leu His Gly Phe His Val
            35                  40                  45 cat gag ttt gga gat aat aca gca ggc tgt acc agt gca ggt cct cac      192
His Glu Phe Gly Asp Asn Thr Ala Gly Cys Thr Ser Ala Gly Pro His
        50                  55                  60 ttt aat cct cta tcc aga aaa cac ggt ggg cca aag gat gaa gag agg      240
Phe Asn Pro Leu Ser Arg Lys His Gly Gly Pro Lys Asp Glu Glu Arg
65                  70                  75                  80 cat gtt gga gac ttg ggc aat gtg act gct gac aaa gat ggt gtg gcc      288
His Val Gly Asp Leu Gly Asn Val Thr Ala Asp Lys Asp Gly Val Ala
                85                  90                  95 gat gtg tct att gaa gat tct gtg atc tca ctc tca gga gac cat tgc      336
Asp Val Ser Ile Glu Asp Ser Val Ile Ser Leu Ser Gly Asp His Cys
            100                 105                 110 atc att ggc cgc aca ctg gtg gtc cat gaa aaa gca gat gac ttg ggc      384
Ile Ile Gly Arg Thr Leu Val Val His Glu Lys Ala Asp Asp Leu Gly
        115                 120                 125 aaa ggt gga aat gaa gaa agt aca aag aca gga aac gct gga agt cgt      432
Lys Gly Gly Asn Glu Glu Ser Thr Lys Thr Gly Asn Ala Gly Ser Arg
    130                 135                 140 ttg gct tgt ggt gta att ggg atc gcc cag aat ttg aat tct ggt tgc      480
Leu Ala Cys Gly Val Ile Gly Ile Ala Gln Asn Leu Asn Ser Gly Cys
```

-continued

| | | |
|---|---|---|
| Leu Ala Cys Gly Val Ile Gly Ile Ala Gln Asn Leu Asn Ser Gly Cys<br>145                   150                   155                   160 | |
| aat tgc tct atc tat ccc ggc cat ata acg ggt cac cgc atg gca tgg<br>Asn Cys Ser Ile Tyr Pro Gly His Ile Thr Gly His Arg Met Ala Trp<br>               165                 170                 175 | 528 |
| aag ctt ggt tcc gcc gcc aga act acc tcg ggc ttt gtc tcc ttg ttc<br>Lys Leu Gly Ser Ala Ala Arg Thr Thr Ser Gly Phe Val Ser Leu Phe<br>        180                   185                 190 | 576 |
| gcc cca ggt gcc aaa caa aac gaa act cac gtc acg gga ggc gca gcc<br>Ala Pro Gly Ala Lys Gln Asn Glu Thr His Val Thr Gly Gly Ala Ala<br>        195                   200                 205 | 624 |
| gcc cga act acg tct ggg ttg acc tct ttg ttc tcc cca ggt gcc agc<br>Ala Arg Thr Thr Ser Gly Leu Thr Ser Leu Phe Ser Pro Gly Ala Ser<br>210                   215                   220 | 672 |
| caa aac att caa ttg att gtc gac ttt atc cct gtg gag aac cta gag<br>Gln Asn Ile Gln Leu Ile Val Asp Phe Ile Pro Val Glu Asn Leu Glu<br>225                   230                   235                 240 | 720 |
| aca acc atg cga tct ccg gtg ttc acg gat aac tcc tct cca cca gta<br>Thr Thr Met Arg Ser Pro Val Phe Thr Asp Asn Ser Ser Pro Pro Val<br>               245                 250                 255 | 768 |
| gtg ccc cag agc ttc cag gtg gct cac ctc cat gct ccc aca ggc agc<br>Val Pro Gln Ser Phe Gln Val Ala His Leu His Ala Pro Thr Gly Ser<br>        260                   265                 270 | 816 |
| ggc aaa agc acc aag gtc ccg gct gca tat gca gct cag ggc tat aag<br>Gly Lys Ser Thr Lys Val Pro Ala Ala Tyr Ala Ala Gln Gly Tyr Lys<br>        275                   280                 285 | 864 |
| gtg cta gta ctc aac ccc tct gtt gct gca aca ctg ggc ttt ggt gct<br>Val Leu Val Leu Asn Pro Ser Val Ala Ala Thr Leu Gly Phe Gly Ala<br>290                   295                   300 | 912 |
| tac atg tcc aag gct cat ggg atc gat cct aac atc agg acc ggg gtg<br>Tyr Met Ser Lys Ala His Gly Ile Asp Pro Asn Ile Arg Thr Gly Val<br>305                   310                   315                 320 | 960 |
| aga aca att acc act ggc agc ccc atc acg tac tcc acc tac ggc aag<br>Arg Thr Ile Thr Thr Gly Ser Pro Ile Thr Tyr Ser Thr Tyr Gly Lys<br>               325                 330                 335 | 1008 |
| ttc ctt gcc gac ggc ggg tgc tcg ggg ggc gct tat gac ata ata att<br>Phe Leu Ala Asp Gly Gly Cys Ser Gly Gly Ala Tyr Asp Ile Ile Ile<br>        340                   345                 350 | 1056 |
| tgt gac gag tgc cac tcc acg gat gcc aca tcc atc ttg ggc att ggc<br>Cys Asp Glu Cys His Ser Thr Asp Ala Thr Ser Ile Leu Gly Ile Gly<br>        355                   360                 365 | 1104 |
| act gtc ctt gac caa gca gag act gcg ggg gcg aga ctg gtt gtg ctc<br>Thr Val Leu Asp Gln Ala Glu Thr Ala Gly Ala Arg Leu Val Val Leu<br>370                   375                   380 | 1152 |
| gcc acc gcc acc cct ccg ggc tcc gtc act gtg ccc cat ccc aac atc<br>Ala Thr Ala Thr Pro Pro Gly Ser Val Thr Val Pro His Pro Asn Ile<br>385                   390                   395                 400 | 1200 |
| gag gag gtt gct ctg tcc acc acc gga gag atc cct ttt tac ggc aag<br>Glu Glu Val Ala Leu Ser Thr Thr Gly Glu Ile Pro Phe Tyr Gly Lys<br>               405                 410                 415 | 1248 |
| gct atc ccc ctc gaa gta atc aag ggg ggg aga cat ctc atc ttc tgt<br>Ala Ile Pro Leu Glu Val Ile Lys Gly Gly Arg His Leu Ile Phe Cys<br>        420                   425                 430 | 1296 |
| cat tca aag aag aag tgc gac gaa ctc gcc gca aag ctg gtc gca ttg<br>His Ser Lys Lys Lys Cys Asp Glu Leu Ala Ala Lys Leu Val Ala Leu<br>        435                   440                 445 | 1344 |
| ggc atc aat gcc gtg gcc tac tac cgc ggt ctt gac gtg tcc gtc atc<br>Gly Ile Asn Ala Val Ala Tyr Tyr Arg Gly Leu Asp Val Ser Val Ile<br>450                     455                   460 | 1392 |

```
ccg acc agc ggc gat gtt gtc gtc gtg gca acc gat gcc ctc atg acc    1440
Pro Thr Ser Gly Asp Val Val Val Val Ala Thr Asp Ala Leu Met Thr
465                 470                 475                 480 ggc tat acc ggc gac ttc gac tcg gtg ata gac tgc aat acg tgt gtc    1488
Gly Tyr Thr Gly Asp Phe Asp Ser Val Ile Asp Cys Asn Thr Cys Val
                485                 490                 495 acc cag aca gtc gat ttc agc ctt gac cct acc ttc acc att gag aca    1536
Thr Gln Thr Val Asp Phe Ser Leu Asp Pro Thr Phe Thr Ile Glu Thr
            500                 505                 510 atc acg ctc ccc caa gat gct gtc tcc cgc act caa cgt cgg ggc agg    1584
Ile Thr Leu Pro Gln Asp Ala Val Ser Arg Thr Gln Arg Arg Gly Arg
        515                 520                 525 act ggc agg ggg aag cca ggc atc tac aga ttt gtg gca ccg ggg gag    1632
Thr Gly Arg Gly Lys Pro Gly Ile Tyr Arg Phe Val Ala Pro Gly Glu
    530                 535                 540 cgc ccc tcc ggc atg ttc gac tcg tcc gtc ctc tgt gag tgc tat gac    1680
Arg Pro Ser Gly Met Phe Asp Ser Ser Val Leu Cys Glu Cys Tyr Asp
545                 550                 555                 560 gca ggc tgt gct tgg tat gag ctc acg ccc gcc gag act aca gtt agg    1728
Ala Gly Cys Ala Trp Tyr Glu Leu Thr Pro Ala Glu Thr Thr Val Arg
                565                 570                 575 cta cga gcg tac atg aac acc ccg ggg ctt ccc gtg tgc cag gac cat    1776
Leu Arg Ala Tyr Met Asn Thr Pro Gly Leu Pro Val Cys Gln Asp His
            580                 585                 590 ctt gaa ttt tgg gag ggc gtc ttt aca ggc ctc act cat ata gat gcc    1824
Leu Glu Phe Trp Glu Gly Val Phe Thr Gly Leu Thr His Ile Asp Ala
        595                 600                 605 cac ttt cta tcc cag aca aag cag agt ggg gag aac ctt cct tac ctg    1872
His Phe Leu Ser Gln Thr Lys Gln Ser Gly Glu Asn Leu Pro Tyr Leu
    610                 615                 620 gta gcg tac caa gcc acc gtg tgc gct agg gct caa gcc cct ccc cca    1920
Val Ala Tyr Gln Ala Thr Val Cys Ala Arg Ala Gln Ala Pro Pro Pro
625                 630                 635                 640 tcg tgg gac cag atg tgg aag tgt ttg att cgc ctc aag ccc acc ctc    1968
Ser Trp Asp Gln Met Trp Lys Cys Leu Ile Arg Leu Lys Pro Thr Leu
                645                 650                 655 cat ggg cca aca ccc ctg cta tac aga ctg ggc gct gtt cag aat gaa    2016
His Gly Pro Thr Pro Leu Leu Tyr Arg Leu Gly Ala Val Gln Asn Glu
            660                 665                 670 atc acc ctg acg cac cca gtc acc aaa tac atc atg aca tgc atg tcg    2064
Ile Thr Leu Thr His Pro Val Thr Lys Tyr Ile Met Thr Cys Met Ser
        675                 680                 685 gcc gac ctg gag gtc gtc acg agc gca tgc tcc ggg aag ccg gca atc    2112
Ala Asp Leu Glu Val Val Thr Ser Ala Cys Ser Gly Lys Pro Ala Ile
    690                 695                 700 ata cct gac agg gaa gtc ctc tac cga gag ttc gat gag atg gaa gag    2160
Ile Pro Asp Arg Glu Val Leu Tyr Arg Glu Phe Asp Glu Met Glu Glu
705                 710                 715                 720 tgc tct cag cac tta ccg tac atc gag caa ggg atg atg ctc gcc gag    2208
Cys Ser Gln His Leu Pro Tyr Ile Glu Gln Gly Met Met Leu Ala Glu
                725                 730                 735 cag ttc aag cag aag gcc ctc ggc ctc tcg cga ggg ggc aag ccg gca    2256
Gln Phe Lys Gln Lys Ala Leu Gly Leu Ser Arg Gly Gly Lys Pro Ala
            740                 745                 750 atc gtt cca gac aaa gag gtg ttg tat caa caa tac gat gag atg gaa    2304
Ile Val Pro Asp Lys Glu Val Leu Tyr Gln Gln Tyr Asp Glu Met Glu
        755                 760                 765 gag tgc tca caa gct gcc cca tat atc gaa caa gct cag gta ata gct    2352
Glu Cys Ser Gln Ala Ala Pro Tyr Ile Glu Gln Ala Gln Val Ile Ala
    770                 775                 780
```

```
cac cag ttc aag gaa aaa gtc ctt gga ttg atc gat aat gat caa gtg      2400
His Gln Phe Lys Glu Lys Val Leu Gly Leu Ile Asp Asn Asp Gln Val
785                 790                 795                 800 gtt gtg act cct gac aaa gaa atc tta tat gag gcc ttt gat gag atg      2448
Val Val Thr Pro Asp Lys Glu Ile Leu Tyr Glu Ala Phe Asp Glu Met
            805                 810                 815 gaa gaa tgc gcc tcc aaa gcc gcc ctc att gag gaa ggg cag cgg atg      2496
Glu Glu Cys Ala Ser Lys Ala Ala Leu Ile Glu Glu Gly Gln Arg Met
        820                 825                 830 gcg gag atg ctc aag tct aag ata caa ggc ctc ctc ggg ata ctg cgc      2544
Ala Glu Met Leu Lys Ser Lys Ile Gln Gly Leu Leu Gly Ile Leu Arg
    835                 840                 845 cgg cac gtt ggt cct ggc gag ggg gca gtg cag tgg atg aac cgg ctg      2592
Arg His Val Gly Pro Gly Glu Gly Ala Val Gln Trp Met Asn Arg Leu
850                 855                 860 ata gcc ttc gcc tcc aga ggg aac cat gtt tcc ccc acg cac tac gtt      2640
Ile Ala Phe Ala Ser Arg Gly Asn His Val Ser Pro Thr His Tyr Val
865                 870                 875                 880 ccg tct aga tcc cgg aga ttc gcc cag gcc ctg ccc gtt tgg gcg cgg      2688
Pro Ser Arg Ser Arg Arg Phe Ala Gln Ala Leu Pro Val Trp Ala Arg
            885                 890                 895 ccg gac tat aac ccc ccg cta gtg gag acg tgg aaa aag ccc gac tac      2736
Pro Asp Tyr Asn Pro Pro Leu Val Glu Thr Trp Lys Lys Pro Asp Tyr
        900                 905                 910 gaa cca cct gtg gtc cac ggc aga tct tct cgg aga ttc gcc cag gcc      2784
Glu Pro Pro Val Val His Gly Arg Ser Ser Arg Arg Phe Ala Gln Ala
    915                 920                 925 ctg ccc gtt tgg gcg cgg ccg gac tat aac ccc ccg cta gtg gag acg      2832
Leu Pro Val Trp Ala Arg Pro Asp Tyr Asn Pro Pro Leu Val Glu Thr
930                 935                 940 tgg aaa aag ccc gac tac gaa cca cct gtg gtc cat ggc aga aag acc      2880
Trp Lys Lys Pro Asp Tyr Glu Pro Pro Val Val His Gly Arg Lys Thr
945                 950                 955                 960 aaa cgt aac acc aac cgg cgg ccg cag gac gtc aag ttc ccg ggt ggc      2928
Lys Arg Asn Thr Asn Arg Arg Pro Gln Asp Val Lys Phe Pro Gly Gly
            965                 970                 975 ggt cag atc gtt ggt cgc agg ggc cct cct atc ccc aag gct cgt cgg      2976
Gly Gln Ile Val Gly Arg Arg Gly Pro Pro Ile Pro Lys Ala Arg Arg
        980                 985                 990 ccc gag ggc agg acc tgg gct cag ccc ggt tac cct tgg ccc ctc tat      3024
Pro Glu Gly Arg Thr Trp Ala Gln Pro Gly Tyr Pro Trp Pro Leu Tyr
    995                 1000                1005 ggc aat aag gac aga cgg tct aca ggt aag tcc tgg ggt aag cca ggg      3072
Gly Asn Lys Asp Arg Arg Ser Thr Gly Lys Ser Trp Gly Lys Pro Gly
1010                1015                1020 tac cct tgg cca aga aag acc aaa cgt aac acc aac cga cgg ccg cag      3120
Tyr Pro Trp Pro Arg Lys Thr Lys Arg Asn Thr Asn Arg Arg Pro Gln
1025                1030                1035                1040 gac gtc aag ttc ccg ggt ggc ggt cag atc gtt ggt cgc agg ggc cct      3168
Asp Val Lys Phe Pro Gly Gly Gly Gln Ile Val Gly Arg Arg Gly Pro
            1045                1050                1055 cct atc ccc aag gct cgt cgg ccc gag ggc agg acc tgg gct cag ccc      3216
Pro Ile Pro Lys Ala Arg Arg Pro Glu Gly Arg Thr Trp Ala Gln Pro
        1060                1065                1070 ggt tac cct tgg ccc ctc tat ggc aat aag gac aga cgg tct acc ggt      3264
Gly Tyr Pro Trp Pro Leu Tyr Gly Asn Lys Asp Arg Arg Ser Thr Gly
    1075                1080                1085 aag tcc tgg ggt aag cca ggg tat cct tgg ccc                          3297
Lys Ser Trp Gly Lys Pro Gly Tyr Pro Trp Pro
```

-continued

```
        1090                1095

<210> SEQ ID NO 6
<211> LENGTH: 1099
<212> TYPE: PRT
<213> ORGANISM: Artificial
<220> FEATURE:
<223> OTHER INFORMATION: MEFA 7.1 amino acid sequence

<400> SEQUENCE: 6

Met Ala Thr Lys Ala Val Cys Val Leu Lys Gly Asp Gly Pro Val Gln
  1               5                  10                  15

Gly Ile Ile Asn Phe Glu Gln Lys Glu Ser Asn Gly Pro Val Lys Val
                 20                  25                  30

Trp Gly Ser Ile Lys Gly Leu Thr Glu Gly Leu His Gly Phe His Val
             35                  40                  45

His Glu Phe Gly Asp Asn Thr Ala Gly Cys Thr Ser Ala Gly Pro His
         50                  55                  60

Phe Asn Pro Leu Ser Arg Lys His Gly Gly Pro Lys Asp Glu Glu Arg
 65                  70                  75                  80

His Val Gly Asp Leu Gly Asn Val Thr Ala Asp Lys Asp Gly Val Ala
                 85                  90                  95

Asp Val Ser Ile Glu Asp Ser Val Ile Ser Leu Ser Gly Asp His Cys
                100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
        130                 135                 140

Leu Ala Cys Gly Val Ile Gly Ile Ala Gln Asn Leu Asn Ser Gly Cys
145                 150                 155                 160

Asn Cys Ser Ile Tyr Pro Gly His Ile Thr Gly His Arg Met Ala Trp
                165                 170                 175

Lys Leu Gly Ser Ala Ala Arg Thr Thr Ser Gly Phe Val Ser Leu Phe
            180                 185                 190

Ala Pro Gly Ala Lys Gln Asn Glu Thr His Val Thr Gly Gly Ala Ala
        195                 200                 205

Ala Arg Thr Thr Ser Gly Leu Thr Ser Leu Phe Ser Pro Gly Ala Ser
    210                 215                 220

Gln Asn Ile Gln Leu Ile Val Asp Phe Ile Pro Val Glu Asn Leu Glu
225                 230                 235                 240

Thr Thr Met Arg Ser Pro Val Phe Thr Asp Asn Ser Ser Pro Pro Val
                245                 250                 255

Val Pro Gln Ser Phe Gln Val Ala His Leu His Ala Pro Thr Gly Ser
            260                 265                 270

Gly Lys Ser Thr Lys Val Pro Ala Ala Tyr Ala Ala Gln Gly Tyr Lys
        275                 280                 285

Val Leu Val Leu Asn Pro Ser Val Ala Ala Thr Leu Gly Phe Gly Ala
    290                 295                 300

Tyr Met Ser Lys Ala His Gly Ile Asp Pro Asn Ile Arg Thr Gly Val
305                 310                 315                 320

Arg Thr Ile Thr Thr Gly Ser Pro Ile Thr Tyr Ser Thr Tyr Gly Lys
                325                 330                 335

Phe Leu Ala Asp Gly Gly Cys Ser Gly Gly Ala Tyr Asp Ile Ile Ile
            340                 345                 350

Cys Asp Glu Cys His Ser Thr Asp Ala Thr Ser Ile Leu Gly Ile Gly
```

-continued

```
            355                 360                 365
Thr Val Leu Asp Gln Ala Glu Thr Ala Gly Ala Arg Leu Val Val Leu
    370                 375                 380
Ala Thr Ala Thr Pro Pro Gly Ser Val Thr Val Pro His Pro Asn Ile
385                 390                 395                 400
Glu Glu Val Ala Leu Ser Thr Thr Gly Glu Ile Pro Phe Tyr Gly Lys
                405                 410                 415
Ala Ile Pro Leu Glu Val Ile Lys Gly Gly Arg His Leu Ile Phe Cys
                420                 425                 430
His Ser Lys Lys Lys Cys Asp Glu Leu Ala Ala Lys Leu Val Ala Leu
                435                 440                 445
Gly Ile Asn Ala Val Ala Tyr Tyr Arg Gly Leu Asp Val Ser Val Ile
    450                 455                 460
Pro Thr Ser Gly Asp Val Val Val Ala Thr Asp Ala Leu Met Thr
465                 470                 475                 480
Gly Tyr Thr Gly Asp Phe Asp Ser Val Ile Asp Cys Asn Thr Cys Val
                485                 490                 495
Thr Gln Thr Val Asp Phe Ser Leu Asp Pro Thr Phe Thr Ile Glu Thr
                500                 505                 510
Ile Thr Leu Pro Gln Asp Ala Val Ser Arg Thr Gln Arg Arg Gly Arg
                515                 520                 525
Thr Gly Arg Gly Lys Pro Gly Ile Tyr Arg Phe Val Ala Pro Gly Glu
    530                 535                 540
Arg Pro Ser Gly Met Phe Asp Ser Ser Val Leu Cys Glu Cys Tyr Asp
545                 550                 555                 560
Ala Gly Cys Ala Trp Tyr Glu Leu Thr Pro Ala Glu Thr Thr Val Arg
                565                 570                 575
Leu Arg Ala Tyr Met Asn Thr Pro Gly Leu Pro Val Cys Gln Asp His
                580                 585                 590
Leu Glu Phe Trp Glu Gly Val Phe Thr Gly Leu Thr His Ile Asp Ala
                595                 600                 605
His Phe Leu Ser Gln Thr Lys Gln Ser Gly Glu Asn Leu Pro Tyr Leu
    610                 615                 620
Val Ala Tyr Gln Ala Thr Val Cys Ala Arg Ala Gln Ala Pro Pro Pro
625                 630                 635                 640
Ser Trp Asp Gln Met Trp Lys Cys Leu Ile Arg Leu Lys Pro Thr Leu
                645                 650                 655
His Gly Pro Thr Pro Leu Leu Tyr Arg Leu Gly Ala Val Gln Asn Glu
                660                 665                 670
Ile Thr Leu Thr His Pro Val Thr Lys Tyr Ile Met Thr Cys Met Ser
                675                 680                 685
Ala Asp Leu Glu Val Val Thr Ser Ala Cys Ser Gly Lys Pro Ala Ile
    690                 695                 700
Ile Pro Asp Arg Glu Val Leu Tyr Arg Glu Phe Asp Glu Met Glu Glu
705                 710                 715                 720
Cys Ser Gln His Leu Pro Tyr Ile Glu Gln Gly Met Met Leu Ala Glu
                725                 730                 735
Gln Phe Lys Gln Lys Ala Leu Gly Leu Ser Arg Gly Gly Lys Pro Ala
                740                 745                 750
Ile Val Pro Asp Lys Glu Val Leu Tyr Gln Gln Tyr Asp Glu Met Glu
    755                 760                 765
Glu Cys Ser Gln Ala Ala Pro Tyr Ile Glu Gln Ala Gln Val Ile Ala
770                 775                 780
```

```
His Gln Phe Lys Glu Lys Val Leu Gly Leu Ile Asp Asn Asp Gln Val
785                 790                 795                 800

Val Val Thr Pro Asp Lys Glu Ile Leu Tyr Glu Ala Phe Asp Glu Met
                805                 810                 815

Glu Glu Cys Ala Ser Lys Ala Ala Leu Ile Glu Glu Gly Gln Arg Met
            820                 825                 830

Ala Glu Met Leu Lys Ser Lys Ile Gln Gly Leu Leu Gly Ile Leu Arg
        835                 840                 845

Arg His Val Gly Pro Glu Gly Ala Val Gln Trp Met Asn Arg Leu
    850                 855                 860

Ile Ala Phe Ala Ser Arg Gly Asn His Val Ser Pro Thr His Tyr Val
865                 870                 875                 880

Pro Ser Arg Ser Arg Phe Ala Gln Ala Leu Pro Val Trp Ala Arg
                885                 890                 895

Pro Asp Tyr Asn Pro Pro Leu Val Glu Thr Trp Lys Lys Pro Asp Tyr
                900                 905                 910

Glu Pro Pro Val Val His Gly Arg Ser Ser Arg Phe Ala Gln Ala
                915                 920                 925

Leu Pro Val Trp Ala Arg Pro Asp Tyr Asn Pro Pro Leu Val Glu Thr
            930                 935                 940

Trp Lys Lys Pro Asp Tyr Glu Pro Pro Val Val His Gly Arg Lys Thr
945                 950                 955                 960

Lys Arg Asn Thr Asn Arg Arg Pro Gln Asp Val Lys Phe Pro Gly Gly
                965                 970                 975

Gly Gln Ile Val Gly Arg Arg Gly Pro Pro Ile Pro Lys Ala Arg Arg
            980                 985                 990

Pro Glu Gly Arg Thr Trp Ala Gln Pro Gly Tyr Pro Trp Pro Leu Tyr
        995                 1000                1005

Gly Asn Lys Asp Arg Arg Ser Thr Gly Lys Ser Trp Gly Lys Pro Gly
        1010                1015                1020

Tyr Pro Trp Pro Arg Lys Thr Lys Arg Asn Thr Asn Arg Arg Pro Gln
1025                1030                1035                1040

Asp Val Lys Phe Pro Gly Gly Gly Gln Ile Val Gly Arg Arg Gly Pro
                1045                1050                1055

Pro Ile Pro Lys Ala Arg Arg Pro Glu Gly Arg Thr Trp Ala Gln Pro
            1060                1065                1070

Gly Tyr Pro Trp Pro Leu Tyr Gly Asn Lys Asp Arg Arg Ser Thr Gly
        1075                1080                1085

Lys Ser Trp Gly Lys Pro Gly Tyr Pro Trp Pro
    1090                1095

<210> SEQ ID NO 7
<211> LENGTH: 21
<212> TYPE: PRT
<213> ORGANISM: Artificial
<220> FEATURE:
<223> OTHER INFORMATION: consensus  sequence

<400> SEQUENCE: 7

Gly Ser Ala Ala Arg Thr Thr Ser Gly Phe Val Ser Leu Phe Ala Pro
1               5                   10                  15

Gly Ala Lys Gln Asn
            20

<210> SEQ ID NO 8
```

-continued

```
<211> LENGTH: 10
<212> TYPE: DNA
<213> ORGANISM: Artificial
<220> FEATURE:
<223> OTHER INFORMATION: sequence following HindIII site

<400> SEQUENCE: 8
acaaaacaaa                                                            10

<210> SEQ ID NO 9
<211> LENGTH: 23
<212> TYPE: PRT
<213> ORGANISM: Artificial
<220> FEATURE:
<223> OTHER INFORMATION: NS4A peptide

<400> SEQUENCE: 9

Lys Lys Gly Ser Val Val Ile Val Gly Arg Ile Val Leu Ser Gly Lys
1               5                   10                  15

Pro Ala Ile Ile Pro Lys Lys
            20
```